(12) United States Patent
Jeschko et al.

(10) Patent No.: US 9,828,401 B2
(45) Date of Patent: Nov. 28, 2017

(54) RUTHENIUM-BASED COMPLEX CATALYSTS

(75) Inventors: Julia Maria Jeschko, Gilgenberg (AT); Douglas Stephan, Toronto (CA); Clinton Lund, London (CA); Michael Sgro, Toronto (CA); Christopher Ong, Orange, TX (US); Renan Cariou, Hull (GB)

(73) Assignees: ARLANXEO DEUTSCHLAND GMBH, DORMAGEN (DE); The Governing Council of University of Toronto, Toronto (CA)

( * ) Notice: Subject to any disclaimer, the term of this patent is extended or adjusted under 35 U.S.C. 154(b) by 671 days.

(21) Appl. No.: 14/238,270

(22) PCT Filed: Aug. 15, 2012

(86) PCT No.: PCT/EP2012/065953
§ 371 (c)(1),
(2), (4) Date: Nov. 10, 2014

(87) PCT Pub. No.: WO2013/024119
PCT Pub. Date: Feb. 21, 2013

(65) Prior Publication Data
US 2015/0057450 A1    Feb. 26, 2015

Related U.S. Application Data

(60) Provisional application No. 61/523,555, filed on Aug. 15, 2011.

(51) Int. Cl.

| | | |
|---|---|---|
| C07F 15/00 | (2006.01) | |
| B01J 31/22 | (2006.01) | |
| C07C 29/17 | (2006.01) | |
| C07C 67/303 | (2006.01) | |
| C07D 233/06 | (2006.01) | |
| C07C 209/70 | (2006.01) | |
| C07F 17/02 | (2006.01) | |
| C07C 315/04 | (2006.01) | |
| C07C 319/20 | (2006.01) | |
| C07C 45/62 | (2006.01) | |
| C07C 5/03 | (2006.01) | |
| C07C 231/12 | (2006.01) | |
| C07C 253/30 | (2006.01) | |
| C07D 213/127 | (2006.01) | |
| C07C 5/09 | (2006.01) | |
| C07C 5/05 | (2006.01) | |
| B01J 31/24 | (2006.01) | |

(52) U.S. Cl.
CPC ....... *C07F 15/0046* (2013.01); *B01J 31/2226* (2013.01); *B01J 31/2273* (2013.01); *B01J 31/2404* (2013.01); *C07C 5/03* (2013.01); *C07C 5/05* (2013.01); *C07C 5/09* (2013.01); *C07C 29/175* (2013.01); *C07C 45/62* (2013.01); *C07C 67/303* (2013.01); *C07C 209/70* (2013.01); *C07C 231/12* (2013.01); *C07C 253/30* (2013.01); *C07C 315/04* (2013.01); *C07C 319/20* (2013.01); *C07D 213/127* (2013.01); *C07D 233/06* (2013.01); *C07F 17/02* (2013.01); *B01J 2231/645* (2013.01); *B01J 2531/821* (2013.01); *B01J 2540/10* (2013.01); *C07B 2200/07* (2013.01); *C07C 2531/22* (2013.01); *C07C 2531/24* (2013.01); *C07C 2601/14* (2017.05)

(58) Field of Classification Search
CPC .................................................. C07F 15/0046
See application file for complete search history.

(56) References Cited

FOREIGN PATENT DOCUMENTS

JP    2001-97988    *   4/2001    .......... C07F 15/0046

OTHER PUBLICATIONS

Cetinkaya et al. "Ruthenium-carbene catalysts for the synthesis of 2,3-dimethylfuran" Journal of Molecular Catalysis A: Chemical, 1997, vol. 118, pp. L1-L4.*
del Pozo et al. "Pincer-type Pyridine-Based N-Heterocyclic Carbene Amine Ru(II) Complexes as Efficient Catalysts for Hydrogen Transfer Reactions" Organometallics, 2011, vol. 30, pp. 2180-2188.*
Kodama et al., Machine translation of JP 2001-97988.*
Pei Ling Chiu et al: "Chemistry of the PCNHCP Ligand: Silver and Ruthenium complexes, facial/meridional coordination, and catalytic transfer hydrogenation", Organometallics, ACS, vol. 24, No. 7, pp. 1692-1702, Mar. 28, 2005, XP001236746.
Murat Ygit et al: "Actve ruthenium(n-heterocyclic carbene) complexes for hydrogenation of ketones", Applied Organometallic Chemistry, vol. 20, 2006, pp. 322-327, XP002686586.
Cetinkaya et al: "Synthesis and catalytic properties of N-functionalized carbene complexes of rhodium(I) and ruthenium(II)", Journal of Organometallic Chemistry, vol. 534, No. 1-2, Apr. 28, 1997, pp. 153-158, XP005258548.
Hitchcock, P. B. et al: "Carbene complexes. Part 14. The synthesis and steric and electronic effects in electron-rich olefin-derived bis-, tris, and tetrakis-(carbene)-ruthenium(II) and a tetrakis(carbene) osmium(II) comples; the crystal and molecular structure of trans-dichlorotetrakis(1,3-diethylimidazolidin-2-ylidene) ruth", Journal of the Chemical Society, Dalton Transactions, Chemical Society, Jan. 1, 1978, pp. 826-836, XP002636747.
John P. Lee et al: "Six, Five and Four Coordinate Ruthenium (II) Hydride Complexes Supported by N-Heterocyclic Carbene Ligands: Synthesis, Characterization, Fundamental Reactivity and Catalytic Hydrogenation of Olefins, Aldehydes and Ketones", Organometallics, vol. 28, 2009, pp. 1758-1775, XP002686587.
Hu, J. "Hydrogenation of Nitrile Butadiene Rubber Catalyzed by [IR(COD) py(PCy3)] PF6", Chemical Industries, vol. 104, pp. 125-134.
Hallman, P.S., "Selective Catalytic Homogeneous Hydrogenation of Terminal Olefins using Tris(triphenylphosphine) hydridochlororuthenium(II); Hydrogen Transfer in Exchange and Isomerisation Reactions of Olefins", Chemical Communications, No. 7, 1967, pp. 305-306.
McManus, N.T., "Improvements in the Hydrogenation of Nitrile Rubber using Wilkinson's Catalyst", American Chemical Society, Rubber Chemistry and Technology, vol. 81, No. 2, 2008, pp. 227-243.
Abdur-Rashid, K., "Coordinatively unsaturated hydridoruthenium(II) Complexes of N-Heterocyclic Carbenes", Organometallics, 2004, 23, pp. 86-94.

(Continued)

Primary Examiner — Joseph Kosack

(57) ABSTRACT

The present invention provides novel Ruthenium-based transition metal complex catalysts comprising specific ligands, their preparation and their use in hydrogenation processes. Such complex catalysts are inexpensive, thermally robust, and olefin selective.

19 Claims, 2 Drawing Sheets

(56) References Cited

OTHER PUBLICATIONS

Bhattacharjee, S. "High-Pressure Hydrogenation of Nitrile Rubber: Thermodynamics and Kinetics", Ind. Eng. Chem. Res., 1991, 30, pp. 1086-1092.
Guo, X., "Catalytic Hydrosilylation of diene-Based Polymers. 2. Hydrosilylation of Styrene-Butadiene Copolymer and Nitrile-Butadiene Copolymer", Macromolecules, 1992, 25, pp. 883-886.
International Search Report from co-pending Application PCT/EP2012/065953 dated Nov. 9, 2012, 2 pages.
Belger, C. "A selective Ru-Catalyzed Semireduction of Alkynes to Z Olefins under Transfer-Hydrogenation Conditions", Chem. Eur. J., 2010, 16 pp. 12214-12220.
Mao, T.F., "Catalytic Hydrogenation of nitrile-butadiene copolymers by catonic rhodium complexes", Journal of Molecular Catalysis A: Chemical 135, 1998, pp. 121-132.
Jardine, I. "Homogeneous and Heterogeneous Hydrogenation", Tetrahedron Letters No. 40, pp. 4871-4875, 1996.
Joseph, T. "Hydrogenation of olefins over hydrido chlorocarbonyl tris-(triphenylphosphine) ruthenium (II) complex immobilized on functionalized MCM-41 and SBA-15", Journal of Molecular Catalysis A: Chemical 206, 2003, pp. 13-21.
Balaraman, E., "Direct Hydrogenation of Amides to Alcohols and Amines Under Mild Conditions", J. Am. Chem. Soc., 2010, 132, pp. 16756-16758.
Beach, J., "Hydrogenolysis versus Methanolysis of First- and Second-Generation Grubbs Catalysts: Rates, Speciation, and Implications for Tandem Catalysis", Organometallics, 2010, 29, pp. 5450-5455.
Chatwin, S. "H-X Bond Activation via Hydrogen Transfer to Hydride in Ruthenium N-Heterocyclic Carbene Complexes: Density Functional and Synthetic Studies", Organometallics 2006, 25, pp. 99-110.
J. Am. Chem. Soc., 1961, 83, pp. 1262-1263.

\* cited by examiner

RUTHENIUM-BASED COMPLEX CATALYSTS

FIELD OF THE INVENTION

The present invention relates to novel Ruthenium-based transition metal complex catalysts, their preparation and their use in hydrogenation processes.

BACKGROUND OF THE INVENTION

In Ind. Eng. Chem. Res. 1991, 30, 1086-1092, Macromolecules 1992, 25, 883-886, J. Mol. Catal. A: Chem. 1998, 135, 121-132 and Rubber Chem. Technol. 2008, 81, 227-243 the Rhodium-based catalyst tris(triphenylphosphine)rhodium(I)chloride of formula (1) is disclosed for hydrogenation and hydrosilylation reactions of rubbers. However, high costs are associated with this catalyst which additionally requires the use of triphenylphosphine as co-catalyst. The catalyst degrades at 145° C.

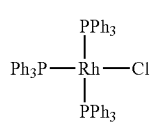

(1)

In Chem. Comm. 1967, 305-306, Chem. Eur. J. 2010, 16, 12214-12220 and Tetrahedron Lett. 1966, 4871-4875 it is disclosed that the complex tris(triphenylphosphine) hydrido ruthenium chloride of formula (2) can be used in a transfer hydrogenation for converting alkynes to alkenes. However, such catalyst does not efficiently hydrogenate nitrile rubbers and it is not selective for only olefins.

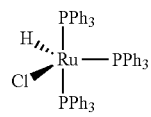

(2)

According to Organometallics 2004, 23, 86-94, the catalyst of formula (3) as shown below can be prepared from RuHCl(PPh$_3$)$_3$ and two equivalents of SIMes$_2$ with the formation of SIMes$_2$.HCl as a by-product. However, no hydrogenation data is reported. It is not possible to displace PPh$_3$ with SIMes$_2$ without CH activation of the methyl groups.

In Organometallics 2006, 25, 99-110, Dalton Trans. 2008, 2603-2614. Organometallics 2009, 28, 1758-1775. Inorg. Chim Acta. 2010, 363, 625-632 and Organometallics, 2010, 29, 5450-5455 the catalyst of formula (4) as shown below is prepared from RuHCl(CO)(AsPh$_3$)$_3$ and IMes$_2$. Such preparation method, however, is not favourable due to the presence of AsPh$_3$. The catalyst further contains a CO group. Such catalyst is described for transfer hydrogenation of aromatic ketones with alcohols. It also hydrogenates olefins and ketones using H$_2$, however, it is not selective for olefins.

In J. Am. Chem. Soc. 1961, 83, 1262-1263, Chem. Ear. J. 2010, 16, 12214-12220, Am. Chem. Soc. 2010, 132, 16756-16758 and J. Mol. Catal A: Chem. 2003, 206, 13-21 the catalyst of formula (5) as shown below is used as a transfer hydrogenation catalyst for alkynes to alkenes and for hydrogenation of amides to alcohols and amines under H$_2$. However, such a catalyst is not selective for olefins and contains a CO group.

In Chemical Industries 2005, 104, 125-134 the catalyst of formula (6) as shown below is described for the hydrogenation of rubbers. High costs, facile catalyst deactivation and low thermal stability are some of detrimental attributes of this catalyst.

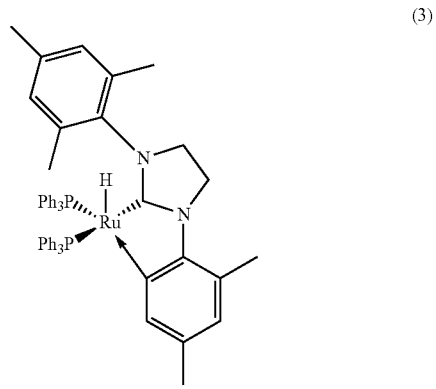

(3)

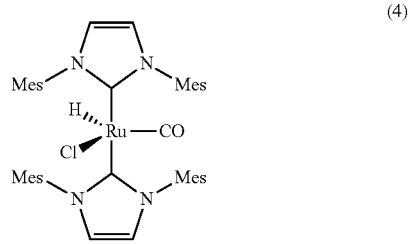

(4)

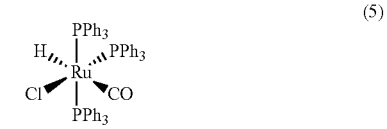

(5)

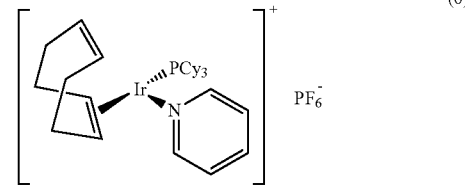

(6)

Summing up various catalysts are already available for hydrogenation reactions, however, many of them contain unfavourable ligands, are difficult to prepare and not sufficiently active and/or selective.

Therefore, it was the object of the present invention to provide an inexpensive, thermally robust, and olefin selective novel catalyst for hydrogenation reactions particularly for hydrogenating polymers and even more particularly for hydrogenating nitrile rubbers.

SUMMARY OF THE INVENTION

The above-mentioned objects have now been solved by providing novel Ruthenium-based complex catalysts according to general formula (I)

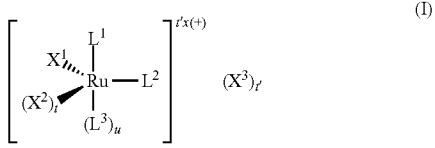

wherein
$X^1$ and $X^2$ are identical or different and represent anionic ligands,
$X^3$ represents a non-coordinating anion,
t is either 0 or 1,
t' is either 0 or 1,
u is either 0 or 1, wherein u and t may not both represent 0 at the same time,
$L^1$, $L^2$ and $L^3$ represent identical or different ligands, wherein at least one of $L^1$, $L^2$ and (if u=1) $L^3$ represents either a ligand having the general structure (Ia*) or (Ib*)

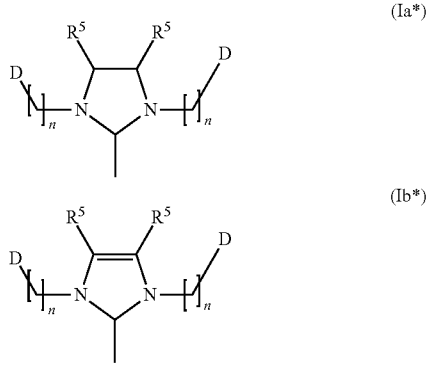

or a ligand having the general structure (Ic*) or (Id*)

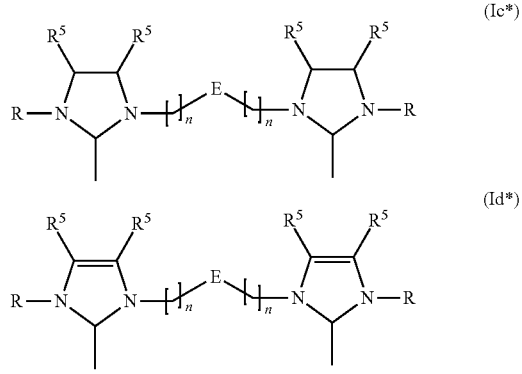

in which formulae (Ia*), (Ib*), (Ic*) and (Id*)
n is identical or different and represents an integer in the range of from 1 to 20,
D is identical or different and represents hydroxy, alkoxy, aryloxy, thiol, thiolate, thioether, selenol, selenoether, amine, phosphine, phosphate, phosphite, arsine, sulfoxide, sulfone, alkyl, phosphinimine, aminophosphine, carbene, selenoxide, imidazoline, imidazolidine, phosphine oxide, phosphine sulfide, phosphine selenide, ketone, ester, pyridyl, substituted pyridyl or any moiety able of acting as a two electron donor,
R is identical or different and represents H, alkyl or aryl, and
E is identical or different and represents a divalent moiety able of acting as a two electron donor selected from the group consisting of —O—, —S—, —Se—, —N(R)—, —P(R)—, —As(R)—, —S(=O)—, —PR(=S)—, —PR(=O)—, —C(=O)—, —C(=S)—, 2,6-pyridylene, substituted 2,6-pyridylene and any other divalent moiety able of acting as a two electron donor, and
$R^5$ are identical or different in a respective moiety (Ia*), (Ib*), (Ic*) or (Id*) and represent H, alkyl, aryl, halide, preferably chloride, or in the alternative two $R^5$ together with the two adjacent carbon atoms to which they are bound in a moiety (Ia*), (Ib*), (Ic*) or (Id*) form a fused-on five- or six-membered saturated or unsaturated ring.

DETAILED DESCRIPTION OF THE INVENTION

Figure 1:
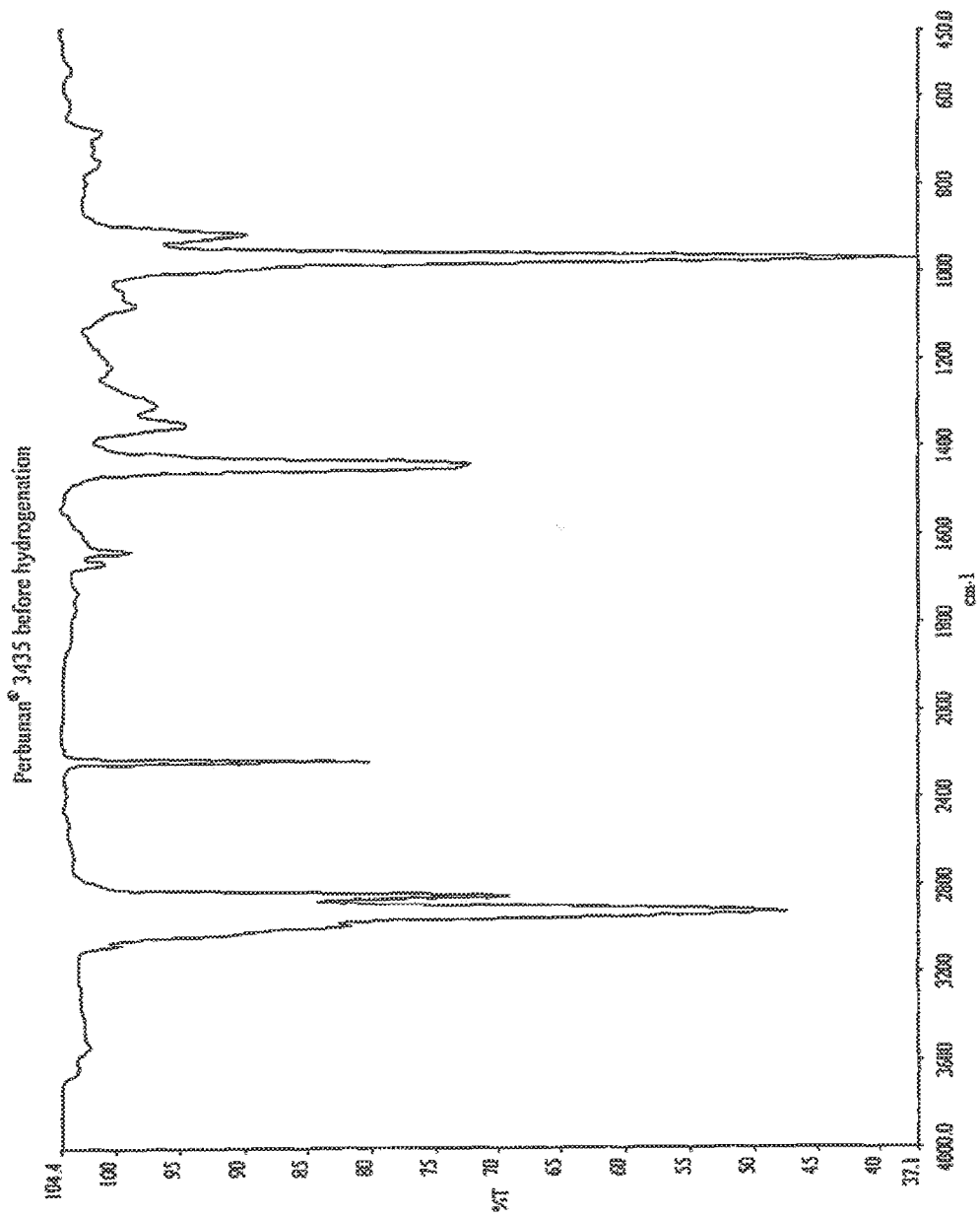
FIG. 1 shows an IR emission spectrum of the nitrile rubber Perbunan®T 3435 before hydregenation.

The novel Ruthenium-based catalysts are excellently suited for hydrogenation reactions, are thermally robust, use less expensive ruthenium as transition metal and more importantly are selective for olefin hydrogenation.

The term "substituted" used for the purposes of the present patent application means that a hydrogen atom on an indicated radical or atom has been replaced by one of the groups indicated in each case, with the proviso that the valency of the atom indicated is not exceeded and the substitution leads to a stable compound.

For the purposes of the present patent application and invention, all the definitions of radicals, parameters or explanations given above or below in general terms or in preferred ranges can be combined with one another in any way, i.e. including combinations of the respective ranges and preferred ranges.

In a preferred embodiment the present invention relates to Ruthenium-based complex catalysts according to general formula (I)

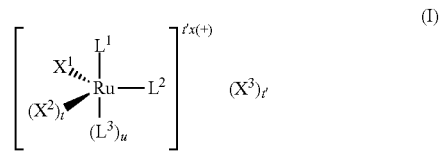

wherein
X¹ and X² are identical or different and represent anionic ligands,
X³ represents a non-coordinating anion,
t is either 0 or 1,
t' is either 0 or 1,
u is either 0 or 1, wherein u and t may not both represent 0 at the same time,
L¹, L² and L³ represent identical or different ligands, wherein at least one of L¹, L² and (if u=1) L³ represents either a ligand having the general structure (Ia) or (Ib)

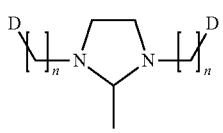

(Ia)

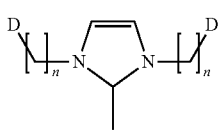

(Ib)

or a ligand having the general structure (Ic) or (Id)

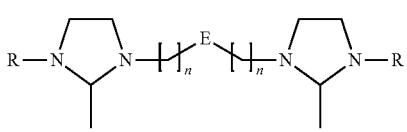

(Ic)

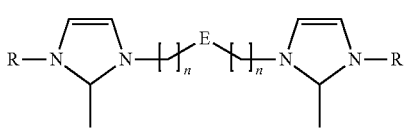

(Id)

in which formulae (Ia), (Ib), (Ic) and (Id)

n is identical or different and represents an integer in the range of from 1 to 20, D is identical or different and represents hydroxy, alkoxy, aryloxy, thiol, thiolate, thioether, selenol, selenoether, amine, phosphine, phosphate, phosphite, arsine, sulfoxide, sulfone, alkyl, phosphinimine, aminophosphine, carbene, selenoxide, imidazoline, imidazolidine, phosphine oxide, phosphine sulfide, phosphine selenide, ketone, ester, pyridyl, substituted pyridyl or any moiety able of acting as a two electron donor, R is identical or different and represents H, alkyl or aryl, and E is identical or different and represents a divalent moiety able of acting as a two electron donor selected from the group consisting of —O—, —S—, —Se—, —N(R)—, —P(R)—, —As(R)—, —S(=O)—. —PR(=S)—, —PR(=O)—, —C(=O)—, —C(=S)—, 2,6-pyridylene, substituted 2,6-pyridylene and any other divalent moiety able of acting as a two electron donor.

In a further preferred embodiment the present invention provides a catalyst according to general formula (I) wherein L¹, L², L³ represent identical or different ligands, wherein at least one of L¹, L² and (if u=1) L³ represents either a ligand having the general structure (Ia) or (Ib) or a ligand having the general structure (Ic) or (Id) and wherein
n, R and E have the same meanings as outlined above, and
D is identical or different and represents hydroxy, alkoxy, aryloxy, thiol, thiolate, thioether, sulfoxide, sulfone, phosphine oxide, phosphine sulfide, ketone, ester, or any moiety able of acting as a two electron donor.

In a more preferred embodiment the present invention relates to Ruthenium-based complex catalysts according to general formula (I) wherein
X¹, X², X³, t, t', u, have the same meanings as outlined above for formula (I) and wherein u and t may not both represent 0 at the same time,
L¹, L² and L³ represent identical or different ligands, wherein at least one of L¹, L² and (if u=1) L³ represents either a ligand having the general structure (Ia) or (Ib) or a ligand having the general structure (Ic) or (Id) with n, R, E and D having the above meanings and wherein all remainder ligands L¹, L² and (if u=1) L³ represent two electron donor ligands.

In an even more preferred embodiment the present invention relates to Ruthenium-based complex catalysts according to general formula (I) wherein
X¹, X², X³, t, t', u, have the same meanings as outlined above for formula (I) and wherein u and t may not both represent 0 at the same time,
L¹, L² and L³ represent identical or different ligands, wherein at least one of L¹, L² and (if u=1) L³ represents either a ligand having the general structure (Ia) or (Ib) or a ligand having the general structure (Ic) or (Id) with n, R, E and D having the above meanings, and
wherein the remainder ligands of L¹, L² and (if u=1) L³ are selected from the group consisting of PPh₃, P(p-Tol)₃, P(o-Tol)₃, PPh(CH₃)₂, P(CF₃)₃, P(p-FC₆H₄)₃, P(p-CF₃C₆H₄)₃, P(C₆H₄—SO₃Na)₃, P(CH₂C₆H₄—SO₃Na)₃, P(isopropyl)₃, P(CHCH₃(CH₂CH₃))₃, P(cyclopentyl)₃, P(cyclohexyl)₃, P(neopentyl)₃ P(benzyl)₃ and from an imidazoline or imidazolidine ligand having the general formulae (IIa), or (IIb),

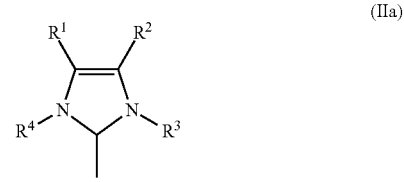

(IIa)

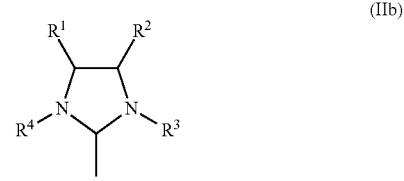

(IIb)

wherein, under the proviso that the ligand(s) according to formulae (IIa) and (IIb) are different from those of the general formulae (Ia), (Ib), (Ic) and (Id), R¹, R², R³, R⁴ are identical or different and are each hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$ alkoxycarbonyl, $C_1$-$C_{20}$-alkylthio, $C_6$-$C_{20}$-arylthio, $C_2$-$C_{20}$-alkylsulphonyl, $C_1$-$C_{20}$-alkylsulphonate, $C_6$-$C_{20}$-arylsulphonate or $C_1$-$C_{20}$-alkylsulphinyl, or in the alternative $R^3$ and $R^4$ have the above mentioned meanings and $R^1$ and $R^2$ jointly form a $C_6$-$C_{10}$ fused-on five or six-membered cyclic structure together with the two adjacent carbon atoms in the imidazoline or imidazolidine ring.

Ligand Definition:

In the catalysts of the general formula (I), $X^1$ and $X^2$ are identical or different and represent two anionic ligands.

$X^1$ and $X^2$ can be, for example, hydride, halide, pseudohalide, alkoxide, amide, triflate, phosphate, borate, carboxylate, acetate, halogenated acetate, halogenated alkylsulfonate, tosylate or any weakly coordinating anionic ligands. $X^1$ and $X^2$ can also be, for example, straight-chain or branched $C_1$-$C_{30}$-alkyl or $C_6$-$C_{24}$-aryl.

In a preferred embodiment, $X^1$ and $X^2$ are identical or different and shall mean hydride, halide, in particular fluoride, chloride, bromide or iodide, phosphate, borate, carboxylate, acetate, trifluoroacetate, trifluormethylsulfonate or tosylate.

In a particularly preferred embodiment, $X^1$ and $X^2$ are different and shall mean hydride or halide. In particular $X^1$ and $X^2$ are different and represent hydride and chloride.

$X^3$ represents a non-coordinating anion acting as a counterion. It represents a counterion with a single negative charge or an equivalent thereof. In one embodiment $X^3$ can have the meaning $(ERV^1_4)^-$ in which E means B, Al, or Ga and $R^1$ are identical or different having the same meanings as outlined above for $X^1$ and $X^2$. $X^3$ represents e.g. $BF_4^-$; $ClO_4^-$, $[B(3,5\text{-}(CF_3)_2C_6H_3)_4]^-$, $B(C_6F_5)_4^-$, $B(CF_3SO_3)_4^-$, $B(RSO_3)^-$ (with R having the same meanings as defined above for structures (Ic) and (Id)) and $Al(OC(CF_3)_3)_4^-$. In the alternative $X^3$ represents e.g. $PF_6^-$ or $AgBr_2^-$.

In the general formula (I), the symbols $L^1$, $L^2$ and $L^3$ represent identical or different ligands and are preferably uncharged electron donors with the following proviso: At minimum at least one of the ligands $L^1$, $L^2$ and (if u=1) $L^3$ represents a ligand having the following structure (Ia) or (Ib)

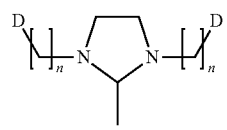
(Ia)

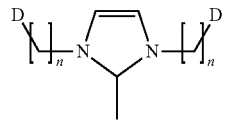
(Ib)

or a ligand having the structure (Ic) or (Id)

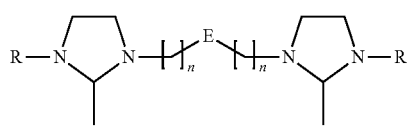
(Ic)

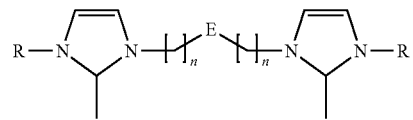
(Id)

in which formulae (Ia), (Ib), (Ic) and (Id)

n is identical or different and represents an integer in the range of from 1 to 20

D is identical or different and represents hydroxy, alkoxy, aryloxy, thiol, thiolate, thioether, selenol, selenoether, amine, phosphine, phosphate, phosphite, arsine, sulfoxide, sulfone, alkyl, phosphinimine, aminophosphine, carbene, selenoxide, imidazoline, imidazolidine, phosphine oxide, phosphine sulfide, phosphine selenide, ketone, ester, pyridyl, substituted pyridyl, or any moiety able of acting as a two electron donor, R is identical or different and represents H, alkyl, or aryl, and E is identical or different and represents a divalent moiety able of acting as a two electron donor selected from the group consisting of —O—, —S—, —Se—, —N(R)—, —P(R)—, —As(R)—, —S(=O)—, —PR(=S)—, —PR(=O)—, —C(=O)—, —C(=S)—, 2,6-pyridinylene, substituted 2,6-pyridinylene and any other divalent moiety able of acting as a two electron donor.

In one embodiment of the novel catalysts the alkyl and aryl groups R can be substituted by one or more substituents, such substituents representing preferably straight-chain or branched $C_1$-$C_{10}$-alkyl, $C_3$-$C_8$-cycloalkyl, $C_1$-$C_{10}$-alkoxy or $C_6$-$C_{24}$-aryl, where these substituents may in turn be substituted by one or more functional groups, preferably functional groups selected from the group consisting of halide, $C_1$-$C_5$-alkyl, $C_1$-$C_5$-alkoxy, phenyl and substituted phenyl.

The ligands pursuant to formulae (Ia) and (Ib) may act as monodentate, but in some cases also as bi- or tridentate ligands depending on their structure as well as depending on the other ligands in the complex. The ligands pursuant to formulae (Ic) and (Id) may act as bidentate ligands, but in some cases also as tridentate ligands depending on their structure as well as depending on the other ligands in the complex.

In a preferred embodiment catalysts of the general formula (I) are provided in which at least one of the ligands $L^1$, $L^2$ and (if u=1) $L^3$ represents a ligand having the structure (Ia) or (Ib) in which n is identical or different and represents an integer in the range of from 1 to 10 and D is identical or different and represents $C_1$-$C_{20}$-alkoxy, $C_6$-$C_{24}$-aryloxy or $C_1$-$C_{10}$-thioether.

In a more preferred embodiment at least one of the ligands $L^1$, $L^2$ and (if u=1) $L^3$ represents a ligand having the structure (Ia) or (Ib) in which n is identical or different and represents an integer in the range of from 1 to 5, and D is identical or different and represents $C_1$-$C_{10}$-alkoxy or $C_6$-$C_{14}$-aryloxy.

In a particularly preferred embodiment one ligand of $L^1$, $L^2$ and (if u=1) L is selected from the formulae (Ia-1) and, (Ib-1)

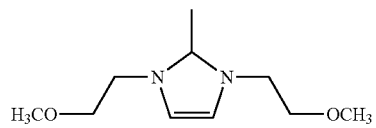
(Ia-1)

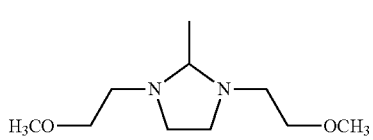

(Ib-1)

In another preferred embodiment at least one ligand of $L^1$, $L^2$ and (if u=1) $L^3$ represents a ligand having the structure (Ic) or (Id) in which n is identical or different and represents an integer in the range of from 1 to 10, E is identical or different and represents oxygen or sulfur, and R is identical or different and represents $C_1$-$C_{20}$-alkyl or $C_6$-$C_{24}$-aryl.

In a more preferred embodiment at least one ligand of $L^1$, $L^2$ and (if u=1) L represents a ligand having the structure (Ic) or (Id) in which n is identical or different and represents an integer in the range of from 1 to 5, E is identical or different and represents oxygen or sulfur, and R is identical or different and represents $C_1$-$C_{10}$ alkyl or $C_6$-$C_{14}$ aryl.

In a particularly preferred embodiment one ligand of $L^1$, $L^2$ and (if u=1) $L^3$ represents a tridentate ligand having the formula (Ic-1)

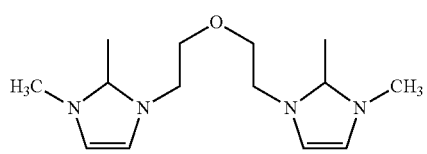

(Ic-1)

Definition of Remainder Ligands of $L^1$, $L^2$ and (if u=1) $L^3$

Apart from this proviso that at least one of $L^1$, $L^2$ and (if u=1) $L^3$ in general formula (I) represents either a ligand having the general structure (Ia) or (Ib) or a ligand having the general structure (Ic) or (Id) the remaining ligand(s) of $L^1$, $L^2$ and (if u=1) $L^3$ can, for example, be, independently of one another and as long as they are different from the definitions according to formulae (Ia), (Ib), (Ic) and (Id) phosphine, sulfonated phosphine, substituted sulfonated phosphine, phosphine oxide, phosphine sulfide, phosphine selenide, phosphinimine, aminophosphine, phosphate, phosphinite, substituted phophinite, phosphonite, phosphite, substituted phosphite, arsine, substituted arsine, stibine, an amine, substituted amine, amide, sulfoxide, sulfone, carboxyl, nitrosyl, pyridine, substituted pyridine, alkyl, carbene, alkoxy, aryloxy, thiol, thioether, selenol, selenoether, selenoxide, ketone, ester, an imidazoline or imidazolidine ligand other than the above or any other moiety able of acting as a two electron donor.

Apart from this proviso that at least one of $L^1$, $L^2$ and (if u=1) $L^3$ in general formula (I) represents either a ligand having the general structure (Ia) or (Ib) or a ligand having the general structure (Ic) or (Id) the remaining ligand(s) of $L^1$, $L^2$ and (if u=1) $L^3$ preferably represent, independently of one another and as long as they are different from the definitions according to formulae (Ia), (Ib), (Ic) and (Id) phosphine, sulfonated phosphine, substituted sulfonated phosphine, phosphinimine, aminophosphine, phosphinite, substituted phophinite, phosphonite, phosphite, substituted phosphite, arsine, substituted arsine, stibine, an amine, substituted amine, amide, carboxyl, nitrosyl, pyridine, substituted pyridine, carbene, thiol, selenol, an imidazoline or imidazolidine ligand other than the above or any other moiety able of acting as a two electron donor.

Under compliance with the above proviso that at least one of $L^1$, $L^2$ and (if u=1) $L^3$ in general formula (I) represents either a ligand having the general structure (Ia) or (Ib) or a ligand having the general structure (Ic) or (Id) preference is given to the remaining ligand(s) of $L^1$, $L^2$ and (if u=1) $L^3$ being, independently of one another, a $C_6$-$C_{24}$-arylphosphine, $C_1$-$C_{10}$-alkylphosphine or $C_3$-$C_{20}$-cycloalkylphosphine ligand, a sulfonated $C_6$-$C_{24}$-arylphosphine or sulfonated $C_1$-$C_{10}$-alkylphosphine ligand, a $C_6$-$C_{24}$-arylphosphinite or $C_1$-$C_{10}$-alkylphosphinite ligand, a $C_6$-$C_{24}$-arylphosphonite or $C_1$-$C_{10}$-alkylphosphonite ligand, a $C_6$-$C_{24}$-aryl phosphite or $C_1$-$C_{10}$-alkyl phosphite ligand, a $C_6$-$C_{24}$-arylarsine or $C_1$-$C_{10}$-alkylarsine ligand, a $C_6$-$C_{24}$-arylamine or $C_1$-$C_{10}$-alkylamine ligand, an optionally substituted pyridine ligand, a $C_6$-$C_{24}$-aryl sulfoxide or $C_1$-$C_{10}$-alkyl sulfoxide ligand, a $C_6$-$C_{24}$-aryloxy or $C_1$-$C_{10}$-alkyloxy ligand or a $C_6$-$C_{24}$-arylamide or $C_1$-$C_{10}$-alkylamide ligand, each of which may be substituted by a phenyl group which may in turn be substituted by a halogen-, $C_1$-$C_5$-alkyl or $C_1$-$C_5$-alkoxygroup.

The term "phosphine" includes, for example, $PPh_3$, P(p-Tol)$_3$, P(o-Tol)$_3$, $PPh(CH_3)_2$, $P(CF_3)_3$, P(p-FC$_6$H$_4$)$_3$, P(p-CF$_3$C$_6$H$_4$)$_3$, P(C$_6$H$_4$—SO$_3$Na)$_3$, P(CH$_2$C$_6$H$_4$—SO$_3$Na)$_3$, P(isopropyl)$_3$, P(CHCH$_3$(CH$_2$CH$_3$))$_3$, P(cyclopentyl)$_3$, P(cyclohexyl)$_3$, P(neopentyl)$_3$ and P(benzyl)$_3$.

The term "phosphinite" includes, for example, phenyl diphenylphosphinite, cyclohexyl dicyclohexylphosphinite, isopropyl diisopropylphosphinite and methyl diphenylphosphinite.

The term "phosphite" includes, for example, triphenyl phosphite, tricyclohexyl phosphite, tri-tert-butyl phosphite, triisopropyl phosphite and methyl diphenyl phosphite.

The term "stibine" includes, for example, triphenylstibine, tricyclohexylstibine and trimethylstibine.

The term "sulphonate" includes, for example, trifluoromethanesulphonate, tosylate and mesylate.

The term "sulfoxide" includes, for example, (CH$_3$)$_2$S (═O) and (C$_6$H$_5$)$_2$S═O.

The term "thioether" includes, for example, CH$_3$SCH$_3$, C$_6$H$_5$SCH$_3$, CH$_3$OCH$_2$CH$_2$SCH$_3$ and tetrahydrothiophene.

For the purposes of the present application, the term "pyridine" is used as a collective term for all nitrogen-containing ligands as are mentioned by, for example, Grubbs in WO-A-03/011455. Examples are: pyridine, picolines (α-, β- and γ-picoline), lutidines (2,3-, 2,4-, 2,5-, 2,6-, 3,4- and 3,5-lutidine), collidine (2,4,6-trimethylpyridine), trifluoromethylpyridine, phenylpyridine, 4-(dimethylamino) pyridine, chloropyridines, bromopyridines, nitropyridines, quinoline, pyrimidine, pyrrole, imidazole and phenylimidazole.

If one or two of the remaining ligands of $L^1$, $L^2$ and (if u=1) $L^3$ is/are an imidazoline or imidazolidine ligand other than the ligands having the formulae (Ia), (Ib), (Ic) or (Id), this imidazoline or imidazolidine ligand by definition usually has a structure corresponding to the general formulae (IIa), or (IIb),

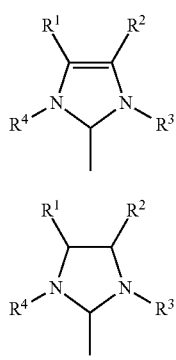

(IIa)

(IIb)

wherein, under the proviso that these ligands according to formulae (IIa) and (IIb) are different from the general formulae (Ia), (Ib), (Ic) and (Id), $R^1$, $R^2$, $R^3$, $R^4$ are identical or different and are each hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-alkoxycarbonyl, $C_1$-$C_{20}$-alkylthio, $C_6$-$C_{20}$-arylthio, $C_1$-$C_{20}$-alkylsulphonyl, $C_1$-$C_{20}$-alkylsulphonate, $C_6$-$C_{20}$-arylsulphonate or $C_1$-$C_{20}$-alkylsulphinyl or in the alternative $R^3$ and $R^4$ have the above mentioned meanings and $R^1$ and $R^2$ jointly form a $C_6$-$C_{10}$ cyclic structure together with the two adjacent carbon atoms in the imidazoline or imidazolidine ring.

Again under the proviso that the ligands according to formulae (IIa) and (IIb) are different from the ligand structures (Ia), (Ib), (Ic), and (Id) one or more of the substituents $R^1$, $R^2$, $R^3$, $R^4$ can, if appropriate, independently of one another, be substituted by one or more substituents, preferably straight-chain or branched $C_1$-$C_{10}$-alkyl, $C_3$-$C_8$-cycloalkyl, $C_1$-$C_{10}$-alkoxy or $C_6$-$C_{24}$-aryl, where these abovementioned substituents may in turn be substituted by one or more functional groups, preferably functional groups selected from the group consisting of halogen, in particular chlorine or bromine, $C_1$-$C_5$-alkyl, $C_1$-$C_5$-alkoxy and phenyl.

Merely for the sake of clarity, it may be added that the structures of the imidazoline or imidazolidine ligands depicted in the general formulae (IIa) and (IIb) in the present application are equivalent to the structures (IIa'), and (IIb') which are frequently also found in the literature for this type of ligands and emphasize the carbene character of the imidazoline or imidazolidine ligand. This applies analogously to the associated preferred structures (III-a)-(I-o) depicted below and to the structure (Ia), (Ib), (Ic) and (Id).

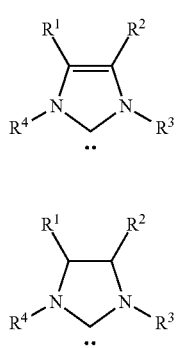

(IIa)

(IIb)

For all following preferred embodiments the same proviso as mentioned above shall apply, i.e. in any case the meanings of $R^1$, $R^2$, $R^3$, $R^4$ shall be chosen in a way that the imidazoline or imidazolidine ligands having the formulae (IIa) and (IIb) (or (IIa') and (IIb') and (III-a)-(III-o), respectively) must be different from the ligands having the formulae (Ia), (Ib), (Ic) or (Id).

In a preferred embodiment of the catalysts of the general formula (I), $R^1$ and $R^2$ are each, independently of one another, hydrogen, $C_6$-$C_{24}$-aryl, particularly preferably phenyl, straight-chain or branched $C_1$-$C_{10}$-alkyl, particularly preferably propyl or butyl, or together with the carbon atoms to which they are bound form a $C_6$-$C_{10}$ cycloalkyl or $C_6$-$C_{10}$ aryl substituent, preferably a phenyl ring in structure (IIa) (structure (IIa') respectively) where all the above mentioned substituents may in turn be substituted by one or more further substituents selected from the group consisting of straight-chain or branched $C_1$-$C_{10}$-alkyl, $C_1$-$C_{10}$-alkoxy, $C_6$-$C_{24}$-aryl and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen.

In a preferred embodiment of the catalysts of the general formula (I), the substituents $R^3$ and $R^4$ are identical or different and are each straight-chain or branched $C_1$-$C_{10}$-alkyl, particularly preferred i-propyl or neopentyl, $C_3$-$C_{10}$-cycloalkyl, particularly preferred adamantyl, $C_6$-$C_{24}$-aryl, particularly preferred phenyl, $C_1$-$C_{10}$-alkylsulphonate, particularly preferred methanesulphonate, $C_6$-$C_{10}$-arylsulphonate, particularly preferred p-toluenesulphonate.

The abovementioned substituents as meanings of $R^3$ and $R^4$ may be substituted by one or more further substituents selected from the group consisting of straight-chain or branched $C_1$-$C_5$-alkyl, in particular methyl, $C_1$-$C_5$-alkoxy, optionally substituted aryl and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen.

In particular, the substituents $R^3$ and $R^4$ can be identical or different and are each i-propyl, neopentyl, adamantyl, mesityl or 2,6-diisopropylphenyl.

Particularly preferred imidazoline or imidazolidine ligands have the following structures (III-a) to (III-o), where Ph is in each case a phenyl substituent, Bu is a butyl substituent, Mes is in each case a 2,4,6-trimethylphenyl substituent and (iPr)$_2$Ph is in all cases 2,6-diisopropylphenyl.

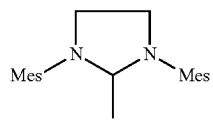

(III-a)

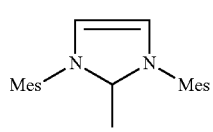

(III-b)

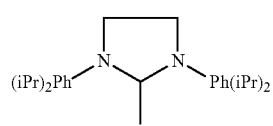

(III-c)

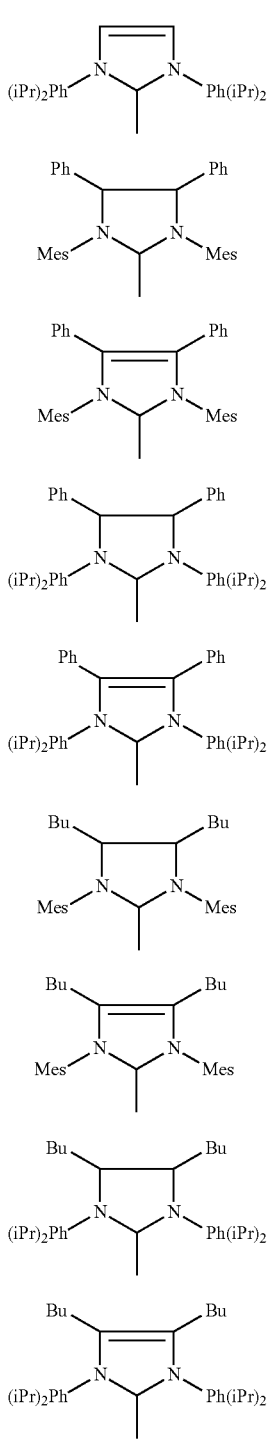

Definition of Preferred Catalysts:

A preferred catalyst has the general formula (I) in which
$X^1$ and $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or a weakly coordinating anion, one ligand of $L^1$, $L^2$, and (if u=1) $L^3$ has the general structure according to formulae (Ia) or (Ib), wherein
n is identical or different and represents an integer in the range of from 1 to 20,
D is identical or different and represents hydroxy, alkoxy, aryloxy, thiolate, thiol, thioether, selenol, selenoether, amine, phosphine, phosphate, phosphite, arsine, sulfoxide, sulfone, alkyl, phosphinimine, aminophosphine, carbene, selenoxide, imidazoline, imidazolidine, phosphine oxide, phosphine sulfide, phosphine selenide, ketone, ester, pyridyl, substituted pyridyl, or any other moiety able of acting as a two electron donor, with the remainder ligand(s) of $L^1$, $L^2$, and (if u=1) $L^3$ being (a) ligand/ligands different from the one of formulae (Ia) and (Ib) and $X^3$, u, t and t' having the meanings outlined for general formula (I).

A more preferred catalyst has the general formula (I) in which
$X^1$ and $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or a weakly coordinating anion, one ligand of $L^1$, $L^2$, and (if u=1) $L^3$ has the general structure according to formulae (Ia) or (Ib),
wherein
n is identical or different and represents an integer in the range of from 1 to 10,
D is identical or different and represents $C_1$-$C_{20}$-alkoxy, $C_6$-$C_{24}$-aryloxy or $C_1$-$C_{10}$-thioether, with the remainder ligand(s) of $L^1$, $L^2$, and (if u=1) $L^3$ being a ligand/ligands different from the one of formulae (Ia) and (Ib) and $X^3$, u, t and t' having the meanings outlined for general formula (I).

Another very preferred catalyst has the general formula (I) in which
$X^1$ and $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or a weakly coordinating anion, one ligand of $L^1$, $L^2$, and (if u=1) $L^3$ has the general structure according to formulae (a) or (Ib),
wherein
n is identical or different and represents an integer in the range of from 1 to 10,
D is identical or different and represents $C_1$-$C_{20}$-alkoxy, $C_6$-$C_{24}$-aryloxy or $C_1$-$C_{10}$-thioether, with the remainder ligand(s) of $L^1$, $L^2$, and (if u=1) $L^3$ being independently of one another, a $C_6$-$C_{24}$-arylphosphine, $C_1$-$C_{10}$-alkylphosphine or $C_3$-$C_{20}$-cycloalkylphosphine ligand, a sulfonated $C_6$-$C_{24}$-arylphosphine or sulfonated $C_1$-$C_{10}$-alkylphosphine ligand, a $C_6$-$C_{24}$-arylphosphinite or $C_1$-$C_{10}$-alkylphosphinite ligand, a $C_6$-$C_{24}$-arylphosphonite or $C_1$-$C_{10}$-alkylphosphonite ligand, a $C_6$-$C_{24}$-aryl phosphite or $C_1$-$C_{10}$-alkyl phosphite ligand, a $C_6$-$C_{24}$-arylarsine or $C_1$-$C_{10}$-alkylarsine ligand, a $C_6$-$C_{24}$-arylamine or $C_1$-$C_{10}$-alkylamine ligand, an optionally substituted pyridine ligand, a $C_6$-$C_{24}$-aryl sulfoxide or $C_1$-$C_{10}$-alkyl sulfoxide ligand, a $C_6$-$C_{24}$-aryloxy or $C_1$-$C_{10}$-alkyloxy ligand or a $C_6$-$C_{24}$-arylamide or $C_1$-$C_{10}$-alkylamide ligand, each of which may be substituted by a phenyl group which may in turn be substituted by a halogen-, $C_1$-$C_5$-alkyl or $C_1$-$C_5$-alkoxy-group, and $X^3$, u, t and t' having the meanings outlined for general formula (I).

An even more preferred catalyst has the general formula (I) in which
$X^1$ and $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or any weakly coordinating anion,
one ligand of $L^1$, $L^2$, and (if u=1) $L^3$ has the general structure according to formulae (Ia) or (Ib),
wherein
  n is identical or different and represents an integer in the range of from 1 to 5,
  D is identical or different and represents $C_1$-$C_{10}$ alkoxy or $C_6$-$C_{14}$ aryloxy,
with the remainder ligand(s) of $L^1$, $L^2$, and (if u=1) $L^3$ being a ligand/ligands different from the one of formulae (Ia) and (Ib), preferably selected from the group consisting of $PPh_3$, $P(p\text{-Tol})_3$, $P(o\text{-Tol})_3$, $PPh(CH_3)_2$, $P(CF_3)_3$, $P(p\text{-}FC_6H_4)_3$, $P(p\text{-}CF_3C_6H_4)_3$, $P(C_6H_4\text{—}SO_3Na)_3$, $P(CH_2C_6H_4\text{—}SO_3Na)_3$, $P(\text{isopropyl})_3$, $P(CHCH_3(CH_2CH_3))_3$, $P(\text{cyclopentyl})_3$, $P(\text{cyclohexyl})_3$, $P(\text{neopentyl})_3$ and $P(\text{benzyl})_3$, and $X^3$, u, t and t' having the meanings outlined for general formula (I).

A particularly preferred catalyst has the general formula (I) in which
$X^1$ and $X^2$ are different and hydride and halide, most preferably chloride,
one ligand of $L^1$, $L^2$, and (if u=1) $L^3$ has the general structure according to formulae (Ia) or (Ib),
wherein
  n is identical or different and represents an integer in the range of from 1 to 5,
  D is identical or different and represents $C_1$-$C_{10}$ alkoxy or $C_6$-$C_{14}$ aryloxy, with the remainder ligand(s) of $L^1$, $L^2$, and (if u=1) $L^3$ being a ligand/ligands different from the one of formulae (Ia) and (Ib), preferably selected from the group consisting of $PPh_3$, $P(p\text{-Tol})_3$, $P(o\text{-Tol})_3$, $PPh(CH_3)_2$, $P(CF_3)_3$, $P(p\text{-}FC_6H_4)_3$, $P(p\text{-}CF_3C_6H_4)_3$, $P(C_6H_4\text{—}SO_3Na)_3$, $P(CH_2C_6H_4\text{—}SO_3Na)_3$, $P(\text{isopropyl})_3$, $P(CHCH_3(CH_2CH_3))_3$, $P(\text{cyclopentyl})_3$, $P(\text{cyclohexyl})_3$, $P(\text{neopentyl})_3$ and $P(\text{benzyl})_3$, and $X^3$, u, t and t' having the meanings outlined for general formula (I).

Another particularly preferred catalyst has the general formula (I) in which
$X^1$ and $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or any weakly coordinating anion,
one ligand of $L^1$, $L^2$, and (if u=1) $L^3$ has the general structure according to formulae (Ia-1) or (Ib-1)

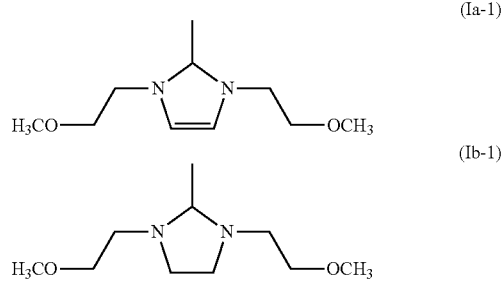

(Ia-1)

(Ib-1)

with the remainder ligand(s) of $L^1$, $L^2$, and (if u=1) $L^3$ being a ligand/ligands different from the one of formulae (Ia) and (Ib), preferably selected from the group consisting of $PPh_3$, $P(p\text{-Tol})_3$, $P(o\text{-Tol})_3$, $PPh(CH_3)_2$, $P(CF_3)_3$, $P(p\text{-}FC_6H_4)_3$, $P(p\text{-}CF_3C_6H_4)_3$, $P(C_6H_4\text{—}SO_3Na)_3$, $P(CH_2C_6H_4\text{—}SO_3Na)_3$, $P(\text{isopropyl})_3$, $P(CHCH_3(CH_2CH_3))_3$, $P(\text{cyclopentyl})_3$, $P(\text{cyclohexyl})_3$, $P(\text{neopentyl})_3$ and $P(\text{benzyl})_3$, and $X^3$, u, t and t' having the meanings outlined for general formula (I).

Another preferred catalyst has the general formula (I) in which
$X^1$ and $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or a weakly coordinating anion,
one ligand of $L^1$, $L^2$, and (if u=1) $L^3$ has the general structure according to general structure (Ic) or (Id) wherein
  n is identical or different and represents an integer in the range of from 1 to 20,
  R is identical or different and represents H, alkyl or aryl, and
  E is identical or different and represents a divalent moiety able of acting as a two electron donor selected from the group consisting of —O—, —S—, —Se—, —N(R)—, —P(R)—, —As(R)—, —S(=O)—, —PR(=S), —PR(=O)—, —C(=O)—, —C(=S)—, 2,6-pyridylene, substituted 2,6-pyridylene and any other divalent moiety able of acting as a two electron donor.
with the remainder ligand(s) of $L^1$, $L^2$, and (if u=1) $L^3$ being a ligand/ligands different therefrom, and $X^3$, u, t and t' having the meanings outlined for general formula (I).

Another more preferred catalyst has the general formula (I) in which
$X^1$ and $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or a weakly coordinating anion,
one ligand of $L^1$, $L^2$, and (if u=1) $L^3$ has the general structure according to general structure (Ic) or (Id) wherein
  n is identical or different and represents an integer in the range of from 1 to 10,
  R is identical or different and represents $C_1$-$C_{20}$-alkyl or $C_6$-$C_{14}$-aryl,
  E is identical or different and represents oxygen or sulfur, and
with the remainder ligand(s) of $L^1$, $L^2$, and (if u=1) $L^3$ being a ligand/ligands different therefrom and $X^3$, u, t and t' having the meanings outlined for general formula (I).

Another very preferred catalyst has the general formula (I) in which
$X^1$ and $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or a weakly coordinating anion,
one ligand of $L^1$, $L^2$, and (if u=1) $L^3$ has the general structure according to general structure (Ic) or (Id) wherein
  n is identical or different and represents an integer in the range of from 1 to 10,
  R is identical or different and represents $C_1$-$C_{20}$-alkyl or $C_6$-$C_{14}$-aryl, E is identical or different and represents oxygen or sulfur, and with the remainder ligand(s) of $L^1$, $L^2$, and (if u=1) $L^3$ being independently of one another, a $C_6$-$C_{24}$-arylphosphine, $C_1$-$C_{10}$-alkylphosphine or $C_3$-$C_{20}$-cycloalkylphosphine ligand, a sulfonated $C_6$-$C_{24}$-arylphosphine or sulfonated $C_1$-$C_{10}$-alkylphosphine ligand, a $C_6$-$C_{24}$-arylphosphinite or $C_1$-$C_{10}$-alkylphosphinite ligand, a $C_6$-$C_{24}$-arylphosphonite or $C_1$-$C_{10}$-alkylphosphonite ligand, a $C_6$-$C_{24}$-aryl phosphite or $C_1$-$C_{10}$-alkyl phosphite ligand, a $C_6$-$C_{24}$-arylarsine or $C_1$-$C_{10}$-alkylarsine ligand, a $C_6$-$C_{24}$-arylamine or $C_1$-$C_{10}$-alkylamine ligand, an optionally substituted pyridine ligand, a $C_6$-$C_{24}$-aryl sulfoxide or $C_1$-$C_{10}$-alkyl sulfoxide ligand, a $C_6$-$C_{24}$-aryloxy or $C_1$-$C_{10}$-alkyloxy ligand or a $C_6$-$C_{24}$-arylamide or $C_1$-$C_{10}$-alkylamide ligand, each of which may be substituted by a phenyl group which may in turn be substituted by a halogen-, $C_1$-$C_5$-alkyl or $C_1$-$C_5$-alkoxygroup, and $X^3$, u, t and t' having the meanings outlined for general formula (I).

Another even more preferred catalyst has the general formula (I) in which $X^1$ and $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or a weakly anionic coordinating or non-coordinating anion, one ligand of $L^1$, $L^2$, and (if u=1) $L^3$ has the general structure according to general structure (Ic) or (Id) wherein
n is identical or different and represents an integer in the range of from 1 to 5,
R is identical or different and represents $C_1$-$C_{10}$ alkyl or $C_6$-$C_{14}$ aryl,
E is identical or different and represents oxygen, sulfur, and with the remainder ligand(s) of $L^1$, $L^2$, and (if u=1) $L^3$ being a ligand/ligands different therefrom, preferably selected from the group consisting of $PPh_3$, $P(p\text{-}Tol)_3$, $P(o\text{-}Tol)_3$, $PPh(CH_3)_2$, $P(CF_3)_3$, $P(p\text{-}FC_6H_4)_3$, $P(p\text{-}CF_3C_6H_4)_3$, $P(C_6H_4\text{—}SO_3Na)_3$, $P(CH_2C_6H_4\text{—}SO_3Na)_3$, $P(isopropyl)_3$, $P(CHCH_3(CH_2CH_3))_3$, $P(cyclopentyl)_3$, $P(cyclohexyl)_3$, $P(neopentyl)_3$ and $P(benzyl)_3$, and $X^3$, u, t and t' having the meanings outlined for general formula (I).

A particularly preferred catalyst has the general formula (I) in which $X^1$ and $X^2$ are different and hydride and halide, most preferably chloride, one ligand of $L^1$, $L^2$, and (if u=1) $L^3$ has the general structure according to general structure (Ic) or (Id) wherein
n is identical or different and represents an integer in the range of from 1 to 5,
R is identical or different and represents $C_1$-$C_{10}$ alkyl or $C_6$-$C_{14}$ aryl,
E is identical or different and represents oxygen, sulfur, and with the remainder ligand(s) of $L^1$, $L^2$, and (if u=1) $L^3$ being a ligand/ligands different therefrom, preferably selected from the group consisting of $PPh_3$, $P(p\text{-}Tol)_3$, $P(o\text{-}Tol)_3$, $PPh(CH_3)_2$, $P(CF_3)_3$, $P(p\text{-}FC_6H_4)_3$, $P(p\text{-}CF_3CH_4)_3$, $P(C_6H_4\text{—}SO_3Na)_3$, $P(CH_2C_6H_4\text{—}SO_3Na)_3$, $P(isopropyl)_3$, $P(CHCH_3(CH_2CH_3))_3$, $P(cyclopentyl)_3$, $P(cyclohexyl)_3$, $P(neopentyl)_3$ and $P(benzyl)_3$, and $X^3$, u, t and t' having the meanings outlined for general formula (I).

Another particularly preferred catalyst has the general formula (I) in which $X^1$ and $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or a weakly anionic coordinating or non-coordinating anion, one ligand of $L^1$, $L^2$, and (if u=1) $L^3$ has the general structure according formula (Ic-1)

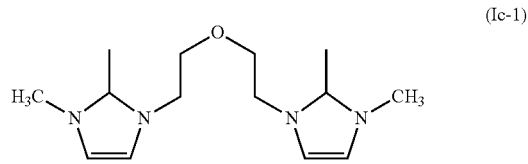

(Ic-1)

with the remainder ligand(s) of $L^1$, $L^2$, and (if u=1) $L^3$ being a ligand/ligands different therefrom, preferably selected from the group consisting of $PPh_3$, $P(p\text{-}Tol)_3$, $P(o\text{-}Tol)_3$, $PPh(CH_3)_2$, $P(CF_3)_3$, $P(p\text{-}FC_6H_4)$, $P(p\text{-}CF_3C_6H_4)$, $P(C_6H_4\text{—}SO_3Na)_3$, $P(CH_2C_6H_4\text{—}SO_3Na)_3$, $P(isopropyl)_3$, $P(CHCH_3(CH_2CH_3))_3$, $P(cyclopentyl)_3$, $P(cyclohexyl)_3$, $P(neopentyl)_3$ and $P(benzyl)_3$, and $X^3$, u, t and t' having the meanings outlined for general formula (I).

The present invention provides catalysts of the above general formula (I) as well as all preferred, more preferred and most preferred structures thereof also shown above with the following three alternatives: (i) with u=0 and at the same time t=1, or (ii) with u=1 and at the same time t=0, or (iii) with u=1 and at the same time t=1.

In order to prepare the catalysts according to general formula (I) and all preferred, more preferred and most preferred catalysts a person skilled in the art can use multistep procedures as outlined and exemplified in the experimental section of this application for various catalysts and can apply, generalize and modify to the extent necessary such described procedures to prepare catalysts falling under general formula (I). The preparation methods typically include schlenk or glovebox techniques. The characterization of the catalysts, substrates and compounds e.g. by $^1$H-, $^{13}$C-, $^{19}$F-, $^{31}$P-, or $^{11}$B-NMR, elemental analysis, and ESI-MS as outlined in the experimental section of this application are routine to a person skilled in the art of synthetic chemistry.

The present invention further relates to a process of hydrogenating substrates possessing at least one carbon-carbon double bond comprising subjecting said substrate to a hydrogenation reaction in the presence of a catalyst according to general formula (I).

Substrates to be Hydrogenated:

The process of the present invention is broadly applicable to the hydrogenation of a variety of substrates, including terminal olefins, internal olefins, cyclic olefins, conjugated olefins, and any further olefins having at least one carbon-carbon double bond and additionally at least one further polar unsaturated double or triple bond. The process is also applicable to the hydrogenation of polymers having carbon-carbon double bonds. Such polymers may represent homo-, co- or terpolymers.

As a terminal olefin or alkene, it is possible to hydrogenate a hydrocarbon compound with a terminal unsaturated carbon-carbon double bond having the general formula $C_nH_{2n}$. The terminal olefin can be a straight-chain or a branched hydrocarbon compound of any length, preferably 1-hexene.

As an internal olefin or alkene, it is possible to hydrogenate a hydrocarbon compound with an internal unsaturated carbon-carbon double bond having the general formula $C_nH_{2n}$. The internal olefin can be a straight-chain or a branched hydrocarbon of any length, preferably 2-hexene.

As a cyclic olefin or cycloalkene, it is possible to hydrogenate a hydrocarbon compound with a cyclic unsaturated carbon-carbon double bond having the general formula $C_nH_{2n-2}$. The cyclic olefin can be a ring of any size, preferably cyclohexene.

As a conjugated olefin or dialkene, it is possible to hydrogenate a hydrocarbon compound with conjugated carbon-carbon unsaturated double bonds. The conjugation can be a straight-chain or a branched hydrocarbon of any length, preferably styrene.

As an olefin, it is also possible to selectively hydrogenate a hydrocarbon compound with at least one unsaturated carbon-carbon double bond and least one other unsaturated polar double or triple bond. Such unsaturated polar bonds are surprisingly left unaltered. The carbon-carbon double bond in such olefins can be of any nature including terminal, internal, cyclic and conjugated ones. The additional unsaturated polar bond can be of any nature with preference given to carbon-nitrogen, carbon-phosphorus, carbon-oxygen, and carbon-sulfur unsaturated polar bonds.

Polymers having carbon-carbon double bonds may also be subjected to the inventive process. Such polymers preferably comprise repeating units based on at least one conjugated diene monomer.

The conjugated diene can be of any nature. In one embodiment ($C_4$-$C_6$) conjugated dienes are used. Preference is given to 1,3-butadiene, isoprene, 1-methylbutadiene, 2,3-dimethylbutadiene, piperylene, chloroprene, or mixtures thereof. More preference is given to 1,3-butadiene, isoprene or mixtures thereof. Particular preference is given to 1,3-butadiene.

In a further embodiment polymers having carbon-carbon double bonds may be subjected to the inventive process which comprise repeating units of not only at least one conjugated diene as monomer (a) but additionally at least one further copolymerizable monomer (b).

Examples of suitable monomers (b) are olefins, such as ethylene or propylene.

Further examples of suitable monomers (b) are vinylaromatic monomers, such as styrene, alpha-methyl styrene, o-chlorostyrene or vinyltoluenes, vinylesters of aliphatic or branched $C_1$-$C_{18}$ monocarboxylic acids, such as vinyl acetate, vinyl propionate, vinyl butyrate, vinyl valerate, vinyl hexanoate, vinyl 2-ethylhexanoate, vinyl decanoate, vinyl laurate and vinyl stearate.

A preferred polymer to be used in the present invention is a copolymer of 1,3-butadiene and styrene or alpha-methylstyrene. Said copolymers may have a random or block type structure.

Further examples of suitable monomers (b) are esters of ethylenically unsaturated monocarboxylic acids or mono- or diesters of dicarboxylic acids with generally $C_1$-$C_{12}$ alkanols, e.g. esters of acrylic acid, methacrylic acid, maleic acid, fumaric acid and itaconic acid with e.g. methanol, ethanol, n-propanol, isopropanol, 1-butanol, 2-butanol, isobutanol, tert.-butanol, n-hexanol, 2-ethylhexanol, or $C_5$-$C_{10}$-cycloalkanols, such as cyclopentanol or cyclohexanol, and of these preferably the esters of acrylic and/or methacrylic acid, examples being methyl methacrylate, n-butyl methacrylate, tert-butyl methacrylate, n-butyl acrylate, tert-butyl acrylate, and 2-ethylhexyl acrylate.

The inventive process may be further used to hydrogenate so-called nitrile rubbers. Nitrile rubbers ("NBR") represent copolymers or terpolymers containing repeating units of at least one conjugated diene, at least one α,β-unsaturated nitrile monomer and, if appropriate, one or more further copolymerizable monomers.

The conjugated diene in such nitrile rubbers can be of any nature. Preference is given to using ($C_4$-$C_6$)-conjugated dienes. Particular preference is given to 1,3-butadiene, isoprene, 2,3-dimethylbutadiene, piperylene or mixtures thereof. In particular, use is preferably made of 1,3-butadiene or isoprene or mixtures thereof. Very particular preference is given to 1,3-butadiene.

As α,β-unsaturated nitrile monomer, it is possible to use any known α,β-unsaturated nitrile, with preference being given to ($C_3$-$C_5$)-α,β-unsaturated nitriles such as acrylonitrile, methacrylonitrile, ethacrylonitrile or mixtures thereof. Particularly preference is given to acrylonitrile.

A particularly preferred nitrile rubber to be subjected to hydrogenation according to the invention is thus a copolymer of acrylonitrile and 1,3-butadiene.

In addition to the conjugated diene and the α,β-unsaturated nitrile, it is possible to use one or more further copolymerizable monomers known to those skilled in the art, e.g. termonomers containing carboxyl groups, like α,β-unsaturated monocarboxylic acids, their esters or amides, α,β-unsaturated dicarboxylic acids, their monoesters or diesters, or their corresponding anhydrides or amides.

As α,β-unsaturated monocarboxylic acids it is possible to use acrylic acid and methacrylic acid.

It is also possible to employ esters of the α,β-unsaturated monocarboxylic acids, preferably their alkyl esters and alkoxyalkyl esters. Preference is given to the alkyl esters, especially $C_1$-$C_{18}$ alkyl esters, of the α,β-unsaturated monocarboxylic acids, Particular preference is given to alkyl esters, especially $C_1$-$C_{18}$ alkyl esters, of acrylic acid or of methacrylic acid, more particularly methyl acrylate, ethyl acrylate, propyl acrylate, n-butyl acrylate, tert-butyl acrylate, 2-ethylhexyl acrylate, n-dodecyl acrylate, methyl methacrylate, ethyl methacrylates, butyl methacrylate and 2-ethylhexyl methacrylate. Also preferred are alkoxyalkyl esters of the α,β-unsaturated monocarboxylic acids, more preferably alkoxyalkyl esters of acrylic acid or of methacrylic acid, more particular $C_2$-$C_{12}$ alkoxyalkyl esters of acrylic acid or of methacrylic acid, very preferably methoxymethyl acrylate, methoxyethyl (meth)acrylate, ethoxyethyl (meth) acrylate and methoxyethyl (meth)acrylate. Use may also be made of mixtures of alkyl esters, such as those mentioned above, for example, with alkoxyalkyl esters, in the form of those mentioned above, for example. Use may also be made of cyanoalkyl acrylate and cyanoalkyl methacrylates in which the C atom number of the cyanoalkyl group is 2-12, preferably α-cyanoethyl acrylate, β-cyanoethyl acrylate and cyanobutyl methacrylate. Use may also be made of hydroxyalkyl acrylates and hydroxyalkyl methacrylate in which the C atom number of the hydroxyalkyl groups is 1-12, preferably 2-hydroxyethyl acrylate, 2-hydroxyethyl methacrylate and 3-hydroxypropyl acrylate; use may also be made of fluorine-substituted benzyl-group-containing acrylates or methacrylates, preferably fluorobenzyl acrylate, and fluorobenzyl methacrylate. Use may also be made of acrylates and methacrylates containing fluoroalkyl groups, preferably trifluoroethyl acrylate and tetrafluoropropyl methacrylate.

Use may also be made of α,β-unsaturated carboxylic esters containing amino groups, such as dimethylaminomethyl acrylate and diethylaminoethyl acrylate.

As copolymerizable monomers it is possible, furthermore, to use α,β-unsaturated dicarboxylic acids, preferably maleic acid, fumaric acid, crotonic acid, itaconic acid, citraconic acid and mesaconic acid. Use may be made, furthermore, of α,β-unsaturated dicarboxylic anhydrides, preferably maleic anhydride, itaconic anhydride, citraconic anhydride and mesaconic anhydride.

It is possible, furthermore, to use monoesters or diesters of α,β-unsaturated dicarboxylic acids.

These α,β-unsaturated dicarboxylic monoesters or diesters may be, for example, alkyl esters, preferably $C_1$-$C_{10}$ alkyl, more particularly ethyl, n-propyl, isopropyl, n-butyl, tert-butyl, n-pentyl or n-hexyl esters, alkoxyalkyl esters, preferably $C_2$-$C_{12}$ alkoxyalkyl, more preferably $C_3$-$C_8$-alkoxyalkyl, hydroxyalkyl, preferably $C_1$-$C_{12}$ hydroxyalkyl, more preferably $C_2$-$C_8$ hydroxyalkyl, cycloalkyl esters, preferably $C_5$-$C_{12}$ cycloalkyl, more preferably $C_6$-$C_{12}$ cycloalkyl, alkylcycloalkyl esters, preferably $C_6$-$C_{12}$ alkylcycloalkyl, more preferably $C_7$-$C_{10}$ alkylcycloalkyl, aryl esters, preferably $C_6$-$C_{14}$ aryl esters, these esters being monoesters or diesters, and it also being possible, in the case of the diesters, for the esters to be mixed esters.

Particularly preferred alkyl esters of α,β-unsaturated monocarboxylic acids are methyl (meth)acrylate, ethyl (meth)acrylate, propyl (meth)acrylate, n-butyl (meth)acrylate, t-butyl (meth)acrylate, hexyl (meth)acrylate, 2-ethylhexyl (meth)acrylate, octyl (meth)acrylate, 2-propylheptyl acrylate and lauryl (meth)acrylate. More particularly, n-butyl acrylate is used.

Particularly preferred alkoxyalkyl esters of the α,β-unsaturated monocarboxylic acids are methoxyethyl (meth)acrylate, ethoxyethyl (meth)acrylate and methoxyethyl (meth)acrylate. More particularly, methoxyethyl acrylate is used.

Particularly preferred hydroxyalkyl esters of the α,β-unsaturated monocarboxylic acids are hydroxyethyl (meth)acrylate, hydroxypropyl (meth)acrylate and hydroxybutyl (meth)acrylate.

Other esters of the α,β-unsaturated monocarboxylic acids that are used are additionally, for example, polyethylene glycol (meth)acrylate, polypropylene glycol (meth)acrylate, glycidyl (meth)acrylate, epoxy (meth)acrylate, N-(2-hydroxyethyl)acrylamides, N-(2-hydroxymethyl)acrylamides and urethane (meth)acrylate.

Examples of α,β-unsaturated dicarboxylic monoesters encompass maleic acid monoalkyl esters, preferably monomethyl maleate, monoethyl maleate, monopropyl maleate and mono-n-butyl maleate;

maleic acid monocycloalkyl esters, preferably monocyclopentyl maleate, monocyclohexyl maleate and monocycloheptyl maleate;

maleic acid monoalkyl cycloalkyl esters, preferably monomethyl cyclopentyl maleate and monoethyl cyclohexyl maleate;

maleic acid monoaryl esters, preferably monophenyl maleate;

maleic acid monobenzyl esters, preferably monobenzyl maleate;

fumaric acid monoalkyl esters, preferably monomethyl fumarate, monoethyl fumarate, monopropyl fumarate and mono-n-butyl fumarate;

fumaric acid monocycloalkyl esters, preferably monocyclopentyl fumarate, monocyclohexyl fumarate and monocycloheptyl fumarate;

fumaric acid monoalkyl cycloalkyl esters, preferably monomethyl cyclopentyl fumarate and monoethyl cyclohexyl fumarate;

fumaric acid monoaryl esters, preferably monophenyl fumarate;

fumaric acid monobenzyl esters, preferably monobenzyl fumarate;

citraconic acid monoalkyl esters, preferably monomethyl citraconate, monoethyl citraconate, monopropyl citraconate and mono-n-butyl citraconate;

citraconic acid monocycloalkyl esters, preferably monocyclopentyl citraconate, monocyclohexyl citraconate and monocycloheptyl citraconate;

citraconic acid monoalkyl cycloalkyl esters, preferably monomethyl cyclopentyl citraconate and monoethyl cyclohexyl citraconate;

citraconic acid monoaryl esters, preferably monophenyl citraconate;

citraconic acid monobenzyl esters, preferably monobenzyl citraconate;

itaconic acid monoalkyl esters, preferably monomethyl itaconate, monoethyl itaconate, monopropyl itaconate and mono-n-butyl itaconate;

itaconic acid monocycloalkyl esters, preferably monocyclopentyl itaconate, monocyclohexyl itaconate and monocycloheptyl itaconate;

itaconic acid monoalkyl cycloalkyl esters, preferably monomethyl cyclopentyl itaconate and monoethyl cyclohexyl itaconate;

itaconic acid monoaryl esters, preferably monophenyl itaconate;

itaconic acid monobenzyl esters, preferably monobenzyl itaconate.

Mesaconic acid monoalkyl esters, preferably mesaconic acid monoethyl esters;

As α,β-unsaturated dicarboxylic diesters it is possible to use the analogous diesters based on the abovementioned monoester groups, and the ester groups may also be chemically different groups.

Preferably the substrate to be hydrogenated is a nitrile rubber comprising repeating units of at least one conjugated diene, at least one α,β-unsaturated nitrile and, if appropriate, one or more further copolymerizable monomers, preferably a nitrile rubber comprising repeating units of at least one conjugated diene selected from the group consisting of 1,3-butadiene, isoprene, 2,3-dimethylbutadiene, piperylene and mixtures thereof, at least one α,β-unsaturated nitrile selected from the group consisting of acrylonitrile, methacrylonitrile, ethacrylonitrile and mixtures thereof, and optionally of one or more further copolymerizable monomers selected from the group consisting of α,β-unsaturated monocarboxylic, dicarboxylic acids, their esters or amides.

The proportions of conjugated diene and α,β-unsaturated nitrile monomer in the NBR polymers to be used can vary within wide ranges. The proportion of the conjugated diene or the sum of conjugated dienes is usually in the range from 40 to 90% by weight, preferably in the range from 50 to 85% by weight, based on the total polymer. The proportion of the α,β-unsaturated nitrile or the sum of the α,β-unsaturated nitriles is usually from 10 to 60% by weight, preferably from 15 to 50% by weight, based on the total polymer. The proportions of the monomers in each case add up to 100% by weight. The additional monomers can be present in amounts of from 0 to 40% by weight, preferably from 0.1 to 40% by weight, particularly preferably from 1 to 30% by weight, based on the total polymer. In this case, corresponding proportions of the conjugated diene or dienes and/or the α,β-unsaturated nitrile or nitriles are replaced by the proportions of the additional monomers, with the proportions of all monomers in each case adding up to 100% by weight.

The preparation of such nitrile rubbers by polymerization of the abovementioned monomers is adequately known to those skilled in the art and is comprehensively described in the literature.

Nitrile rubbers which can be used for the purposes of the invention are commercially available, e.g. as products marketed under the trademarks Perbunan® and Krynac® by Lanxess Deutschland GmbH. The nitrile rubbers which can be used for the hydrogenation have a Mooney viscosity (ML 1+4 at 100° C.) in the range from 30 to 70, preferably from 30 to 50. This corresponds to a weight average molecular weight $M_w$ in the range 150 000-500 000, preferably in the range 180 000-400 000. The nitrile rubbers used typically have a polydispersity PDI $M_w/M_n$ ($M_n$ is the number average molecular weight) in the range of 2.0-6.0 and preferably in the range 2.0-4.0.

Hydrogenated nitrile rubbers obtained pursuant to this invention can have a Mooney viscosity (ML 1+4 at 100° C.) in the range of greater than 0 up to 150, typically the Mooney viscosity lies in the range of from 5 to 150, preferably of from 10 to 120, more preferably of from 30 to 110, even more preferably of from 35 to 100, and particularly preferably of from 50 to 100 and most preferably of from 60 to 90. The determination of the Mooney viscosity is carried out in accordance with ASTM standard D 1646.

They typically have a polydispersity PDI=$M_w/M_n$, where $M_w$ is the weight average molecular weight and $M_n$ is the number average molecular weight, in the range of 1.5 to 6 and preferably in the range of 1.8 to 4

Hydrogenation Conditions:

The process of the present invention is generally carried out at a temperature in the range from 0° C. to 200° C., preferably in the range from 15° C. to 150° C. This means that the process may be carried out at mild conditions. In case low molecular weight olefins like terminal olefins, internal olefins, cyclic olefins, conjugated olefins, or any other olefins having at least one carbon-carbon double bond and additionally at least one further polar unsaturated double bond are subjected to hydrogenation, the temperature typically lies in the range from 20 to 100° C. In case polymers with double bonds in the polymer backbone are used as substrates the hydrogenation temperature typically lies in a range from 40 to 200° C., preferably in the range from 70 to 150° C. The hydrogenation process of the present invention is preferably carried out with hydrogen gas at a pressure from 0.1 to 20 MPa, preferably at a pressure from 1 to 16 MPa. In one embodiment of the present process said hydrogen gas is essentially pure.

Preferably the hydrogenation process is carried out at a temperature in the range from 0° C. to 200° C. with hydrogen gas at a pressure from 0.1 to 20 MPa, preferably at a temperature in the range from 15° C. to 150° C. with hydrogen gas at a pressure from 1 to 16 MPa.

The amount of catalyst according to general formula (I) can vary in a broad range. Typically the catalyst according to general formula (I) is used in a molar ratio from (0.01-0.20): 1, preferably from (0.01-0.05): 1 based on the substrate to be hydrogenated.

In the hydrogenation of rubber polymers the amount of catalyst according to formula (I) may also vary in a broad range. The amount of catalyst is then calculated on a weight base ratio in "phr" (parts per hundred rubber). Typically 0.005 phr to 2.5 phr catalyst are used based on the rubber. Preferably 0.01 phr to 2 phr and more preferably 0.025 phr to 2 phr catalyst are used based on the rubber.

The hydrogenation can be carried out in a suitable solvent which does not deactivate the catalyst used and also does not adversely affect the reaction in any other way. Preferred solvents include but are not restricted to methanol, chlorobenzene, bromobenzene, dichloromethane, benzene, toluene, methyl ethyl ketone, acetone, tetrahydrofuran, tetrahydropyran, dioxane and cyclohexane. The particularly preferred solvent is chlorobenzene. In some cases, when the substrate to be hydrogenated itself can function as solvent, e.g. in the case of 1-hexene, the addition of a further additional solvent can also be omitted.

According to the present invention the catalyst can be introduced into the polymer by any possible means, such as e.g. mechanical mixing, preferably by using a procedure which can result in a homogeneous distribution of the catalyst and polymer.

In one embodiment of the present invention the catalyst according to formula (I) is contacted with the substrate to be hydrogenated by adding the catalyst or catalyst solution to a substrate solution and mixing until an efficient distribution and dissolution of the catalyst has taken place.

The present process can be performed in the presence or absence of any further co-catalyst or other additives. It is not necessary to add such further co-catalyst or other additives. This applies in particular to co-catalysts which are typically used e.g. in combination with other hydrogenation catalysts known from prior art like the Wilkinson's catalyst. In one embodiment of the present invention the process is conducted in the presence or absence of co-catalysts having the formula $R^1_m Z$, wherein $R^1$ are identical or different and are each a $C_1$-$C_8$-alkyl group, a $C_4$-$C_8$-cycloalkyl group, a $C_6$-$C_{15}$-aryl group or a $C_7$-$C_{15}$-aralkyl group, Z is phosphorus, arsenic, sulphur or a sulphoxide group S=O, preferably phosphorus, and m is 2 or 3, preferably 3. In a further embodiment the present process is conducted in the presence or absence of triphenylphosphine.

The hydrogenation process of the present invention can be undertaken in a suitable reactor equipped with temperature regulating and agitating means. It is possible to perform the process either batch-wise or continuously.

During the course of the hydrogenation reaction of the present invention, the hydrogen is added to the reactor. The reaction time is typically from about one quarter of an hour to about 100 hours, depending on operational conditions. As the novel catalysts are robust, it is not necessary to use a special gas dryer to dry the hydrogen.

According to the present invention, when the hydrogenation reaction is complete, to the extent desired, the reaction vessel can be cooled (if applicable) and vented and the hydrogenated substrate can be isolated by conventional methods well known to any artisan.

During the process according to the invention it may happen that a hydrogenation reaction and a metathesis reaction occur simultaneously. In case polymeric substrates and in particular nitrile rubbers are used as substrates in the process according to the invention, such metathesis reaction results in a decrease of the molecular weight of the substrate.

EXAMPLES

In the following IMes$_2$ is used as an abbreviation of a 1,3-bis(2,4,6-trimethylphenyl) imidazoline ligand, SIMes$_2$ is used as an abbreviation of a 1,3-bis(2,4,6-trimethylphenyl)-2-imidazolidine ligand and Im is used as an abbreviation for imidazole.

General Procedures:

Manipulations were done using standard Schlenk and glovebox techniques ($O_2$ level <0.1 ppm; $N_2$ as inert gas), unless noted differently. Solvents, namely $CH_2Cl_2$, $Et_2O$, THF, toluene, and hexane, were used in dried form and stored under $N_2$. $RuHCl(PPh_3)_3$ was prepared according to a modified literature procedure (J. Mol. Catal. A: Chem. 2006, 259, 17-23) where EtOH was replaced with sec-BuOH.

A Synthesis of Ligands and Catalysts

A.1 Synthesis of $[(CH_3OCH_2CH_2)_2Im]Cl$ (1)

Chloromethylethylether (5.0 mL, 54.9 mmol) was added to a solution of trimethylsilylimidazole (2.229 g, 15.892 mmol) in toluene (5 mL). The mixture was refluxed in the dark for 72 h during which two layers formed. The top layer was syringed off and discarded. To the viscous bottom layer was added methylene chloride (10 mL) and pentane (20 mL). This mixture was stirred and the top layer was syringed off. The remaining colorless oil was dried in vacuum (3.489 g, 99%) resulting in the following analytical data:

$^1$H NMR ($CD_2Cl_2$, 5.32 ppm). 3.31 (s, 6H, 2×OMe), 3.73 (t, 4H, 2×$CH_2$), 4.53 (t, 4H, 2×$CH_2$), 7.59 (s, 2H, 2×CH), 10.47 (s, 1H, NCHN).

$^{13}$C NMR ($CD_2Cl_2$, 53.5 ppm): 49.49 (2×OMe), 58.65 (2×$CH_2$), 70.23 (2×$CH_2$), 122.49 (2×CH), 137.71 (NCHN).

A.2 Synthesis of $AgCl[(CH_3OCH_2CH_2)_2Im]$ (2)

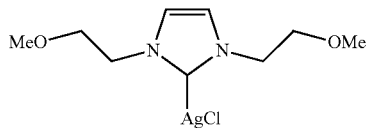

$Ag_2O$ (0.338 g, 1.46 mmol) in methylene chloride (5 mL) was added to a solution of $[(CH_3OCH_2CH_2)_2Im]Cl$ (1) in methylene chloride (5 mL). The slurry was stirred in the dark for 16 h. The excess $Ag_2O$ was filtered off through celite and the resulting colorless solution was concentrated to approximately to 2 mL and 15 mL of pentane were added causing a white precipitate to form. The solid settles and the colorless solution was syringed off. The white solid was dried in vacuum (0.301 g, 88%) resulting in the following analytical data:

$^1$H NMR ($CD_2Cl_2$, 5.32 ppm): 3.32 (s, 6H, 2×OMe), 3.67 (t, 4H, 2×$CH_2$), 4.25 (t, 4H, 2×$CH_2$), 7.10 (s, 2H, 2×CH).

$^{13}$C NMR (53.8 ppm): 52.3 (2×OMe), 59.1 (2×$CH_2$), 72.4 (2×$CH_2$), 122.2 (CH), 179.8 (NCN). Anal. Calcd for $C_9H_{16}AgClN_2O_2$ (327.56): C, 33.00; H, 4.92; N, 8.55. Found: C, 33.15; H, 4.68; N, 8.91.

ESI-MS: 475 [M-$AgCl_2$]+.

A.3 Synthesis of $RuHCl(PPh_3)_2[(CH_3OCH_2CH_2)_2I]$ (3)

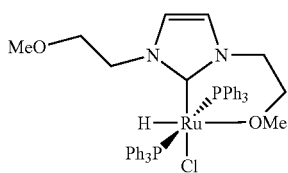

$AgCl[(CH_3OCHCH_2)_2Im]$ (2) (0.128 g, 0.391 g) and $RuHCl(PPh_3)_3$ (0.306 g, 0.331 mmol) were combined and toluene (15 mL) was added producing a color change from purple to red. The suspension was stirred for 16 h at room temperature. The mixture was filtered through a plug of celite and the red filtrate was concentrated to 5 mL. The addition of pentane caused a yellow precipitate to form that was collected by filtration. This solid was washed with pentane and dried on high vacuum. The solid was dissolved in a methylene chloride (5 mL), diethyl ether (15 mL). Upon sitting colorless crystals of $AgCl(PPh_3)$ deposited which were filtered off. The remaining filtrate was concentrated to dryness to give pure product (0.230 g, 82%) resulting in the following analytical data:

$^1$H NMR ($C_6D_6$): −23.54 (t, J=24.11 Hz, 1H, RuH), 2.22 (m, 2H, $CH_2$), 2.67 (s, 3H, $OCH_3$), 2.86 (m, 2H, $CH_2$), 2.91 (s, 3H, $OCH_3$), 2.99 (m, 2H, $CH_2$), 3.06 (m, 2H, $CH_2$), 5.95 (s, 1H, CH, Im), 6.34 (m, 1H, CH, Im), 7.04 (m, 1H, CH, Im), 7.04-7.12 (m, 18H, 2×$PPh_3$), 7.80-7.88 (m, 12 H, 2×$PPh_3$).

$^{13}$C NMR: 48.57 ($CH_2$), 50.32 ($CH_2$), 57.63 ($OCH_3$), 59.51 ($OCH_3$), 70.17 ($CH_2$), 72.65 ($CH_2$), 120.13 (CH, Im), 120.17 (CH, Im), 134.24 (d, J=19.5 Hz, ipso-C, $PPh_3$), 135.02 (t, J=5.8 Hz, $PPh_3$), 139.37 (t, J=16.5 Hz, $PPh_3$), quaternary NCN carbon not observed.

$^{31}$P NMR: 44.54 ($PPh_3$), 44.67 ($PPh_3$).

Anal. Calcd for $C_{45}H_{48}ClN_2O_2P_2Ru$ (847.35): C, 63.86; H, 5.60; N, 3.31. Found: C, 63.43; H, 5.84; N, 3.42.

A.4 Synthesis of $RuHCl(PPh_3)(CH_3OCH_2CH_2)_2Im)$ ($SIMes_2$) (4)

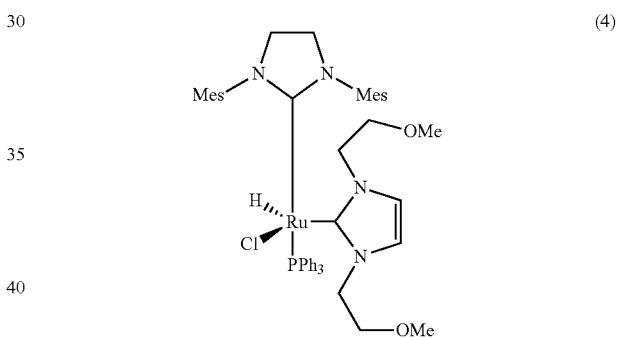

$RuHCl(PPh_3)_2[(CH_3OCH_2CH_2)_2Im]$ (3) (1.581 g, 1.868 mmol) and $SIMes_2$ (1.041 g, 3.397 mmol) were combined. Tetrahydrofuran (30 mL) was added and the mixture was heated at 60° C. for 24 h. All volatiles were removed in vacuum. The oily solid was dissolved in toluene (5 mL) and the solution was filtered through neutral alumina. To the red solution was added pentane (15 mL). The solution was allowed to rest for 24 h during which time red crystals formed (1.157 g, 70%) resulting in the following analytical data:

$^1$H NMR ($CD_2Cl_2$): −28.87 (d, J=27.0 Hz, 1H, RuH), 1.71 (br. s, 3H, $CH_3$, Mes), 2.04-2.12 (m, 1H, $CH_2$), 2.25 (br. s, 3H, $CH_3$, Mes), 2.37-2.75 (m, 18H), 2.87 (s, 3H, $OCH_3$), 2.88-2.94 (m, 1H, $CH_2$), 3.12 (s, 3H, $OCH_3$), 3.57-3.64 (m, 1H, $CH_2$), 3.68-3.89 (m, 4H, $NCH_2CH_2N$), 3.92-3.99 (m, 1H, $CH_2$), 6.56 (d, J=2.2 Hz, 1H, Im), 6.61-6.71 (m, 2H, 2×CH, Im, Mes), 6.88 (br. s, 1H, CH, Mes), 6.98-7.05 (m, 13 H, $PPh_3$, 13 CH, o-H and m-H, $PPh_3$ and CH, Mes), 7.12-7.18 (m, 3H, p-H, $PPh_3$).

$^{13}$C NMR ($CD_2Cl_2$): 16.85 ($CH_3$, Mes, o-H), 20.83 ($CH_3$ Mes, p-H), 46.33 ($CH_2$), 47.79 (2×$CH_2$), 51.33 (d, $^4J_{C-P}$, $NCH_2CH_2N$), 57.52 ($OCH_3$), 58.19 ($OCH_3$), 70.82 ($CH_2$), 71.56 ($CH_2$), 118.52 (CH, Im), 119.43 (CH, Im), 127.18 (d, J=8.1 Hz, m-C, $PPh_3$), 127.86 (J=1.6 Hz, $PPh_3$, p-C, $PPh_3$), 134.05 (d, J=10.9 Hz, o-C, PPh$_3$), 140.26 (d, J=29.3 Hz, PPh$_3$, ipso-C, PPh$_3$), 189.02 (NCN) 227.56 (d, J=60 Hz, NCN).

$^{31}$P NMR: 42.33 (d, J=23.3 Hz).

Anal. Calcd for C$_{48}$H$_{58}$ClN$_4$O$_2$PRu (890.50): C, 64.74; H, 6.56; N, 6.29. Found: C, 64.73; H, 7.13; N, 6.42.

A.5 Synthesis of [(O(CH$_2$CH$_2$ImCH$_3$)$_2$]Br$_2$ (5)

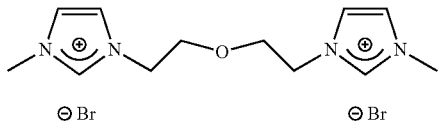

Bis(2-bromoethyl)ether (7.125 g, 30.72 mmol) was added to a solution of methylimidazole (6.025 g, 73.37 mmol) in toluene (30 mL). The mixture was heated to 90° C. for 48 h during which time a bottom light yellow layer formed. The top layer was decanted off and the oil was dried in vacuum. Upon standing the oil solidified to give an off-white solid (12.127 g, 99%) resulting in the following analytical data:

$^1$H NMR ((CD$_3$)$_2$SO 2.50 ppm): 3.78 (t, 4H, 2×CH$_2$), 3.89 (s, 6H, 2×CH$_3$), 4.84 (t, 4H, 2×CH$_2$), 7.74 (s, 4H, 4×CH), 9.26 (s, 2H, 2×NCHN).

$^{13}$C NMR ((CD$_3$)$_2$SO 39.50 ppm): 35.77 (2×CH$_3$), 48.52 (2×CH$_2$), 67.95 (2×CH$_2$), 122.59 (2×CH), 123.19 (2×CH), 136.79 (2×NCHN).

Anal. Calcd for C$_{12}$H$_{20}$BrN$_4$O (396.12): C, 36.38; H, 5.09; N, 14.14. Found: C, 36.68; H, 5.11; N, 14.53.

ESI-MS, m/z: 317 [M-Br]$^+$.

A.6 Synthesis of Ag$_2$Br$_2$[(O(CH$_2$CH$_2$ImCH$_3$)$_2$] (6)

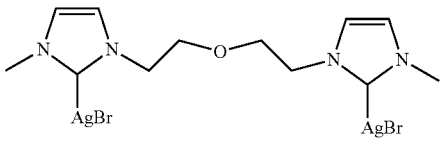

Ag$_2$O (0.144 g, 0.621 mmol) in methylene chloride (10 mL) was added to a slurry of [(O(CH$_2$CH$_2$ImCH$_3$)$_2$]Br$_2$ (0.246 g, 0.621 mmol) in methylene chloride (5 mL). The mixture was stirred in the dark for 24 h to produce an off-white suspension. The solid was allowed to settle and the solution was decanted off. The solid was washed with hexane (10 mL) and dried in vacuum. (0.370 g, 98%) resulting in the following analytical data:

$^1$H NMR ((CD$_3$)$_2$SO 2.50 ppm): 3.74 (t, 4H, 2×CH$_2$), 3.76 (s, 6H, 2×CH$_3$), 4.23 (t, 4H, 2×CH$_2$), 7.37-7.38 (m, 2H, CH, Im)

$^{13}$C NMR ((CD$_3$)$_2$SO 39.50): 38.07 (2×CH$_3$), 50.64 (2×CH$_2$), 69.48 (2×CH$_2$), 121.36 (CH, Im), 122.64 (CH, Im), 180.34 (NCN, Im).

Anal. Calcd for C$_{12}$H$_{18}$Ag$_2$Br$_2$N$_4$O (609.84): C, 23.63; H, 2.98; N, 9.19. Found: C, 23.13; H, 2.94; N, 8.86.

ESI-MS, m/z: 421 [MH-AgBr]$^+$.

A.7 Synthesis of [RuH((CH$_3$OCH$_2$CH$_2$)$_2$Im)(SImMes$_2$)][($\eta^6$-Ph)BPh$_3$] (7)

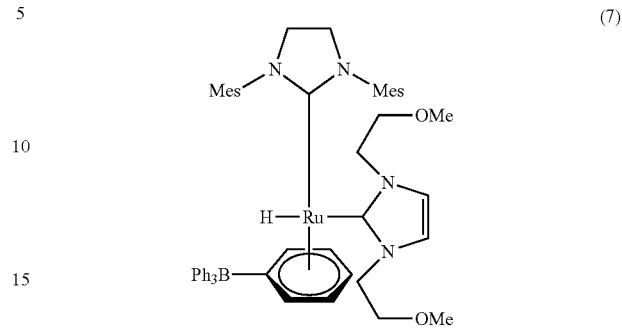

RuHCl(PPh$_3$)((CH$_3$OCH$_2$CH$_2$)$_2$Im)(SImMes$_2$) (4) (0.139 g, 0.156 mmol) in methylene chloride (5 mL) was added to a slurry of NaBPh$_4$ (0.065 g, 0.190 mmol) in methylene chloride (5 mL). The mixture was stirred for 16 h at room temperature during which time the colour of the solution changed from red to yellow. After that a white solid was filtered off through celite and the filtrate concentrated to 2 mL and 15 mL of pentane added to precipitate light yellow solid. The solid was dissolved in methylene chloride (2 mL) and benzene (10 mL) and allowed to sit at room temperature for 2 days during which pale yellow crystals formed (0.135 g, 95%) resulting in the following analytical data:

$^1$H NMR (CD$_2$Cl$_2$): −9.28 (s, 1H, RuH), 1.50 (s, 6H, 2×CH$_3$, Mes), 2.29-2.34 (m, 1H, CH$_2$), 2.34 (s, 6H, 2×CH$_3$, Mes), 2.46 (s, 6H, 2×CH$_3$, Mes), 2.48-2.51 (m, 1H, CH$_2$), 2.61-2.66 (m, 1H, CH$_2$), 3.03 (s, 3H, OCH$_3$), 3.38 (s, 3H, OCH$_3$), 3.52 (m, 8H), 3.95 (t, J=5.8 Hz, m-H, Ph), 3.98-4.04 (m, 1H, NCH$_2$CH$_2$N), 4.14 (t, J=5.8 Hz, m-H, Ph), 4.27 (d, J=6.3 Hz, 1H, o-H, Ph), 4.75 (d, J=4.8 Hz, 1H, o-H, Ph), 5.22 (t, J=5.6 Hz, p-H, Ph) 6.73 (s, 2H, 2×CH, Mes), 6.88 (d, J=2.1 Hz, 1H, Im), 6.95 (t, J=7.3 Hz, 3H, p-H, BPh$_3$), 7.01 (d, J=2.1 Hz, 1H, Im), 7.04 (t, J=7.5 Hz, 6H, m-H, BPh$_3$), 7.10 (s, 2H, 2×CH, Mes), 7.33 (d, J=7.2 Hz, 6H, o-H, BPh$_3$).

$^{11}$B {$^1$H} NMR (CD$_2$Cl$_2$): −8.11 (s, BPh$_4$).

$^{13}$C NMR ((CD$_2$Cl$_2$ 53.5 ppm): 17.32 (CH$_3$, Mes), 19.79 (CH$_3$, Mes), 20.91 (CH$_3$, Mes), 50.89 (CH$_2$), 51.07 (CH$_2$), 51.81 (NCH$_2$CH$_2$N), 58.07 (OCH$_3$), 58.96 (OCH$_3$) 71.42 (CH$_2$), 71.88 (CH$_2$), 86.79 (o-C, BPhRu) 89.27 (p-C, BPhRu), 90.72 (o-C, BPhRu), 94.93 (m-C, BPhRu), 98.81 (ipso-C, BPhRu), 119.35 (CH, Im), 120.91 (CH, Im), 122.73 (p-C, BPh$_3$), 125.65 (m-C, BPh$_3$), 129.12 (ipso-C, Mes), 129.40 (4×CH, Mes), 136.26 (6C, o-C, BPh$_3$), 136.83 (ipso-C, BPh$_3$), 137.53 (ipso-C, Mes), 139.79 (ipso-C, Mes), 184.13 (NCN) 214.22 (NCN).

Anal. Calcd for $C_{54}H_{63}BN_4O_2Ru$ (911.98): C, 71.12; H, 6.96; N, 6.14. Found: C, 71.59; H, 7.29; N, 5.80.

A.8 Synthesis of [Ru(O(CH$_2$CH$_2$ImCH$_3$)$_2$(PPh$_3$)$_2$][AgBr$_2$] (8)

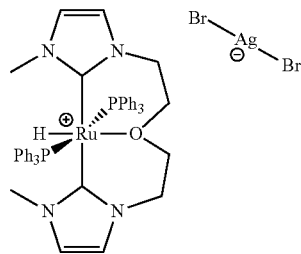

RuHCl(PPh$_3$)$_3$ (1.103, 1.193) in methylene chloride (5 mL) was added to a slurry of Ag$_2$Br$_2$[(O(CH$_2$CH$_2$ImCH$_3$)$_2$] (6) (0.842 g, 1.381 mmol) in methylene chloride (5 mL) at room temperature resulting in color change from purple to red over a period of 16 h. The mixture was filtered through a plug of celite and the red filtrate was concentrated to 2 mL. The addition of THF to this solution caused a yellow precipitate to form. The solid was collected by filtration and washed with THF (40 mL) and then dried on high vacuum (0.752 g, 56%) resulting in the following analytical data:

$^1$H NMR (CD$_2$Cl$_2$, 5.32 ppm): −21.76 (t, J=23.5 Hz, 1H, RuH), 2.90 (s, 6H, 2×NCH$_3$), 3.42 (m, 4H, 2×CH$_2$), 3.28 (m, 4H, 2×CH), 6.44 (d, J=1.9 Hz, 2H, Im), 6.67 (d, J=1.9 Hz, 2H, Im), 7.09-7.15 (m, 12 H, PPh$_3$, o-H, 2×PPh$_3$), 7.20 (t, J=7.3 Hz, 12 H, m-H, 2×PPh$_3$), 7.28 (t, J=7.1 Hz, 6 H, p-H, 2×PPh$_3$).

$^{13}$C NMR ((CD$_2$Cl$_2$ 53.5 ppm): 37.60 (2×NCH$_3$), 49.95 (2×CH$_2$), 72.53 (2×CH$_2$), 121.42 (2×CH, Im), 123.61 (2×CH, Im), 127.99 (t, $^3J_{CP}$=4.0 Hz, m-C, 2×PPh$_3$), 128.86 (p-C, 2×PPh$_3$), 132.94 (t, $^2J_{CP}$=5.66 Hz, o-C, 2×PPh$_3$), 138.31 (t, $^1J_{CP}$=16.95 Hz, ipso-C, 2×PPh$_3$) 191.56 (2×NCN, Im).

$^{31}$P NMR: 47.26 (s, 2×PPh$_3$).

Anal. Calcd for $C_{48}H_{49}AgBr_2N_4OP_2Ru$ (1128.63): C, 51.08; H, 4.38; N, 4.96. Found: C, 50.84; H, 4.50; N, 4.93.

A.9 Synthesis of [RuH(O(CH$_2$CH$_2$ImCH$_3$)$_2$(PPh$_3$)$_2$][BPh$_4$] (9)

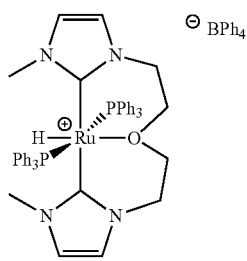

[RuH(O(CH$_2$CH$_2$ImCH$_3$)$_2$(PPh$_3$)$_2$][AgBr$_2$] (8) (0.114 g, 0.101 mmol) was dissolved in methylene chloride (5 mL) and added to a slurry of NaBPh$_4$ (0.062 g, 0.181 mmol) in methylene chloride. The mixture was stirred for 24 h without any noticeable colour change. The resulting white precipitate was filtered off and the solution was concentrated to dryness to give a light yellow foam/solid. Pentane was added to the mixture which was then stirred to produce a yellow suspension. The solution was decanted off and the yellow solid was dried on high vacuum (0.110 g, 93%) resulting in the following analytical data:

$^1$H NMR (CD$_2$Cl$_2$, 5.32 ppm): −21.77 (t, J=25.5 Hz, 1H, RuH), 2.90 (s, 6H, 2×NCH$_3$), 3.16 (m, 4H, 2×CH$_2$), 3.34 (m, 4H, 2×CH$_2$), 6.41 (s, 2H, Im), 6.52 (s, 2H, Im), 6.88 (t, J=7.3 Hz, 4H, p-H, BPh$_4$), 7.04 (m, 8 H, o-H, BPh$_4$), 7.07-7.13 (m, 12H, m-H, 2×PPh$_3$), 7.19 (t, J=6.7 Hz, 12H, m-H, 2×PPh$_3$), 7.26-7.35 (m, 14H, (p-H, 2×PPh$_3$), (m-H, BPh$_4$)).

$^{11}$B {$^1$H} NMR (CD$_2$Cl$_2$): −6.59 (s).

$^{13}$C NMR ((CD$_2$Cl$_2$ 53.5 ppm): 37.61 (2×NCH$_3$), 49.70 (2×CH$_2$), 72.32 (2×CH$_2$), 121.48 (2×CH, Im), 121.83 (p-C, BPh$_4$), 123.49 (2×CH, Im), 125.70 (q, $^2J_{CP}$=2.7 Hz, o-C, BPh$_4$), 127.98 (t, $^3J_{CP}$=4.0 Hz, m-C, 2×PPh$_3$), 128.91 (p-C, 2×PPh$_3$), 132.91 (t, $^2J_{CB}$=5.7 Hz, o-C, 2×PPh$_3$), 135.95 (q, $^3J_{CB}$=1.3 Hz, m-C, BPh$_4$), 138.24 (t, $^1J_{CP}$=17.0 Hz, ipso-C, 2×PPh$_3$), 164.04 (q, $^1J_{CB}$=49.4 Hz, ipso-C, BPh$_4$), 191.45 (2×NCN, Im)

$^{31}$P NMR: 48.43 (s).

Anal. Calcd for $C_{72}H_{69}BN_4OP_2Ru$ (1180.17): C, 73.27; H, 5.89; N, 4.75. Found: C, 73.26; H, 6.21; N, 4.61.

A.10 Synthesis of [RuH((CH$_3$OCH$_2$CH$_2$)$_2$Im)(SIm Mes$_2$)][(PF$_6$)] (10)

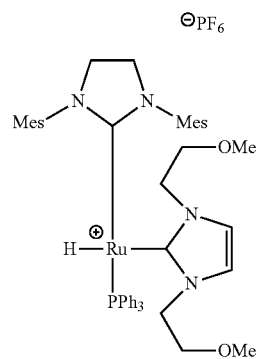

The title compound (10) was prepared by treating RuHCl (PPh$_3$)((CH$_3$OCH$_2$CH$_2$)$_2$Im)(SImMes$_2$) (4) in methylene chloride (5 mL) with an equimolar amount of AgPF$_6$ in methylene chloride (5 mL). Compound 10 was isolated a red crystals from a THF/pentane solution resulting in the following analytical data.

$^1$H NMR (CD$_2$Cl$_2$): −23.55 (br. s, RuH)

$^{19}$F {$^1$H} NMR (CD$_2$Cl$_2$): 73.4 (d, J=710.4 Hz).

$^{31}$P {$^1$H} NMR (CD$_2$Cl$_2$): 43.3 (br s, PPh$_3$), −143.44 (sept, PF$_6$)

A.11-A.14 Synthesis of RuHCl(PPh$_3$)$_2$[(t-butyl-OCH$_2$CH$_2$)$_2$Im] (14)

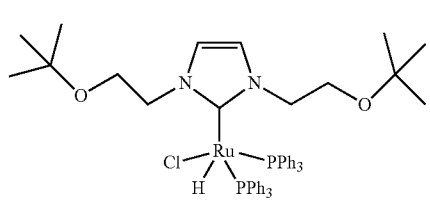

A.11 Synthesis of tert-butyl 2-chloroethyl ether (ClCH$_2$CH$_2$—O-(t-Butyl)) (11)

Tert-butyl 2-chloroethyl ether was synthesized as disclosed by P. I. Dalko and Y. Langlois in *J. Org. Chem.* 1998, 63, 8107. The purification process, however, was performed by using flash column separation (with hexane as elute solvent, SiO₂) and clean product was obtained with a yield of, 93%.

A.12 Synthesis of [(t-Butyl-OCH₂CH₂)₂Im]Cl (12)

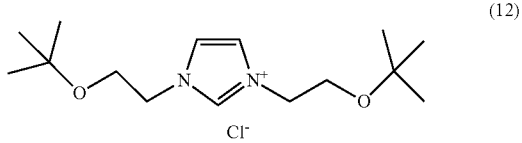 [SMILES: CC(C)(C)OCCn1cc[n+](CCOC(C)(C)C)c1 ; [Cl-]]

(12)

Tert-butyl 2-chloroethyl ether (11) (3.35 g, 24.6 mmol) was added to a solution of trimethylsilylimidazole (1.00 g, 7.14 mmol) in toluene (5 mL) in a bomb. The mixture was heated at 110° C. for 7 days. While cooling to room temperature, the mixture became solid. The solid was dissolved in dichloromethane (5 mL). The dichloromethane solution was transferred from the bomb to a vial and concentrated till about 3 mL. Then, pentane (10 mL) was added to the dichloromethane solution to precipitate solid. The white solid was filtered under vacuum, washed by diethyl ether (2×5 mL), dried under vacuum and obtained with a yield of 56% (1.215 g). The following analytical data were obtained.

¹H NMR (300 M, CD₂Cl₂, 5.32 ppm): 1.13 (s, 18H, 2×C(CH₃)₃), 3.71 (t, J=4.8 Hz, 4H, 2×CH₂), 4.50 (t, J=4.8 Hz, 4H, 2×CH₂), 7.45 (d, J=1.6 Hz, 2H, 2×CH), 10.72 (t, J=1.6 Hz, 1H, NCHN).

¹³C NMR (75 M, CD₂Cl₂, 53.8 ppm): 27.42 (2×CH(CH₃)₃), 50.83 (2×CH(CH₃)₃), 60.88 (2×CH₂), 74.15 (2×CH₂), 122.72 (2×CH—N), 138.35 (N—C—N).

HRMS: C₁₅H₂₉N₂O₂ (M−Cl) Calc. Mass: 269.2223. Found Mass: 269.2227.

A.13 Synthesis of AgCl[(t-Butyl-OCHCH₂)₂Im] (13)

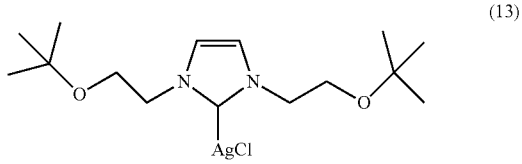

(13)

Ag₂O (0.259 g, 1.12 mmol) in methylene chloride (5 mL) was added to a solution of [(t-Butyl-OCH₂CH₂)₂Im]Cl (12) (0.593 g, 1.96 mmol) in methyl chloride (5 mL). The slurry solution was stirred in the dark for 24 h. The excess Ag₂O was filtered off through celite and the resulting yellow solution was concentrated to get yellow oil product, which was then treated by high vacuum for overnight to yield 0.670 g of product (13) (83%). The following analytical data were obtained.

¹H NMR (400 M, CD₂Cl₂, 5.32 ppm): 1.08 (s, 18H, 2×C(CH₃)₃), 3.62 (t, J=4.8 Hz, 4H, 2×CH₂), 4.20 (t, J=5.0 Hz, 4H, 2×CH₂), 7.11 (s, 2H, 2×CH).

¹³C NMR (100 M, CD₂Cl₂, 53.8 ppm): 27.37 (2×CH(CH₃)₃), 53.08 (2×CH(CH₃)₃), 62.15 (2×CH₂), 73.68 (2×CH₂), 122.15 (2×CH), 179.28 (NCN).

Anal. Calcd for C₁₅HF₂₈AgClN₂O₂ (412.72): C, 43.76; H, 6.85; N, 6.80. Found: C, 44.33; H, 6.65; N, 7.49.

ESI-MS: 375.1 [C₁₅H₂₈N₂O₂Ag] (M−Cl).

A.14 Synthesis of RuHCl(PPh₃)₂[(t-butyl-OCH₂CH₂)₂Im] (14)

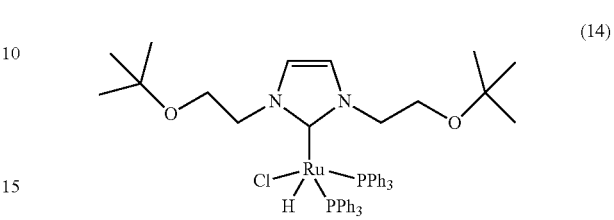

(14)

AgCl[(t-Butyl-OCH₂CH₂CH₂)₂Im] (13) (0.230 g, 0.557 mmol) which had been dried under vacuum for two days before this reaction and RuHCl(PPh₃)₃ (0.395 g, 0.428 mmol) were combined and toluene (10 mL) was added. The suspension was stirred for 57 h at room temperature. The mixture was filtered through a plug of celite and the red filtrate was concentrated till dry. Ether (15 mL) was used to extract product and the ether solution was filtered through Al₂O₃ plug. The filtrate was then concentrated till dry. The residue was then subjected to recrystallization in toluene/pentane at −35° C. for two days to obtain dark-red crystals (75 mg; 17%). The following analytical data were obtained.

¹H NMR (400 M, CD₂Cl₂, 5.32 ppm): −32.37 (t, J=23.14 Hz, 1H, RuH), 0.91 (s, 18H, 2×OC(CH₃)₃), 2.15 (t, J=6.83 Hz, 2H, CH₂) 2.34 (s, 3H, PhCH₃), 2.36 (t, J=6.83 Hz, 2H, CH₂), 2.80 (t, J=4.94 Hz, 2H, CH₂), 3.56 (t, J=4.94 Hz, 2H, CH₂), 6.49 (s, 1H, CH, Im), 6.94 (s, 1H, CH, Im), 7.22-7.33 (m, 23H, 2×PPh₃+PhCH₃), 7.41-7.45 (m, 12H, 2×PPh₃).

³¹P {¹H} NMR: 47.55, 47.59.

Anal. Calcd for C₅₈H₆₇ClN₂O₂P₂Ru.C₇H₈ (1022.64): C, 68.12; H, 6.60; N, 2.74. Found: C, 67.54; H, 7.06; N, 2.92.

A.15-A.18 Synthesis of RuHCl(PPh₃)₂{[(2,6-Diisopropyl-phenyl)-OCH₂CH₂]₂Im]} (18)

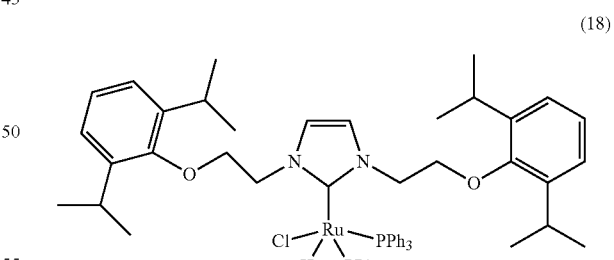

(18)

A.15 Synthesis of (2,6-diisopropylphenyl)-2-chloroethyl ether (ClCH₂CH₂O-(diisopropyl-phenyl)) (15)

(ClCH₂CH₂—O-(diisopropyl-phenyl)) (15) was synthesized as disclosed by W. B. Wheatley, and C. T. Holdrege in *J. Org. Chem.* 1958, 23, 568 and obtained with a yield of 31% after column purification (SiO₂, Hexane)

HRMS: C₁₄H₂₅³⁵Cl₁₄NO (M+NH4) Calc. Mass: 258.1625. Found Mass: 258.1632.

A.16 Synthesis of {[(2,6-diisopropylphenyl)-OCH$_2$CH$_2$]$_2$Im}Cl (16)

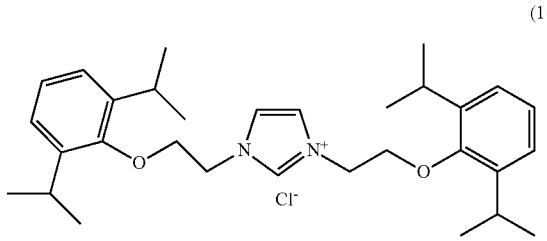
(16)

(2,6-diisopropylphenyl)-2-chloroethyl ether (15) (5.00 g, 20.8 mmol) was added to a solution of trimethylsilylimidazole (0.827 g, 5.90 mmol) in toluene (5 mL). The mixture was heated at 110° C. for 6 days. The toluene solution was transferred from a bomb to a vial and concentrated till about 3 mL. Then, pentane (10 mL) was added to the toluene solution to precipitate solid. The white solid was filtered under vacuum and washed by diethyl ether (2×5 mL) and dried under vacuum to yield 2.566 g of product (16) (83%). The following analytical data were obtained.

$^1$H NMR (CD$_2$Cl$_2$, 5.32 ppm): 1.19 (d, J=6.9 Hz, 24H, 4×CH(CH$_3$)$_2$), 3.00 (m, J=6.9 Hz, 4H, 4×CH(CH$_3$)$_2$), 4.18 (t, J=4.7 Hz, 4H, 2×CH$_2$), 4.93 (t, J=4.7 Hz, 4H, 2×CH$_2$), 7.12 (m, 6H, 6×CH), 7.77 (d, J=1.5 Hz, 2H, 2×CH), 11.33 (t, J=1.5 Hz, 1H, NCHN).

$^{13}$C NMR (CD$_2$Cl$_2$, 53.8 ppm): 24.09 (4×CH(CH$_3$)$_2$), 27.05 (4×CH(CH$_3$)$_2$), 50.69 (2×CH$_2$), 72.50 (2×CH$_2$), 123.19 (2×CH on imidazolium), 124.54 (4×CH on phenyl), 125.75 (2×CH on phenyl), 139.60 (NCHN), 141.66 (2×OC—C—CH(CH$_3$)$_2$ on phenyl), 152.26 (2×O—C on phenyl).

HRMS: C$_{31}$H$_{45}$N$_2$O$_2$(M−Cl) Calc. Mass: 477.3475. Found Mass: 477.3496.

A.17 Synthesis of AgCl {[(2,6-Diisopropylphenyl)-OCH$_2$CH$_2$]$_2$Im]} (17)

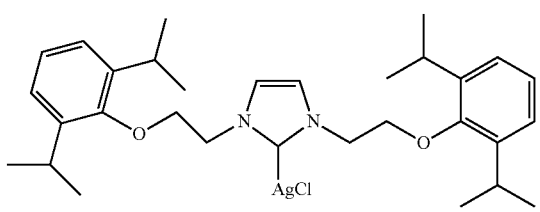
(17)

Ag$_2$O (0.362 g, 1.398 mmol) in methylene chloride (5 mL) was added to a solution of {[(2,6-Diisopropylphenyl)-OCH$_2$CH$_2$]$_2$Im}Cl (16) (0.500 g, 0.978 mmol) in methyl chloride (5 mL). The slurry solution was stirred in the dark for 45 h. The solution was filtered through celite plug to get dark solution which was dried under vacuum. Then, 10 mL of ether was used to extract product from the residue. The ether solution was then filtered through celite plug. The filtrate was concentrated till dry. The residue was dissolved in 3 mL of dichloromethane and mixed with 15 mL of pentane. The mixture was left in freezer to get crystal, however, no crystal was obtained. Then, the solvent was removed till dry and the light brown solid was left under high vacuum for 2 days (0.462 g, 76%). The following analytical data were obtained.

$^1$H NMR (CD$_2$Cl, 5.32 ppm): 1.18 (d, J=6.9 Hz, 12H, 2×CH(CH$_3$)$_2$), 3.00 (m, J=6.9 Hz, 4H, 4×CH(CH$_3$)$_2$), 4.11 (t, J=4.9 Hz, 4H, 2×CH$_2$), 4.60 (t, J=4.9 Hz, 4H, 2×CH$_2$), 7.10 (br, 6H, 6×CH), 7.40 (s, 2H, 2×CH).

$^{13}$C NMR (CD$_2$Cl$_2$, 53.8 ppm): 24.19 (4×CH(CH$_3$)$_2$), 26.85 (4×CH(CH$_3$)$_2$), 52.88 (2×CH$_2$), 74.00 (2×CH$_2$), 122.73 (2×CH on imidazolium), 124.45 (4×CH on phenyl), 125.46 (2×CH on phenyl), 141.87 (2×OC—C—CH(CH$_3$)$_2$ on phenyl), 152.67 (2×O—C on phenyl), 180.79 (NCHN).

Anal. Calcd for C$_{31}$H$_{44}$AgClN$_2$O$_2$ (620.02): C, 60.05; H, 7.15; N, 4.52. Found: C, 60.21; H, 7.06; N, 4.57.

ESI-MS: 583.2 [C$_{31}$H$_{44}$AgN$_2$O$_2$ (M−Cl)].

A.18 Synthesis of RuHCl(PPh$_3$)$_2${[(2,6-diisopropylphenyl)-OCH$_2$CH$_2$]$_2$Im]} (18)

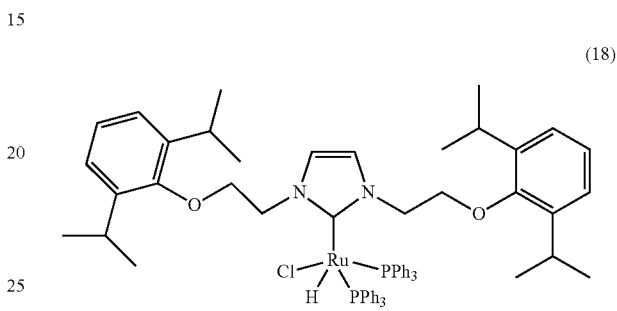
(18)

AgCl{[(2,6-Diisopropylphenyl)-OCH$_2$CH$_2$]Im]} (17) (0.284 g, 0.459 mmol) and RuHCl(PPh$_3$)$_3$ (0.326 g, 0.353 mmol) were combined and toluene (10 mL) was added. The suspension was stirred for 48 h at room temperature. The reaction mixture was filtered through celite plug to get red solution, which was then concentrated till dry. The residue was extracted with ether (12 mL). The ether solution was then filtered through Al$_2$O$_3$ plug. The filtrate was concentrated till dry. The residue was dissolved in 2 mL of toluene and 15 mL of pentane. The solution was left at −35° C. for one day to get red solid precipitates (55 mg; 14%). The following analytical data were obtained.

$^1$H NMR (CD$_2$Cl$_2$, 5.32 ppm): −31.98 (t, J=23.7 Hz, 1H, RuH), 1.12 (d, J=6.8 Hz, 12H, 2×CH(CH$_3$)$_2$), 1.16 (d, J=6.8 Hz, 12H, 2×CH(CH$_3$)$_2$), 2.51 (t, J=6.2 Hz, 2H, CH$_2$), 2.70 (t, J=6.2 Hz, 2H, CH$_2$), 2.87 (septet, J=6.8 Hz, 2H, 2×CH(CH$_3$)$_2$), 2.97 (septet, J=6.8 Hz, 2H, 2×CH(CH$_3$)$_2$), 3.23 (t, J=4.4 Hz, 2H, CH$_2$), 3.94 (t, J=4.4 Hz, 2H, CH$_2$), 6.80 (m, 1H, Im-H), 7.02-7.05 (m, 5H, o-diisopropyl-Ar—H and Im-H), 7.22-7.34 (m, 20H, 18H for 2×PPh$_3$ and 2H for p-diisopropyl-Ar—H), 7.44-7.48 (m, 12H, 2×PPh$_3$).

$^{31}$P {1H}: 47.36 (br. s).

Anal. Calcd for C$_{67}$H$_{78}$ClN$_2$O$_2$P$_2$Ru (1139.80): C, 70.66; H, 6.64; N, 2.46. Found: C, 70.11; H, 6.90; N, 2.62.

A.19-A.22 Synthesis of RuHCl(PPh$_3$)$_2$[(CH$_3$OCH$_2$CH$_2$)$_2$benzim] (22) (with "Benzim" Standing for "Benzimidazole")

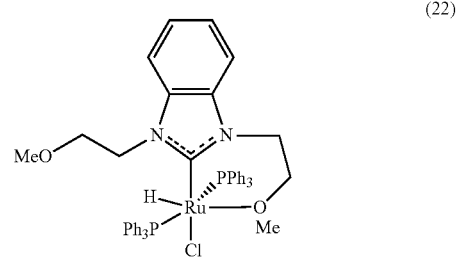
(22)

A.19 Synthesis of 1-(2-methoxyethyl)-1H-benzimidazole (19)

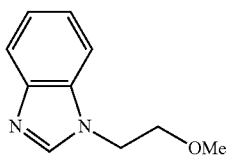

(19)

KOH (1.12 g, 20 mmol) was added to a flask equipped with benzimidazole (2.36 g, 20 mmol) and acetonitrile (20 mL). The mixture was then stirred at room temperature for 1 h before adding 2-chloroethyl methyl ether (1.90 g, 20 mmol) slowly. The mixture was then heated at 76° C. for 17 h. The reaction mixture was cooled to room temperature. All volatiles were removed by vacuum. The residue was added with water (20 mL). The aqueous solution was extracted by chloroform (3×30 mL). The organic layers were collected, washed by water (2×20 mL) and dried by $MgSO_4$. The solvent was removed by vacuum to obtain light-yellow oil (2.80 g, 80%). The characterization data were identical to those literature values (Ozdemir, I.; Sahin, N.; Gok, Y.; Demir, S.; Cetinkaya, B. *J. Mol. Catal. A: Chem.* 2005, 234, 181. and Denton, J. R. *Synthesis* 2010, 775-782).

A.20 Synthesis of 1,3-di(2-methoxyethyl)benzimidazole chloride (20)

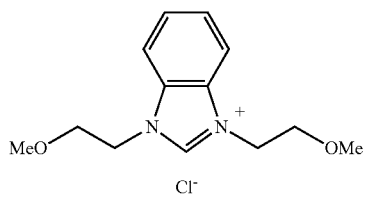

(20)

1-(2-Methoxyethyl)-1H-benzimidazole (1.17 g, 6.66 mmol) was dissolved in dry acetonitrile (2.0 mL), into which was then added 2-chloroethyl methyl ether (0.646 g, 6.8 mmol). The mixture was heated at 120° C. for 5 days. The white solid precipitated while the reaction mixture was cooling to room temperature. Solid was separated by removing top-layer acetonitrile solution. The white solid was then washed by diethyl ether (5.0 mL) and dried under high vacuum (1.174 g, 65%).

$^1$H NMR ($CDCl_2$, 532 ppm): 3.34 (s, 6H, 2×OMe), 3.93 (t, J=4.9 Hz, 4H, 2×$CH_2$), 4.82 (t, J=4.9 Hz 4H, 2×$CH_2$), 7.61 (dd, J=6.3 Hz, J=3.2 Hz, 2×CH), 7.84 (dd, J=6.3 Hz, J=3.2 Hz, 2×CH), 11.57 (s, 1H, NCHN).

$^{13}$C NMR ($CD_2Cl_2$, 53.8 ppm): 47.89 (2×$CH_2$), 59.17 (2×$OCH_3$) 70.56 (2×$CH_2$), 113.97 (2×CH), 127.00 (2×CH), 132.22 (2×C), 144.34 (NCHN).

Anal. Calcd. For $C_{13}H_{19}ClN_2O_2$ (270.76): C, 57.67; H, 7.07; N, 10.35. Found: C, 57.55; H, 7.29; N, 10.96.

HRMS: $C_{13}H_{19}ClN_2O_2$(M−Cl) Calc. Mass: 235.1441. Found Mass: 235.1448.

A.21 Synthesis of AgCl[$(CH_3OCH_2CH_2)_2$benzimidazole] (21)

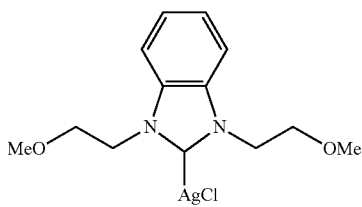

(21)

$Ag_2O$ (0.559 g, 2.41 mmol) in methylene chloride (5 mL) was added to a solution of 1,3-di(2-methoxyethyl)benzimidazole chloride (0.466 g, 1.72 mmol) in methyl chloride (5 mL). The slurry solution was stirred in the dark for 22 h. The excess $Ag_2O$ was filtered off through celite and the resulting dark-yellow solution was concentrated to get brown color product, which was then treated by high vacuum for overnight to yield 0.590 g of product (21) (91%).

$^1$H NMR (400 M, $CD_2Cl_2$, 5.32 ppm): 3.29 (s, 6H, 2×OMe), 3.83 (t, J=5.2 Hz, 4H, 2×$CH_2$), 4.63 (t, J=5.2 Hz 4H, 2×$CH_2$), 7.40 (dd, J=6.1 Hz, J=3.0 Hz, CH), 7.60 (dd, J=6.3 Hz, J=3.2 Hz, CH).

$^{13}$C NMR (100M, $CD_2Cl_2$, 53.8 ppm): 49.84 (2×$CH_2$), 59.19 (2×$OCH_3$), 72.13 (2×$CH_2$), 112.33 (2×CH), 124.23 (2×CH), 134.59 (2×C), 189.28 (NCHN).

Anal. Calcd. for $C_{13}H_{18}AgClN_2O_2$ (377.62): C, 41.35; H, 4.80; N, 7.42. Found: C, 41.76; H, 4.86; N, 7.59.

A.22 Synthesis of $RuHCl(PPh_3)_2$[$(CH_3OCH_2CH_2)_2$benzimidazole] (22)

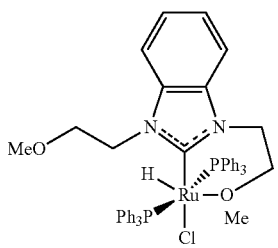

(22)

AgCl[$(CH_3OCH_2CH_2)_2$benzimidazole] (21) (0.296 g, 0.783 mmol) and $RuHCl(PPh_3)_3$ (0.700 g, 0.759 mmol) were combined and toluene (20 mL) was added. The suspension was stirred for three days at room temperature. The green solid that appeared in the solution was collected to get crude product (0.358 g). The crude product was dissolved in 3.0 mL of dichloromethane, which was layered by 17 mL of diethyl ether. The mixture was left at room temperature for one day to get yellow color crystal (0.193 g). The following analytical data were obtained.

$^1$H NMR (400 M, $CD_2Cl_2$, 5.32 ppm): −22.59 (t, $J_{P-H}$=23.8 Hz, 1H, Ru—H), 2.61 (t, $J_{H-H}$=6.6 Hz, 2H, $CH_2O$), 2.81 (s, 3H, $OCH_3$), 2.87 (s, 3H, $OCH_3$), 3.10 (t, J=6.6 Hz, 2H, N—$CH_2$), 3.58 (t, J=4.1 Hz, 2H, $CH_2O$), 3.69 (t, J=4.1 Hz, 2H, N—$CH_2$), 6.63 (d, J=7.8 Hz, 1H, benzi-CH), 6.85 (d, J=7.8 Hz, 1H, benzi-CH), 6.95 (t, J=7.8 Hz, 1H, benzi-CH), 7.03 (t, J=7.8 Hz, benzi-CH), 7.09 (m, 12H, 12×CH on $PPh_3$), 7.23 (m, 6H, 6×CH on $PPh_3$), 7.45 (broaden singlet, 12H, 12×CH on $PPh_3$).

$^{13}$C NMR (100 M, $CD_2Cl_2$, 53.8 ppm): 45.76 ($CH_2$), 45.83 ($CH_2$), 58.31 ($OCH_3$), 59.97 ($OCH_3$), 68.93 ($CH_2$), 73.09 ($CH_2$), 105.64 (CH, benzimidazolium), 108.88 (CH, benzimidazolium), 120.57 (C, benzimidazolium) 120.67 (C, benzimidazolium), 127.67 (t, J=4.1 Hz, $PPh_3$), 128.85 ($PPh_3$), 134.67 (t, J=5.6 Hz, $PPh_3$), 136.13 (CH, benzimidazolium), 136.21 (CH, benzimidazolium), 137.88 (t, J=17.3 Hz, $PPh_3$), 209.82 (td, $J_{P-C}$=11.9 Hz, $J_{C-H(Hydride)}$=4.4 Hz, NCN carbon).

$^{31}$P NMR (162 M, $CD_2Cl_2$): 44.69 ($PPh_3$), 44.60 ($PPh_3$).

Anal. Calcd. for $C_{49}H_{49}ClN_2O_2P_2Ru$ (896.40): C, 65.65; H, 5.51; N, 3.13. Found: C, 64.80; H, 5.67; N, 3.06.

A.23-A.26 Synthesis of $Ru[(t-hexyl-OCH_2CH_2Im]HCl(PPh_3)_2$ (26)

In the following "thx" also stands for t-hexyl this representing a 2,3-dimethyl-2-butyl group.

A.23 Synthesis of t-Hexyl 2-chloroethyl ether (23)

2-Chloroethanol (0.83 mL, 12.42 mmol), 2,3-dimethyl-2-butene (3.75 mL, 31.53 mmol), and dry dichloromethane (2 mL) were combined in a 100 mL Schlenk bomb. The flask was immersed in a water bath and concentrated sulfuric acid (0.15 mL) was added, resulting in a color change to red. The bomb was quickly sealed and stirred at room temperature for 4 days. The mixture was poured into a saturated aqueous solution of $NaHCO_3$, and agitated until effervescence had ceased. Dichloromethane (10 mL) was added, the organic layer separated and dried over anhydrous $MgSO_4$. Gentle removal of the solvent on a rotary evaporator yielded the crude product as an orange oil. Pentane (10 mL) was added, and the solution was filtered through a short column of silica. Careful solvent removal yielded the product (1.75 g, 84%) as a light yellow oil of sufficient purity for subsequent reactions. The following analytical data were obtained.

B.p: decomposes quickly above 130° C.

$^1$H NMR ($CDCl_3$): δ 3.61-3.53 (m, 4H, $OCH_2CH_2Cl$), 1.80 (septet, $^3J_{H-H}$=6.8 Hz, 1H, $CH(CH_3)_2$), 1.10 (s, 6H, $C(CH_3)_2$), 0.89 (d, $^3J_{H-H}$=6.8 Hz, 6H, $CH(CH_3)_2$).

$^{13}$C NMR ($CDCl_3$): δ 77.96 ($C(CH_3)_2$), 61.68 ($CH_2$), 43.81 ($CH_2$), 35.76 (CH), 22.12 ($C(CH_3)_2$), 17.50 ($CH(CH_3)_2$).

EI-MS: 182.1 $[MNH_4]^+$, 165.1 $[MH]^+$, 85.1 $[(CH_3)_2CCH(CH_3)_2]^+$

A.24 Synthesis of $[(thxOCH_2CH_2)_2ImH]Cl$ (24)

t-Hexyl-2-chloroethyl ether (23) (0.629 g, 3.82 mmol), 1-(trimethylsilyl)imidazole (154 mg, 1.10 mmol) and toluene (0.7 mL) were stirred at 110° C. for 4 days in complete darkness. The mixture was cooled to room temperature and pentane (20 mL) was added, resulting in the precipitation on an opaque oil. The supernatant was decanted and the oil was washed with pentane (3×10 mL). Removal of traces of solvent under high vacuum yielded the product (190 mg, 53%) as a light yellow oil. The following analytical data were obtained.

$^1$H NMR ($CD_2Cl_2$): δ 10.83 (s, 1H, N(CH)N), 7.38 (s, 2H, NCHCHN), 4.50 (vt, $^3J_{H-H}$=4.7 Hz, 4H, 2–$CH_2$), 3.70 (vt, $^3J_{H-H}$=4.7 Hz, 4H, 2×$CH_2$), 1.75 (septet, $^3J_{H-H}$=6.8 Hz, 2H, $CH(CH_3)_2$), 1.04 (s, 12H, 2–$C(CH_3)_2$), 0.82 (d, $^3J_{H-H}$=6.8 Hz, 2H, $CH(CH_3)_2$).

$^{13}$C NMR ($CD_2Cl_2$): δ 138.20 (NCHN), 122.87 (NCHCHN), 78.65 ($C(CH_3)_2$), 60.23 ($CH_2$), 50.97 ($CH_2$), 36.27 ($CH(CH_3)_2$), 22.08 ($C(CH_3)_2$), 17.55 ($CH(CH_3)_2$)

A.25 Synthesis of $[(thxOCH_2CH_2)_2Im]AgCl$ (25)

$[(thxOCH_2CH_2)_2ImH]Cl$ (24) (178 mg, 0.49 mmol) and $Ag_2O$ (127 mg, 0.55 mmol) were stirred overnight in dichloromethane (5 mL) in complete darkness. The resulting suspension was filtered through a plug of Celite, and the solvent was removed under high vacuum to yield the product (201 mg, 88%) as a brown oil. The oil was dried under high vacuum for a period of 48 h to remove traces of water. The following analytical data were obtained.

$^1$H NMR ($CD_2Cl_2$): δ 7.11 (s, 2H, NCHCHN), 4.22 (vt, $^3J_{H-H}$=5.1 Hz, 4H, 2×$CH_2$), 3.62 (vt, $^3J_{H-H}$5.1 Hz, 4H, 2×$CH_2$), 1.73 (septet, $^3J_{H-H}$=6.8 Hz, 2H, $CH(CH_3)_2$), 1.00 (s, 12H, 2–$C(CH_3)_2$), 0.81 (d, $^3J_{H-H}$=6.8 Hz, 2H, CH $(CH_3)_2$). $^{13}$C NMR ($CD_2Cl_2$): δ 122.39 (NCHCHN), 78.18 ($OC(CH_3)_2$), 61.61 ($CH_2$), 53.30 ($CH_2$), 36.44 ($CH(CH_3)$), 22.10 ($C(CH_3)_2$), 17.62 ($CH(CH_3)$).

Anal. Calcd. for $C_{19}H_{36}AgClN_2O_2$ (467.89): C, 48.78; H, 7.76; N, 5.99. Found: C, 48.93; H, 7.55; N, 6.96.

A.26 Synthesis of $Ru[(thzOCH_2CH_2)_2Im]HCl(PPh_3)_2$ (26)

$[(thxOCH_2CH_2)_2Im]AgCl$ (25) (201 mg, 0.43 mmol) and $RuHCl(PPh_3)_3$ (337 mg, 0.36 mmol) were stirred in toluene (15 mL) for 24 hours resulting in a brown suspension. The solution was filtered through a plug of celite, and the solvent was removed in vacuo. The oily residue was washed with pentane (2×10 mL) and dissolved in diethyl ether (10 mL). The solution was filtered through a short column of alumina and the solvent was removed under high vacuum to yield the product (210 mg, 49%) as a dark brown solid. Crystals suitable for X-Ray diffraction were grown from toluene/hexamethyldisiloxane. The following analytical data were obtained.

$^1$H NMR ($CD_2Cl_2$): δ 7.48-7.42 (m, 12H, m-$PPh_3$), 7.35-7.23 (m, 18H, o-$PPh_3$ & m-$PPh_3$) 6.95 (d, $^3J_{H-H}$=2.1 Hz, 1H, NCH), 6.52 (d, $^3J_{H-H}$=2.1 Hz, 1H, NCH), 3.61 (vt, $^3J_{H-H}$=4.8 Hz, 2H, $CH_2$), 2.80 (vt, $^3J_{H-H}$=4.8 Hz, 2H, $CH_2$), 2.34 (t, $^3J_{H-H}$=6.1 Hz, 2H, $CH_2$), 2.12 (t, $^3J_{H-H}$=6.1 Hz, 2H, $CH_2$), 1.50 (septet, $^3J_{H-H}$=7.1 Hz, 1H, $CH(CH_3)_2$), 1.47 (septet, $^3J_{H-H}$=7.1 Hz, 1H, $CH(CH_3)_2$), 0.79 (apparent doublet, $^3J_{H-H}$=6.8 Hz, 18H, 2–$C(CH_3)_2$ & $CH(CH_3)_2$), 0.76 (d, $^3J_{H-H}$=6.8 Hz, $CH(CH_3)_2$), −32.34 (t, $^2J_{H-P}$=23.3 Hz, 1H, RuH).

$^{31}$P NMR ($CD_2Cl_2$): δ 47.52 ($PPh_3$), 47.47 ($PPh_3$).

$^{13}$C NMR ($CD_2Cl_2$): δ 187.83 (observable only in HMBC, NCN), 138.00 (t, $^1J_{C-P}$=17.6 Hz, $PPh_3$ ipso-C), 134.78 (t, $J_{C-P}$=5.8 Hz, $PPh_3$), 129.14 ($PPh_3$), 128.06 (t, $J_{C-P}$=4.3 Hz, $PPh_3$), 120.79 (NCH), 119.76 (NCH), 77.76 ($C(CH_3)_2$), 77.41 ($C(CH_3)_2$), 61.16 ($CH_2$), 58.21 ($CH_2$), 50.42 ($CH_2$), 48.67 ($CH_2$), 36.18 ($CH(CH_3)_2$), 35.86 ($CH(CH_3)_2$), 22.19 ($C(CH_3)_2$), 22.00 ($C(CH_3)_2$), 17.62 ($CH(CH_3)_2$), 17.60 ($C(CH_3)_2$).

Anal. Calcd. for $C_{55}H_{67}ClN_2O_2P_2Ru$ (986.63): C, 66.95; H, 6.86; N, 2.84. Found: C, 65.81; H, 7.13; N, 2.91.

A.27-A.29 Synthesis of $Ru[(PhOCH_2CH_2)_2Im]HCl(PPh_3)_2$ (29)

A.27 Synthesis of $[(PhOCH_2CH_2)_2ImH]Cl$ (27)

(2-chloroethoxy)benzene (5.02 g, 32.05 mmol) and 1-(trimethylsilyl)imidazole (1.33 g, 9.48 mmol) and toluene (5 mL) were stirred at 110° C. for 7 days in complete darkness. The resultant biphasic mixture was cooled to room temperature and the top layer was discarded. The viscous bottom layer was dissolved in dichloromethane (15 mL) and pentane (50 mL) was added. The precipitated oil was washed with pentane (3×20 mL) and dried under high vacuum (3.27 g, quantitative). The product is an extremely viscous wax which solidifies completely over the course of several weeks. The following analytical data were obtained.

$^1$H NMR ($CD_2Cl_2$): δ 11.12 (s, 1H, NCHN), 7.57 (s, 2H, NCHCHN), 7.26 (t, $^3J_{H-H}$=7.7 Hz, 4H, m-CH), 6.97 (t, $^3J_{H-H}$=7.7 Hz, 2H, p-CH), 6.91 (d, $^3J_{H-H}$=8.1 Hz, 4H, o-CH), 4.84 (vt, $^3J_{H-H}$=4.8 Hz, 4H, 2×$CH_2$), 4.39 (vt, $^3J_{H-H}$=4.8 Hz, 4H, 2×$CH_2$).

$^{13}$C NMR ($CD_2Cl_2$): δ 158.03 ($OC_6H_5$ ipso C), 139.02 (NCHN), 130.00 (m-CH), 123.10 (NCHCHN), 122.09 (p-CH), 114.88 (o-CH), 66.64 ($CH_2$), 49.81 ($CH_2$).

Anal. Calcd. for $C_{19}H_{21}ClN_2O_2$ (344.87): C, 66.17; H, 6.15; N, 8.12. Found: C, 65.46; H, 6.16; N, 8.07.

A.28 Synthesis of AgCl[(PhOCHCH$_2$)$_2$Im] (28)

[(PhOCH$_2$CH$_2$)$_2$ImH]Cl (27) (3.27 g, 9.48 mmol) and Ag$_2$O (2.20 g, 9.49 mmol) were stirred overnight in dichloromethane (35 mL) in complete darkness. Dichloromethane (225 mL) was added and the mixture was stirred for approximately one hour until all precipitated material had dissolved. The solution was filtered through a plug of Celite and concentrated in vacuo to 10 mL. The precipitate was collected by vacuum filtration, washed with hexane and dried under high vacuum (3.93 g, 92%). The following analytical data were obtained.

$^1$H NMR (CD$_2$Cl$_2$): δ 7.26 (ddt, $^3J_{H-H}$=8.7 Hz, $^3J_{H-H}$=7.4 Hz, $^5J_{H-H}$=2.1 Hz, 4H, m-CH), 7.24 (s, 2H, NCHCHN), 6.95 (tt, $^3J_{H-H}$=7.4 Hz, $^4J_{H-H}$=1.0 Hz, 2H, p-CH), 6.88 (dm, $^3J_{H-H}$=8.7 Hz, 4H, o-CH), 4.52 (vt, $^3J_{H-H}$=4.8 Hz, 4H, CH$_2$), 4.27 (vt, $^3J_{H-H}$=4.8 Hz, 4H, CH$_2$).

$^{13}$C NMR (CD$_2$Cl$_2$): δ 158.41 (OC$_6$H$_5$ ipso C), 129.97 (m-CH), 122.59 (NCHCHN), 121.83 (p-CH), 114.80 (o-CH), 67.95 (CH$_2$), 52.00 (CH$_2$).

Anal. Calcd. for $C_{19}H_{20}AgClN_2O_2$ (451.73): C, 50.51; H, 4.47; N, 6.20. Found: C, 49.95; H, 4.54; N, 6.19.

A.29 Synthesis of Ru[(PhOCH$_2$CH$_2$)$_2$Im]HCl(PPh$_3$)$_2$ (29)

[(PhOCH$_2$CH$_2$)$_2$Im]AgCl (500 mg, 1.11 mmol) and RuHCl(PPh$_3$)$_3$ (972 mg, 1.05 mmol) were stirred in toluene (50 mL) for 24 hours to give a dark brown suspension. The mixture was filtered, the precipitate collected and washed with toluene (2×20 mL) and diethyl ether (2×20 mL). The precipitate was stirred overnight in dichloromethane (100 mL) to give a red solution and a brown precipitate. The supernatant was decanted and filtered through a plug of Celite and a short column of alumina. The solvent was then removed under high vacuum to give a dark red solid. This extraction was repeated twice more. The combined extracts were dissolved in dichloromethane (5 mL), filtered, and diethyl ether (10 mL) was layered on top. The mixture was allowed to stand at room temperature for 24 hours during which time dark brown crystals suitable for X-Ray diffraction separated from solution. Small amounts of colourless AgCl(PPh$_3$) occasionally crystallized with the product, which was mechanically separated and discarded. The crystals were washed with diethyl ether (2×10 mL) and dried on high vacuum (103 mg, 10%). The following analytical data were obtained.

$^1$H NMR (CD$_2$Cl$_2$): δ 7.49-7.42 (m, 12H, m-PPh$_3$), 7.321H, NCH) -7.23 (m, 18H, o-PPh$_3$ & p-PPh$_3$), 7.23-7.16 (apparent quartet, 4H, 2× m-OPh), 6.99 (d, $^3J_{H-H}$=2.1 Hz, 6.90 (t, $^3J_{H-H}$=7.4 Hz, 2H, 2×p-OPh), 6.59 (d, $^3J_{H-H}$=2.1 Hz, H, NCH), 6.52 (d, $^3J_{H-H}$=7.8 Hz, 2H, o-OPh), 6.45 (d, $^3J_{H-H}$=7.8 Hz, 2H, o-OPh), 3.95 (vt, $^3J_{H-H}$=4.9 Hz, 2H, CH$_2$), 3.52 (vt, $^3J_{H-H}$=4.9 Hz, 2H, CH$_2$), 2.73-2.64 (m, 4H, 2×CH$_2$) −32.14 (t, $^2J_{H-P}$=22.5 Hz, 1H, RuH).

$^{31}$P NMR (CD$_2$Cl$_2$): 47.06 (PPh$_3$).

$^{13}$C NMR (CD$_2$Cl$_2$): δ 158.42 (ipso-OPh), 158.25 (ipso-OPh), 137.72 (t, $^1J_{C-P}$=18.3 Hz, ipso-PPh$_3$) 134.76 (t, $J_{C-P}$=5.9 Hz, PPh$_3$), 129.72 (OPh), 129.59 (OPh), 129.33 (PPh$_3$), 128.20 (t, $J_{C-P}$=5.9 Hz, PPh$_3$), 121.37 (OPh), 121.11 (OPh) 120.56 (NCH), 120.50 (NCH), 114.84 (OPh), 114.56 (OPh), 67.40 (CH$_2$), 65.23 (CH$_2$), 49.31 (CH$_2$), 47.12 (CH$_2$).

Anal. Calcd. for $C_{55}H_{51}ClN_2O_2P_2Ru$ (970.47): C, 68.06; H, 5.31; N, 2.89. Found: C, 66.52; H, 5.19; N, 3.25.

A.30-A.33 Synthesis of RuHCl(PPh$_3$)$_2$[(CH$_3$OCH$_2$CH$_2$)2-4,5-dichloromidazol]

A.30 Synthesis of 1-(2-methoxyethyl)-1H-4,5-dichloroimidazole (30)

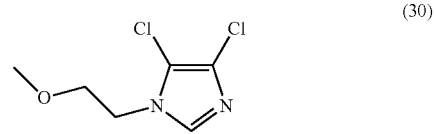

KOH (2.24 g, 40 mmol) was added to a flask equipped with dichloroimidazole (5.48 g, 40 mmol) and acetonitrile (40 mL). The mixture was then stirred at room temperature for 1 h before adding 2-bromoethyl methyl ether (5.56 g, 40 mmol) slowly. The mixture was then heated at 80° C. for 48 h. The reaction mixture was cooled to room temperature. All volatiles were removed by vacuum. The residue was added with water (20 mL). The aqueous solution was extracted by dichloromethane (3×40 mL). The organic layers were collected and dried by Na$_2$SO$_3$. Solvent was removed by vacuum to obtain brown oil (6.19 g, 79%).

$^1$H NMR (CDCl$_3$, 7.24 ppm): 3.08 (s, 3H, OMe), 3.36 (t, J=5.0 Hz, 2H, CH$_2$), 3.82 (t, J=5.0 Hz, 2H, CH$_2$), 7.22 (s, 1H, NCHN).

$^{13}$C NMR (CD$_2$Cl$_2$, 77.0 ppm): 45.83 (OMe), 58.77 (CH$_2$), 69.90 (CH$_2$), 112.76 (CCl), 125.42 (C—Cl), 132.61 (2×C—Cl), 135.16 (NCHN).

Anal. Calcd. For $C_6Cl_2N_2O$ (195.05): C, 36.95; H, 4.13; N, 14.36. Found: C, 35.85; H, 3.46; N, 15.12.

HRMS: $C_6H_9^{35}Cl_2N_2O$ (M+H) Calc. Mass: 195.0092. Found Mass: 195.0101.

A.31 Synthesis of 1,3-di(2-methoxyethyl)-4,5-dichloroimidazole bromide

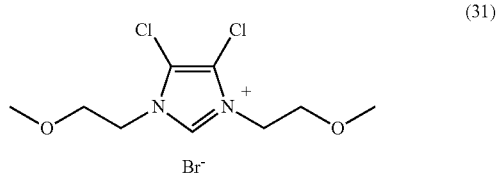

1-(2-methoxyethyl)-1H-4,5-dichloroimidazole (30) (5.00 g, 25.6 mmol) was dissolved in dry acetonitrile (10.0 mL), into which was then added 2-bromoethyl methyl ether (3.56 g, 25.6 mmol). The mixture was heated at 120° C. for 7 days. The solvent was removed by vacuum. The residue was washed with (2×5 ml) of ether. Then, the oil stuff was dried under vacuum to obtain product (8.2 g, 95%).

$^1$H NMR (CD$_2$Cl$_2$, 5.32 ppm): 3.34 (s, 6H, 2×OMe), 3.93 (t, J=4.9 Hz, 4H, 2×CH$_2$), 4.82 (t, J=4.9 Hz 4H, 2×CH$_2$), 7.61 (dd, J=6.3 Hz, J=3.2 Hz, 2×CH), 7.84 (dd, J=6.3 Hz, J=3.2 Hz, 2×CH), 11.57 (s, 1H, NCHN).

$^{13}$C NMR (CD$_2$Cl$_2$, 53.8 ppm): 47.89 (2×OMe), 59.17 (2×CH$_2$), 70.56 (2×CH$_2$), 113.97 (2×CH), 127.00 (2×CH), 132.22 (2×C), 144.34 (NCHN).

HRMS: $C_9H_{15}Cl_2N_2O_2$ (M−Br) Calc. Mass: 253.0516. Found Mass: 235.0504.

A.32 Synthesis of AgBr[(CH₃OCH₂CH₂)₂-4,5-dichloroimimidazol] (32)

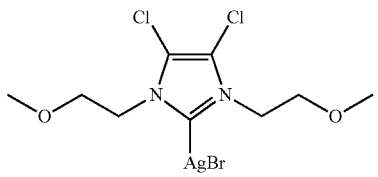

(32)

Ag₂O (0.416 g, 1.79 mmol) in methylene chloride (5 mL) was added to a solution of 1,3-di(2-methoxyethyl)-4,5-dichloroimidazole bromide (31) (1.000 g, 2.99 mmol) in methyl chloride (5 mL). The slurry solution was stirred in the dark for 14 h. The excess Ag₂O was filtered off through celite and the resulting brown solution was concentrated to 2 mL, which was then layered with pentane (10 mL). The solid precipitated was collected and dissolved in 10 mL of dichloromethane. The dichloromethane solution was then layered with 10 mL of pentane to purify the product (0.304 g, 23%).

$^1$H NMR (400 M, CD₂Cl₂, 5.32 ppm): 3.27 (s, 6H, 2×OMe), 3.69 (t, J=5.4 Hz, 4H, 2×CH₂), 4.34 (t, J=5.4 Hz, 4H, 2×CH₂).

$^{13}$C NMR (100M, CD₂Cl₂, 53.8 ppm): 50.56 (2×CH₂), 59.22 (2×OMe), 71.55 (2×CH₂), 117.80 (2×C—Cl), 184.49 (NCHN).

Anal. Calcd. For C₉H₁₄AgBrCl₂N₂O₂ (440.90): C, 24.52; H, 3.20; N, 6.35. Found: C, 24.78; H, 3.15; N, 6.72.

A.33 Synthesis of RuHCl(PPh₃)₂[(CH₃OCH₂CH₂)₂-4,5-dichloroimimidazol] (33)

AgCl[(CH₃OCH₂CH₂)₂-4,5-dichloroimidazol] (32) (0.265 g, 0.601 mmol) and RuHCl(PPh₃)₃ (0.412 g, 0.447 mmol) were combined and toluene (5 mL) was added. The suspension was stirred for 21 h at room temperature. The green solid that appeared in the solution was collected and dissolved in 18 mL of dichloromethane. The dichloromethane solution was filtered through celite plug. The filtrate was concentrated till 3 mL and layered with 5 mL of diethyl ether. The mixture was left at room temperature for overnight to get orange color crystal (0.243 g, 59%).

$^1$H NMR (400 M, CD₂Cl₂, 5.32 ppm): −22.59 (t, $J_{P-H}$=23.8 Hz, 1H, Ru—H), 2.61 (t, $J_{H-H}$=6.6 Hz, 2H, CH₂O), 2.81 (s, 3H, OCH₃), 2.87 (s, 3H, OCH₃), 3.10 (t, J=6.6 Hz, 2H, N—CH₂), 3.58 (t, J=4.1 Hz, 2H, CH₂O), 3.69 (t, J=4.1 Hz, 2H, N—CH₂), 6.63 (d, J=7.8 Hz, 1H, benzi-CH), 6.85 (d, J=7.8 Hz, 1H, benzi-CH), 6.95 (t, J=7.8 Hz, 1H, benzi-CH), 7.03 (t, J=7.8 Hz, benzi-CH), 7.09 (m, 12H, 12×CH on PPh₃), 7.23 (m, 6 H, 6×CH on PPh₃), 7.45 (broaden singlet, 12H, 12×CH on PPh₃).

$^{13}$C NMR (100 M, CD₂Cl₂, 53.8 ppm): 45.76 (CH₂), 45.83 (CH₂), 58.31 (OCH₃), 59.97 (OCH₃), 68.93 (CH₂), 73.09 (CH₂), 105.64 (CH, benzimidazlium), 108.88 (CH, benzimidazolium), 120.57 (C, benzimidazolium), 120.67 (C, benzimidazolium), 127.67 (t, J=4.1 Hz, PPh₃), 128.85 (PPh₃), 134.67 (t, J=5.6 Hz, PPh₃), 136.13 (CH, benzimidazolium), 136.21 (CH, benzimidazolium), 137.88 (t, J=17.3 Hz, PPh₃), 209.82 (td, $J_{P-C}$=11.9 Hz, $J_{C-H\ (Hydride)}$=4.4 Hz, NCN carbon).

$^{31}$P NMR (162 M, CD₂Cl₂): 44.69 (PPh₃), 44.60 (PPh₃).

Anal. Calcd. for C₄₅H₄₅Cl₃N₂O₂P₂Ru (915.23): C, 59.05; H, 4.96; N, 3.06. Found: C, 57.64; H, 4.74; N, 2.80.

B Hydrogenation Reactions

B.1 and B.2 Series 1 and 2 (Hydrogenation of NBR)

C₆H₅Cl was distilled over P₂O₅. H₂ was purified by passing through a Matheson gas drier model 450B.

In Series 1 and 2 commercially available Perbunan® T 3435 was used as nitrile rubber:

Perbunan® T3435: 34 wt % ACN; Mooney viscosity (ML 1+4 at 100° C.): 35+/−3 MU; $M_n$=80,000 g/mol; $M_w$=260,000 g/mol.

Figure 2:
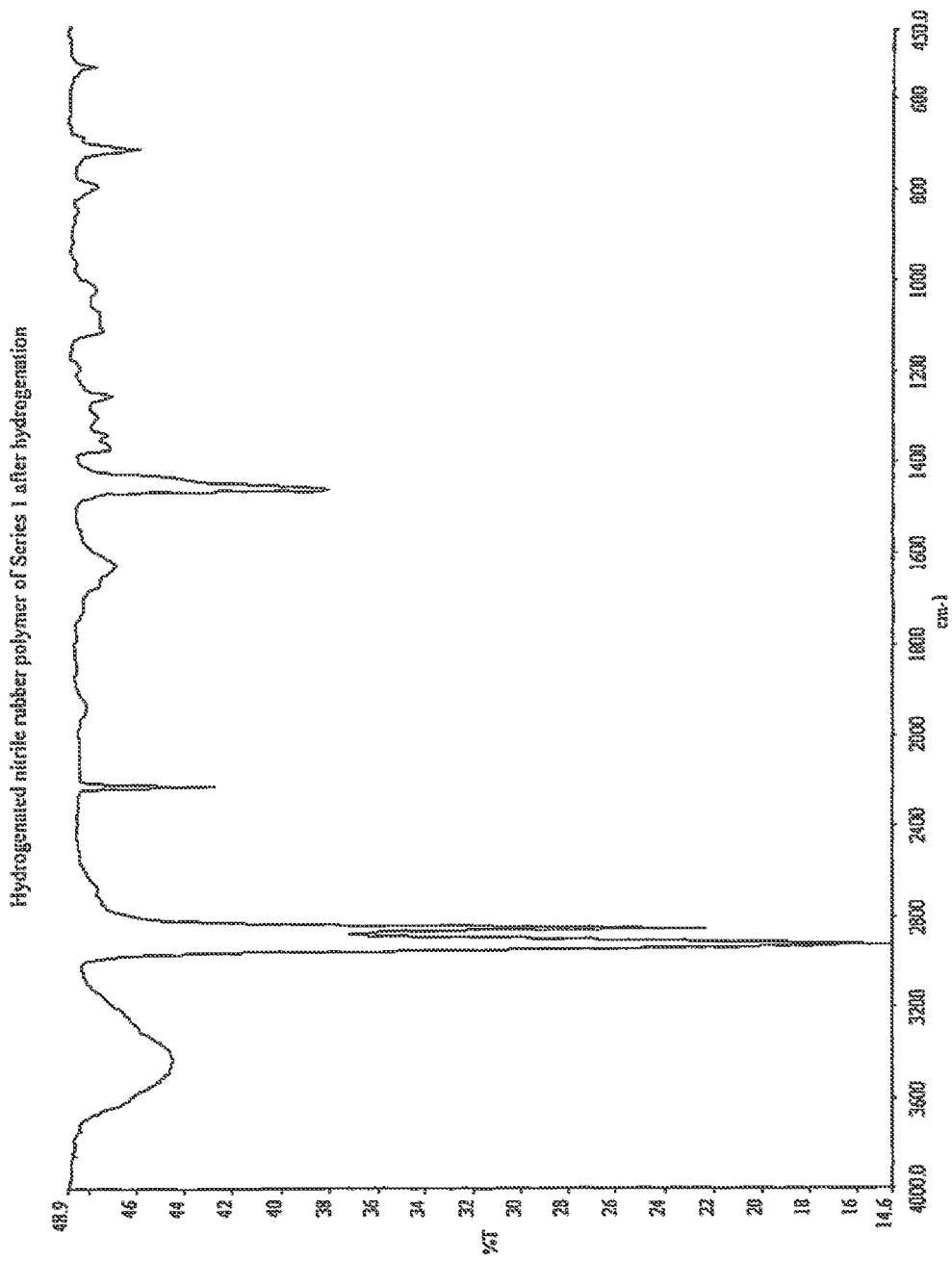
FIG. 2 shows an IR emission spectrum of the Perbunan®T 3435 after hydrogenation with a catalyst according to an embodiment of the invention.

In the glove box, the Parr reactor was charged with 10 ml of nitrile rubber solution (5 wt % in C₆H₅Cl) and RuHCl(PPh₃)((CH₃OCH₂CH₂)₂Im)(SImMes₂) (4) in an amount as listed in Table 1 (lying in the range of from 0.2 to 10 μmol). The autoclave was taken out of the glove box and purged with 10 bar H₂ for 15 seconds. The temperature was set at 80° C. and the pressure set at 40 bar of H₂. After the temperature equilibrated to 80° C. the pressure was adjusted to 50 bar, and the reaction was carried out for 20 hours under vigorous magnetic stirring. The hydrogenation run was stopped by cooling down the reactor to room temperature and venting H₂. The polymer was coagulated in methanol, filtered and dried at 50° C. under vacuum for 24 hours. Characterization of the polymer was carried out by FT-IR spectroscopy. The degree of hydrogenation was determined by IR and $^1$H NMR (Rubber Chemistry and Technology, vol 63, 244) and revealed full hydrogenation of nitrile rubber to hydrogenated nitrile rubber (see FIGS. 1 and 2). The results of the hydrogenation are summarized in Tables 1 and 2. The work up of the polymer encompassed treatment with acidic MeOH, unless otherwise indicated in the Tables. No additive was added during hydrogenation except for the comparison examples C2a and b and C3a and b in which 400 eq PPh₃ were added.

In Series 2 different catalysts were used in the amounts as outlined in Table 2 (Examples 15 to 17) and compared to non-inventive hydrogenation examples using Wilkinson's catalyst with or without PPh₃.

B.3 Series 3 (Hydrogenation of 1-hexene)

Hydrogenation Procedure (NMR Method; In-Situ Formation of the Active Catalyst, No Co-Catalyst, No Work-Up Required)

In a glove box, a sample of the appropriate metal complex (catalyst) and a deuterated solvent [CD₂Cl₂ (0.665 g) or C₆D₅Br (0.748 g)] were combined in a 2 dram vial and transferred to a J-Young tube. The respective amounts are given in Table 3. 1-hexene was added in the amount mentioned in Table 3, too, to the solution and the J-Young tube was sealed. On a schlenk line, the reaction mixture was degassed 3 times using the freeze-pump-thaw method. The sample was then frozen once more in liquid nitrogen and 4 atm of H₂ was added. The J-Young tube was sealed again and warmed to room temperature before being placed in an oil bath pre-heated to the appropriate temperature (45° C. or 100° C.). The sample was refilled with H₂ at the 4 h and 8 h time periods. NMR spectra were obtained at appropriate intervals and relative integration of substrate and product peaks were used to determine the percent composition of the mixture. The results of the hydrogenation are summarized in Table 3.

Peaks Used for Determination of Concentrations:

(The number in brackets below represents the relative number of protons represented by each peak—to determine the concentration of each the peak integrations must be normalized)

$CD_2Cl_2$ [45° C. Reactions], $C_6D_5Br$ [100° C. Reactions]
1-hexene—4.98 ppm (1)
2-hexene—5.45 ppm (1)
hexane—1.31 ppm (4)

B.4 Series 4 (Hydrogenation of Cyclohexene)
Hydrogenation Procedure (NMR Method; 5 Mol % Catalyst Based on Cyclohexene; In-Situ Formation of the Active Catalyst, No Co-Catalyst, No Work-Up Required)

In a glove box, a sample of the appropriate metal complex (catalyst) and a deuterated solvent [$CD_2Cl_2$ (0.665 g) or $C_6D_5Br$ (0.748 g)] were combined in a 2 dram vial and transferred to a J-Young tube. Twenty equivalents of cyclohexene (8.22 mg, 0.100 mmol) were added to the solution and the J-Young tube was sealed. On a schlenk line, the reaction mixture was degassed 3 times using the freeze-pump-thaw method. The sample was then frozen once more in liquid nitrogen and 4 atm of $H_2$ was added. The J-Young tube was sealed again and warmed to room temperature before being placed in an oil bath pre-heated to the appropriate temperature (45° C. or 100° C.). The sample was refilled with $H_2$ at the 4 h and 8 h time periods. NMR spectra were obtained at appropriate intervals and relative integration of substrate and product peaks were used to determine the percent composition of the mixture. The results of the hydrogenation are summarized in Table 4.

Peaks Used for Determination of Concentrations:

(The number in brackets below represents the relative number of protons represented by each peak—to determine the concentration of each the peak integrations must be normalized)

$CD_2Cl_2$ [45° C. Reactions], $C_6D_5Br$ [100° C. Reactions]
Cyclohexene—5.67 ppm (1)
Cyclohexane—1.44 ppm (6)

B.5 Series 5 (Hydrogenation of Styrene)
Hydrogenation Procedure (NMR Method; 5 Mol % Catalyst Based on Styrene; In-Situ Formation of the Active Catalyst, No Co-Catalyst, No Work-Up Required)

In a glove box, a sample of the appropriate metal complex (catalyst) (0.005 mmol) and 500 uL of deuterated solvent [$CD_2Cl_2$ (0.665 g) or $C_6D_5Br$ (0.748 g)] were combined in a 2 dram vial and transferred to a J-Young tube. Twenty equivalents of Stryene (10.45 mg, 0.100 mmol) were added to the solution and the J-Young tube was sealed. On a schlenk line, the reaction mixture was degassed 3 times using the freeze-pump-thaw method. The sample was then frozen once more in liquid nitrogen and 4 atm of $H_2$ was added. The J-Young tube was sealed again and warmed to room temperature before being placed in an oil bath pre-heated to the appropriate temperature (45° C. or 100° C.). The sample was refilled with $H_2$ at the 4 h and 8 h time periods. NMR spectra were obtained at appropriate intervals and relative integration of substrate and product peaks were used to determine the percent composition of the mixture. The results of the hydrogenation are summarized in Table 5.

Peaks Used for Determination of Concentrations:

(The number in brackets below represents the relative number of protons represented by each peak—to determine the concentration of each the peak integrations must be normalized)

$CD_2Cl_2$ [45° C. Reactions], $C_6D_5Br$ [100° C. Reactions]
Styrene—5.80 ppm (1)
Ethylbenzene—1.26 (3)

B.6 Series 6 (Hydrogenation of methyl 2-acetamidoacrylate to Demonstrate Olefin Selectivity)
Hydrogenation Procedure (NMR Method; 5 Mol % Catalyst Based on methyl 2-acetamidoacrylate; In-Situ Formation of the Active Catalyst, No Co-Catalyst, No Work-Up Required)

In a glove box, a sample of the appropriate metal complex (catalyst) (0.0056 mmol) and 500 uL of deuterated solvent [$CD_2Cl_2$ (0.665 g) were combined in a 2 dram vial and transferred to a J-Young tube. Twenty equivalents of methyl 2-acetamidoacrylate (16 mg, 0.112 mmol) were added to the solution and the J-Young tube was sealed. On a schlenk line, the reaction mixture was degassed 3 times using the freeze-pump-thaw method. The sample was then frozen once more in liquid nitrogen and 4 atm of $H_2$ was added. The J-Young tube was sealed again and warmed to room temperature before being placed in an oil bath pre-heated to the appropriate temperature (45° C.). The sample was refilled with $H_2$ at the 4 h and 8 h time periods. NMR spectra were obtained at appropriate intervals and relative integration of substrate and product peaks were used to determine the percent composition of the mixture. The results of the hydrogenation are summarized in Table 6.

Peaks Used for Determination of Concentrations (The number in brackets below represents the relative number of protons represented by each peak—to determine the concentration of each the peak integrations must be normalized)

$CD_2Cl_2$ [45° C. Reactions].
Methyl 2-acetamidoacrylate—6.52 ppm (1)
N-acetyl-alanine methyl ester—4.50 (1)

B.7 Series 7 (Hydrogenation of dimethyl-2-methylenesuccinate to Demonstrate Olefin Selectivity)
Hydrogenation Procedure (NMR Method; 5 Mol % Catalyst Based on dimethyl-2-methylenesuccinate; In-Situ Formation of the Active Catalyst, No Co-Catalyst, No Work-Up Required)

In a glove box, a sample of the appropriate metal complex (catalyst) (0.0056 mmol) and 500 uL of deuterated solvent [$CD_2Cl_2$ (0.665 g) were combined in a 2 dram vial and transferred to a J-Young tube. Twenty equivalents of dimethyl 2-methylenesuccinate (18 mg, 0.112 mmol) were added to the solution and the J-Young tube was sealed. On a schlenk line, the reaction mixture was degassed 3 times using the freeze-pump-thaw method. The sample was then frozen once more in liquid nitrogen and 4 atm of $H_2$ was added. The J-Young tube was sealed again and warmed to room temperature before being placed in an oil bath pre-heated to the appropriate temperature (45° C.). The sample was refilled with $H_2$ at the 4 h and 8 h time periods. NMR spectra were obtained at appropriate intervals and relative integration of substrate and product peaks were used to determine the percent composition of the mixture. The results of the hydrogenation are summarized in Table 7.

Peaks used for Determination of Concentrations (The number in brackets below represents the relative number of protons represented by each peak—to determine the concentration of each the peak integrations must be normalized)

$CD_2Cl_2$ [45° C. Reactions]
Dimethyl 2-methylenesuccinate—5.70 ppm (1)
Dimethyl 2-methylsuccinate—2.87 ppm (1)

B8 to B19: Series 8 to 19

Hydrogenation of Various Substrates with Different Catalysts

General Procedure:

In a glove box, a sample of the appropriate metal complex catalyst (0.005 mmol) and 500 uL of deuterated solvent [CD$_2$Cl$_2$ (0.665 g) or C$_6$D$_5$Br (0.748 g)] were combined in a 2 dram vial and transferred to a J-Young tube. Twenty equivalents of the respective substrate were added to the solution and the J-Young tube was sealed. On a schlenk line, the reaction mixture was degassed 3 times using the freeze-pump-thaw method. The sample was then frozen once more in liquid nitrogen and 4 atm of H$_2$ was added. The J-Young tube was sealed again and warmed to room temperature before being placed in an oil bath pre-heated to the appropriate temperature (45° C. or 100° C.). The sample was refilled with H$_2$ at the 4 h and 8 h time periods. NMR spectra were obtained at appropriate intervals and relative integration of substrate and product peaks were used to determine the percent composition of the mixture. The results of the hydrogenation are summarized in Tables 8-19.

B.20 Series 20

Hydrogenation of Various Substrates Using RuHCl(PPh$_3$)$_2$[(t-butyl-OCH$_2$CH$_2$)$_2$Im] (14)

The hydrogenation reactions were performed in dichloromethane-d2 under 0.4 MPa (4 atm) H$_2$ atmosphere according to the procedures described in sections B.3 (hydrogenation of 1-hexene), B4 (hydrogenation of cyclohexene), and B.7 (hydrogenation of dimethyl-2-methylene succinate) as well as described for Series 8 to 19 (including the hydrogenation of acrylonitrile (B.8) and allylamine (B.9), and phenylacetylene (B. 14)). The results are shown in Table 20.

B.21 Series 21

Hydrogenation of Various Substrates Using RuHCl(PPh$_3$)$_2$ {[(2,6-Diisopropylphenyl)-OCH$_2$CH$_2$]$_2$Im]} (18)

The hydrogenation reactions were performed in dichloromethane-d2 under 0.4 MPa (4 atm) H$_2$ atmosphere according to the procedures described in sections B.3 (hydrogenation of 1-hexene), B4 (hydrogenation of cyclohexene), and B.7 (hydrogenation of dimethyl-2-methylene succinate) as well as described for Series 8 to 19 (including the hydrogenation of acrylonitrile (B.8) and allylamine (B.9), and phenylacetylene (B.14)). The results are shown in Table 21.

B.22 Series 22

Hydrogenation of Various Substrates Using RuHCl(PPh$_3$)$_2$ [(CH$_3$OCH$_2$CH$_2$)$_2$ benzimidazole] (22)

The hydrogenation reactions were performed in dichloromethane-d2 under 0.4 MPa (4 atm) H$_2$ atmosphere according to the procedures described in sections B.3 (hydrogenation of 1-hexene), B4 (hydrogenation of cyclohexene), and B.7 (hydrogenation of dimethyl-2-methylene succinate). The results are shown in Table 22.

B.23 Series 23

Hydrogenation of 1-hexene with Ru[(t-hexyl-OCH$_2$CH$_2$)$_2$Im]HCl(PPh$_3$)$_2$ (26) and Ru[(PhOCH$_2$CH$_2$)$_2$Im]HCl(PPh$_3$)$_2$ (29), Respectively The hydrogenations reactions were performed with a loading of 5 mol % of the respective catalyst in CD$_2$Cl$_2$ at a temperature of 45° C. under 0.4 MPa (4 atm) H$_2$ pressure according to the procedure described in section B.3. The results are shown in Table 23.

B.24 Series 24

Hydrogenation of cyclohexene with Ru[(t-hexyl-OCH$_2$CH$_2$)$_2$Im]HCl(PPh$_3$)$_2$ (A.26) and Ru[(PhOCH$_2$CH$_2$)$_2$Im]HCl(PPh$_3$)$_2$ (29), ), Respectively The hydrogenation reactions were completed with a loading of 5 mol % of the respective catalyst in CD$_2$Cl$_2$ at a temperature of 45° C. under 0.4 MPa (4 atm) H$_2$ pressure according to procedures described in section B.4. The results are shown in Table 24.

B.25 Series 25

Hydrogenation of dimethyl-2-methylene succinate with Ru[(t-hexyl-OCH$_2$CH$_2$)$_2$Im]HCl(PPh$_3$)$_2$ (A.26) and Ru[(PhOCH$_2$CH$_2$)$_2$Im]HCl(PPh$_3$)$_2$ (29), ), Respectively The hydrogenation reactions were completed with a loading of 5 mol % of the respective catalyst in CD$_2$Cl$_2$ at a temperature of 45° C. under 0.4 MPa (4 atm) H$_2$ pressure according to procedures described in section B.7. The results are shown in Table 25.

In the following Tables "T" stands for reaction temperature and "p" for pressure.

TABLE 1

Series 1 - Hydrogenation of NBR (Perbunan ® T3435) (Ex. 1-14 with RuHCl(PPh$_3$) ((CH$_3$OCH$_2$CH$_2$)$_2$Im)(SIMes$_2$) (4); Comp. Ex. C1a/b and C2a/b with Wilkinson's catalyst with or without 400 eq PPh$_3$); (in all Examples: reaction time: 20 h; p = 50 bar)

| | catalyst | | | | | | | HNBR (hydrogenated nitrile rubber) | | |
|---|---|---|---|---|---|---|---|---|---|---|
| | molar | | loading | | PPh$_3$ added | T | degree of hydrogenation | Mn | Mw | |
| Example | mass (g/mol) | (µmol) | (g) | (phr) | (g) | (equiv) | (° C.) | (%) | (g/mol) | (g/mol) | PDI |
| 1 | 890.5 | 10 | 0.0089 | 1.62 | 0.55 | 0 | 80 | 99 | 54,000 | 80,200 | 1.49 |
| 2 | 890.5 | 5 | 0.0044 | 0.8 | 0.55 | 0 | 80 | 95 | 83,000 | 124,000 | 1.49 |
| 3 | 890.5 | 1 | 0.00089 | 0.162 | 0.55 | 0 | 80 | 98 | 135,000 | 358,000 | 2.65 |
| 4 | 890.5 | 0.5 | 0.00044 | 0.08 | 0.55 | 0 | 80 | 94 | 129,000 | 375,000 | 2.91 |
| 5 | 890.5 | 5 | 0.0044 | 0.8 | 0.55 | 0 | 25 | 54 | 73,000 | 117,000 | 1.6 |
| 6 | 890.5 | 1 | 0.00089 | 0.162 | 0.55 | 0 | 25 | 0 | 117,000 | 340,000 | 2.9 |
| 7 | 890.5 | 0.5 | 0.00044 | 0.08 | 0.55 | 0 | 100 | 17 | nd | nd | nd |
| 8 | 890.5 | 0.5 | 0.00044 | 0.08 | 0.55 | 0 | 120 | 18 | nd | nd | nd |
| 9 | 890.5 | 0.5 | 0.00044 | 0.08 | 0.55 | 0 | 140 | 29 | nd | nd | nd |
| 10 | 890.5 | 0.2 | 0.00018 | 0.033 | 0.55 | 1 | 80 | 10 | nd | nd | nd |
| 11 | 890.5 | 0.5 | 0.00044 | 0.08 | 0.55 | 1 | 80 | 28 | nd | nd | nd |
| 12 | 890.5 | 0.5 | 0.00044 | 0.08 | 0.55 | 1 | 100 | 30 | nd | nd | nd |
| 13 | 890.5 | 0.5 | 0.00044 | 0.08 | 0.55 | 1 | 120 | 59 | nd | nd | nd |
| 14 | 890.5 | 0.5 | 0.00044 | 0.08 | 0.55 | 1 | 140 | 29 | nd | nd | nd |
| C1a | 925.22 | 0.5 | 0.00046 | 0.083 | 0.55 | 0 | 80 | 0 | — | — | — |
| C1b | 925.22 | 0.3 | 0.00028 | 0.051 | 0.55 | 0 | 80 | 0 | — | — | — |

TABLE 1-continued

Series 1 - Hydrogenation of NBR (Perbunan ® T3435) (Ex. 1-14 with RuHCl(PPh$_3$)((CH$_3$OCH$_2$CH$_2$)$_2$Im)(SIMes$_2$) (4); Comp. Ex. C1a/b and C2a/b with Wilkinson's catalyst with or without 400 eq PPh$_3$); (in all Examples: reaction time: 20 h; p = 50 bar)

| Example | catalyst molar mass (g/mol) | catalyst loading (µmol) | catalyst loading (g) | catalyst loading (phr) | NBR (g) | PPh$_3$ added (equiv) | T (° C.) | degree of hydrogenation (%) | HNBR Mn (g/mol) | HNBR Mw (g/mol) | PDI |
|---|---|---|---|---|---|---|---|---|---|---|---|
| C2a | 925.22 | 0.5 | 0.00046 | 0.083 | 0.55 | 400 | 80 | 100 | 133,083 | 380,072 | 2.85 |
| C2b | 925.22 | 0.5 | 0.00046 | 0.083 | 0.55 | 400 | 80 | 100 | 129,242 | 337,588 | 2.61 |

TABLE 2

Series 2 - Hydrogenation of NBR (Examples 15-17 with different catalysts; Comp. Ex. C3a/C3b and C3c/C3d with Wilkinson's catalyst without or in combination with 400 eq PPh$_3$); (in all Examples: reaction time: 20 h; T = 80° C.; p = 50 bar)

| Example | Catalyst Structure | Loading (µmol) | Loading (g) | Loading (phr) | NBR (g) | Additive (mg; unless indicated otherwise) |
|---|---|---|---|---|---|---|
| 15a | RuHCl(PPh$_3$)$_2$[(CH$_3$—OCH$_2$CH$_2$)$_2$Im] (3) | 5 | 0.0042 | 0.64 | 0.55 | BHT (100) |
| 15b | (Molar Mass: | 5 | 0.0042 | 0.764 | 0.55 | BHT (100) |
| 15c | 846.34 g/mol) | 5 | 0.0042 | 0.764 | 0.55 | none |
| 15d | | 5 | 0.0042 | 0.764 | 0.55 | none |
| 15e | | 5 | 0.0042 | 0.764 | 0.55 | none |
| 15f | | 2.5 | 0.0021 | 0.382 | 0.55 | none |
| 16a | [RuH(O(CH$_2$CH$_2$ImCH$_3$)$_2$(PPh$_3$)$_2$]$^+$[AgBr$_2$]$^-$ (8) | 5 | 0.0056 | 1.018 | 0.55 | none |
| 16b | (Molar Mass: 1128.63 g/mol) | 5 | 0.0056 | 1.018 | 0.55 | none |
| 17a | [RuH((CH$_3$O(CH$_2$)$_2$Im)(SIMes$_2$)][(η$^6$-Ph)BPh$_3$] | 5 | 0.0046 | 0.836 | 0.55 | none |
| 17b | (7) (Molar Mass: 911.98 g/mol) | 1 | 0.00091 | 0.165 | 0.55 | none |
| C3a | Wilkinson's Catalyst (Molar Mass: | 0.5 | 0.00046 | 0.083 | 0.55 | PPh$_3$ (400 eq) |
| C3b | 925.22 g/mol) | 0.5 | 0.00046 | 0.083 | 0.55 | PPh$_3$ (400 eq) |
| C3c | | 0.5 | 0.00046 | 0.083 | 0.55 | none |
| C3d | | 0.3 | 0.00028 | 0.051 | 0.55 | none |

| Example | workup | degree of hydrogenation of soluble fraction (%) | HNBR Mn (g/mol) | HNBR Mw (g/mol) | PDI | degree of hydrogenation of solid fraction (%) |
|---|---|---|---|---|---|---|
| 15a | acidic methanol | 42 | 58,274 | 158,205 | 2.72 | 81 |
| 15b | vacuum 50° C. | 42 | 60,511 | 245,169 | 4.05 | 81 |
| 15c | acidic methanol | 2 | 43,683 | 96,272 | 2.2 | 90 |
| 15d | vacuum 50° C. | 2 | 43,431 | 97,372 | 2.24 | 90 |
| 15e | acidic methanol | 97 | Insoluble material | | | |
| 15f | acidic methanol | 63 | 47,578 | 111,693 | 2.35 | |
| 16a | acidic methanol | 23 | 36,358 | 91,978 | 2.53 | |
| 16b | acidic methanol | 73 | Insoluble material | | | |
| 17a | acidic methanol | 99 | 56,594 | 96,049 | 1.7 | |
| 17b | acidic methanol | 99 | 115,152 | 329,202 | 2.85 | |

TABLE 2-continued

Series 2 - Hydrogenation of NBR (Examples 15-17 with different catalysts; Comp. Ex. C3a/C3b and C3c/C3d with Wilkinson's catalyst without or in combination with 400 eq $PPh_3$); (in all Examples: reaction time: 20 h; T = 80° C.; p = 50 bar)

| | | | | | | |
|---|---|---|---|---|---|---|
| C3a | acidic methanol | 100 | 133,083 | 380,072 | 2.85 | n/a |
| C3b | vaccum 50° C. | 100 | 129,242 | 337,588 | 2.61 | n/a |
| C3c | acidic methanol | 0 | — | — | — | |
| C3d | acidic methanol | 0 | — | — | — | |

TABLE 3

Series 3 - Hydrogenation of 1-hexene (Examples 18 to 21 with different catalysts; Comp. Ex. C4 and C5 with Wilkinson's catalyst and $RuHCl(PPh_3)_3$, respectively); (in all Examples: p = 4 bar)

| Example | Catalyst Metal Complex | loading (mg) | loading (mol %) | 1-hexene (mg) | solvent | solvent (g) | T (° C.) | Time (h) | 1-hexene (%) | 2-hexene (%) | hexane (%) |
|---|---|---|---|---|---|---|---|---|---|---|---|
| 18a | $RuHCl(PPh_3)((CH_3O{-}CH_2CH_2)_2Im)$- | 4.45 | 5 | 10.51 | $CD_2Cl_2$ | 0.681 | 45 | 4 | 0 | 53 | 47 |
| 18b | $(SIMes_2)$ | | | | | | | 6 | 0 | 41.5 | 58.5 |
| 18c | (4) | | | | | | | 8 | 0 | 29.6 | 70.4 |
| 18d | (Molar Mass: | | | | | | | 24 | 0 | 0 | 100 |
| 18e | 890.5 g/mol) | 15 | 5 | 27.7 | $CD_5Br$ | 0.77 | 100 | 4 | 0 | 87 | 13 |
| 18f | | | | | | | | 24 | 0 | 70 | 30 |
| 19a | $RuHCl(PPh_3)_2[(CH_3O{-}(CH_2)_2Im]$ | 4.23 | 5 | 8.41 | $CD_2Cl_2$ | 0.681 | 45 | 4 | 19.8 | 5.5 | 74.7 |
| 19b | (3) | | | | | | | 8 | 0 | 6.2 | 93.8 |
| 19c | (Molar Mass: | | | | | | | 24 | 0 | 0 | 100 |
| 19d | 846.34 g/mol) | 15 | 5 | 27.7 | $CD_5Br$ | 0.77 | 100 | 4 | 37 | 46 | 17 |
| 19e | | | | | | | | 48 | 9 | 51 | 40 |
| 20a | $[RuH((CH_3O(CH_2)_2)_2Im)$- | 4.56 | 5 | 8.41 | $CD_2Cl_2$ | 0.681 | 45 | 2 | 84.7 | 0 | 15.3 |
| 20b | $(SIMes_2)][(\eta^6\text{-}Ph)BPh_3]$ | | | | | | | 4 | 69.6 | 4.9 | 25.5 |
| 20c | (7) | | | | | | | 6 | 30 | 31.6 | 38.4 |
| 20d | (Molar Mass: | | | | | | | 24 | 0 | 0 | 100 |
| 20e | 911.98 g/mol) | | | | $CD_5Br$ | 0.77 | 100 | 2 | 0 | 69.7 | 30.3 |
| 20f | | | | | | | | 4 | 0 | 59.3 | 40.7 |
| 20g | | | | | | | | 6 | 0 | 48.8 | 51.2 |
| 20h | | | | | | | | 24 | 0 | 40.5 | 59.5 |
| 21a | $[RuH(O(CH_2CH_2ImCH_3)_2{-}(PPh_3)_2]^+$ | 15 | 5 | 27.7 | $CD_2Cl_2$ | 0.681 | 45 | 4 | 85 | 2 | 13 |
| 21b | $[AgBr_2]^-$ | | | | | | | 24 | 0 | 45 | 55 |
| 21c | (8) | | 5 | 27.7 | $CD_5Br$ | 0.77 | 100 | 4 | 6 | 65 | 29 |
| 21d | (Molar Mass: 1128.63 g/mol) | | | | | | | 24 | 0 | 62 | 38 |
| C4a | $RhCl(PPh_3)_3$ | 4.63 | 5 | 8.41 | $CD_2Cl_2$ | 0.681 | 45 | 2 | 19.2 | 8.6 | 72.2 |
| C4b | (Wilkinson's Catalyst) | | | | | | | 4 | 0 | 4.8 | 95.2 |
| C4c | | | | | | | | 6 | 0 | 0 | 100 |
| C4d | | | | | | $CD_5Br$ | 0.770 | 100 | 2 | 0 | 57.7 | 42.3 |
| C4e | | | | | | | | 4 | 0 | 45 | 55 |
| C4f | | | | | | | | 6 | 0 | 22.8 | 77.2 |
| C4g | | | | | | | | 24 | 0 | 0 | 100 |
| C5a | $RuHCl(PPh_3)_3$ | 4.62 | 5 | 8.41 | $CD_2Cl_2$ | 0.681 | 45 | 2 | 0 | 31.3 | 68.7 |
| C5b | | | | | | | | 4 | 0 | 16.9 | 83.1 |
| C5c | | | | | | | | 6 | 0 | 11.3 | 88.7 |
| C5d | | | | | | | | 24 | 0 | 8.6 | 91.4 |
| C5e | | | | | | $CD_5Br$ | 0.770 | 100 | 2 | 29 | 28.7 | 42.3 |
| C5f | | | | | | | | 4 | 25.2 | 23.3 | 52.5 |
| C5g | | | | | | | | 6 | 20.2 | 24.0 | 55.8 |
| C5h | | | | | | | | 24 | 11.6 | 25.1 | 63.3 |

TABLE 4

Series 4 - Hydrogenation of cyclohexene (Examples 22-25 with different catalysts according to the invention, Comp. Ex. C6 and C7 with Wilkinson's catalyst and $RuHCl(PPh_3)_3$, respectively); (in all Examples: p = 4 bar)

| Examples | catalyst metal complex | loading (mg) | loading (mol %) | cyclohexene (mg) | solvent | solvent (g) | T (° C.) | Time (h) | cyclohexene (%) | cyclohexane (%) |
|---|---|---|---|---|---|---|---|---|---|---|
| 22a | $RuHCl(PPh_3)((CH_3OCH_2CH_2)_2Im)$- | 4.45 | 5 | 8.22 | $CD_2Cl_2$ | 0.681 | 45 | 4 | 87 | 13 |
| 22b | $(SIMes_2)$ | | | | | | | 6 | 78.5 | 21.5 |

TABLE 4-continued

Series 4 - Hydrogenation of cyclohexene (Examples 22-25 with different catalysts according to the invention, Comp. Ex. C6 and C7 with Wilkinson's catalyst and RuHCl(PPh$_3$)$_3$, respectively); (in all Examples: p = 4 bar)

| | catalyst | | | cyclo- | | | | | cyclo- | cyclo- |
|---|---|---|---|---|---|---|---|---|---|---|
| Examples | metal complex | loading (mg) | loading (mol %) | hexene (mg) | solvent | solvent (g) | T (° C.) | Time (h) | hexene (%) | hexane (%) |
| 22c | (4) | | | | | | | 8 | 72.1 | 27.9 |
| 22d | | | | | | | | 24 | 46.9 | 53.1 |
| 22e | | | | | | | | 48 | 16.5 | 83.5 |
| 22f | | | | | | | | 72 | 0 | 100 |
| 22g | | 15 | 5 | 29.3 | CD$_5$Br | 0.77 | 100 | 2 | 94 | 6 |
| 22h | | | | | | | | 24 | 89 | 11 |
| 23a | RuHCl(PPh$_3$)$_2$[(CH$_3$OCH$_2$CH$_2$)$_2$Im] | 4.23 | 5 | 8.22 | CD$_2$Cl$_2$ | 0.681 | 45 | 4 | 93.1 | 6.9 |
| 23b | (3) | | | | | | | 6 | 87.2 | 12.8 |
| 23c | | | | | | | | 8 | 79.6 | 20.4 |
| 23d | | | | | | | | 24 | 32.1 | 67.9 |
| 23e | | | | | | | | 48 | 11.3 | 88.7 |
| 23f | | | | | | | | 72 | 0 | 100 |
| 23g | | 15 | 5 | 29.1 | CD$_5$Br | 0.77 | 100 | 2 | 95 | 5 |
| 23h | | | | | | | | 48 | 81 | 19 |
| 24a | [RuH((CH$_3$OCH$_2$CH$_2$)$_2$Im)(SIMes$_2$)]-[($\eta^6$- | 4.56 | 5 | 8.22 | CD$_2$Cl$_2$ | 0.681 | 45 | 2 | 96.2 | 3.8 |
| 24b | Ph)BPh$_3$] | | | | | | | 4 | 90.1 | 9.9 |
| 24c | (7) | | | | | | | 6 | 86.1 | 13.9 |
| 24d | | | | | | | | 8 | 82.6 | 17.4 |
| 24e | | | | | | | | 24 | 56.8 | 43.2 |
| 24f | | | 5 | 27 | CD$_5$Br | 0.77 | 100 | 2 | 89.3 | 10.7 |
| 24g | | | | | | | | 4 | 85.5 | 14.5 |
| 24h | | | | | | | | 6 | 84 | 16 |
| 24i | | | | | | | | 8 | 83.8 | 16.2 |
| 24k | | | | | | | | 24 | 82.6 | 17.4 |
| 25a | [RuH(O(CH$_2$CH$_2$ImCH$_3$)$_2$(PPh$_3$)$_2$]$^+$[AgBr$_2$]$^-$ | 15 | 5 | 27 | CD$_2$Cl$_2$ | 0.681 | 45 | 4 | n/a | — |
| 25b | (8) | | | | | | | 24 | n/a | — |
| 25c | | | 5 | 27 | CD$_5$Br | 0.77 | 100 | 4 | 92 | 8 |
| 25d | | | | | | | | 24 | 81 | 19 |
| C6a | RhCl(PPh$_3$)$_3$ | 4.63 | 5 | 8.22 | CD$_2$Cl$_2$ | 0.681 | 45 | 2 | 24.1 | 75.9 |
| C6b | (Wilkinson's Catalyst) | | | | | | | 4 | 0 | 100 |
| C6c | | | | | CD$_5$Br | 0.77 | 100 | 2 | 69.4 | 30.6 |
| C6d | | | | | | | | 4 | 52.1 | 47.9 |
| C6e | | | | | | | | 6 | 33 | 67 |
| C6f | | | | | | | | 8 | 18.6 | 81.4 |
| C6g | | | | | | | | 24 | 3 | 97 |
| C7a | RuHCl(PPh$_3$)$_3$ | 4.62 | 5 | 8.22 | CD$_2$Cl$_2$ | 0.681 | 45 | 2 | 63.2 | 36.8 |
| C7b | | | | | | | | 4 | 41.3 | 58.7 |
| C7c | | | | | | | | 6 | 27.2 | 72.8 |
| C7d | | | | | | | | 8 | 15.6 | 84.4 |
| C7e | | | | | | | | 24 | 0 | 100 |
| C7f | | | | | CD$_5$Br | 0.77 | 100 | 2 | 98.1 | 1.9 |
| C7g | | | | | | | | 4 | 98.1 | 1.9 |
| C7h | | | | | | | | 6 | 98.1 | 1.9 |

TABLE 5

Series 5 - Hydrogenation of Styrene (Examples 26-29 with different catalysts, Comp. Ex. C8 and C9 with Wilkinson's catalyst and RuHCl(PPh$_3$)$_3$, respectively); (in all Examples: p = 4 bar)

| | catalyst | | | | | | | | | ethyl- |
|---|---|---|---|---|---|---|---|---|---|---|
| Example | metal complex | loading (mg) | loading (mol %) | styrene (mg) | solvent | solvent (g) | T (° C.) | time (h) | styrene (%) | benzene (%) |
| 26a | RuHCl(PPh$_3$) | 4.45 | 5 | 10.45 | CD$_2$Cl$_2$ | 0.681 | 45 | 2 | 45.7 | 54.3 |
| 26b | ((CH$_3$OCH$_2$CH$_2$)$_2$Im) | | | | | | | 4 | 11 | 89 |
| 26c | (SIMes$_2$) | | | | | | | 6 | 0 | 100 |
| 26d | (4) | 15 | 5 | 37.2 | CD$_5$Br | 0.77 | 100 | 2 | 83 | 17 |
| 26e | | | | | | | | 24 | 67 | 33 |
| 27a | RuHCl(PPh$_3$)$_2$ | 4.23 | 5 | 10.45 | CD$_2$Cl$_2$ | 0.681 | 45 | 4 | 44 | 56 |
| 27b | [(CH$_3$OCH$_2$CH$_2$)$_2$Im] | | | | | | | 6 | 12.4 | 87.6 |
| 27c | (3) | | | | | | | 8 | 3 | 97 |
| 27d | | | | | | | | 24 | 0 | 100 |
| 27f | | 15 | 5 | 37.2 | CD$_5$Br | 0.77 | 100 | 2 | 83 | 17 |
| 27g | | | | | | | | 24 | 63 | 37 |
| 27h | | 5 | 5 | 10.45 | CD$_5$Br | 0.77 | 100 | 2 | 77 | 23 |
| 27i | | | | | | | | 24 | 41 | 59 |
| 28a | [RuH((CH$_3$OCH$_2$CH$_2$)$_2$Im) | 4.56 | 5 | 10.45 | CD$_2$Cl$_2$ | 0.681 | 45 | 2 | 87 | 13 |

TABLE 5-continued

Series 5 - Hydrogenation of Styrene (Examples 26-29 with different catalysts, Comp. Ex. C8 and C9 with Wilkinson's catalyst and RuHCl(PPh$_3$)$_3$, respectively); (in all Examples: p = 4 bar)

| Example | catalyst metal complex | loading (mg) | loading (mol %) | styrene (mg) | solvent | solvent (g) | T (° C.) | time (h) | styrene (%) | ethyl-benzene (%) |
|---|---|---|---|---|---|---|---|---|---|---|
| 28b | (SIMes$_2$)] [($\eta^6$-Ph)BPh$_3$] | | | | | | | 4 | 79 | 21 |
| 28c | (7) | | | | | | | 6 | 57 | 43 |
| 28d | | | | | | | | 24 | 0 | 100 |
| 28e | | | | | 10.45 | CD$_5$Br | 0.77 | 100 | 2 | 60 | 40 |
| 28f | | | | | | | | | 4 | 44 | 56 |
| 28g | | | | | | | | | 6 | 13 | 87 |
| 28h | | | | | | | | | 24 | 0 | 100 |
| 29a | [RuH(O(CH$_2$)$_2$ImCH$_3$)$_2$(PPh$_3$)$_2$]$^+$ | 15 | 5 | 37.2 | CD$_2$Cl$_2$ | 0.681 | 45 | 4 | n/a | — |
| 29b | [AgBr$_2$]$^-$ | | | | | | | 24 | n/a | |
| 29c | (8) | | 5 | 37.2 | CD$_5$Br | 0.77 | 100 | 4 | 77 | 23 |
| 29d | | | | | | | | 24 | 46 | 54 |
| C8a | RhCl(PPh$_3$)$_3$ | 4.45 | 5 | 10.45 | CD$_2$Cl$_2$ | 0.681 | 45 | 2 | 4.1 | 95.9 |
| C8b | (Wilkinson's Catalyst) | | | | | | | 4 | 0 | 100 |
| C8c | | | | 10.45 | CD$_5$Br | 0.77 | 100 | 2 | 32.4 | 67.6 |
| C8d | | | | | | | | 4 | 25.0 | 75.0 |
| C8e | | | | | | | | 6 | 0 | 100 |
| C9a | RuHCl(PPh$_3$)$_3$ | 4.62 | 5 | 10.45 | CD$_2$Cl$_2$ | 0.681 | 45 | 2 | 18.9 | 81.1 |
| C9b | | | | | | | | 4 | 0 | 100 |
| C9c | | | | 10.45 | CD$_5$Br | 0.77 | 100 | 2 | 58.7 | 41.3 |
| C9d | | | | | | | | 4 | 56.2 | 43.8 |
| C9e | | | | | | | | 6 | 45.8 | 54.2 |
| C9f | | | | | | | | 24 | 8.3 | 91.7 |

TABLE 6

Series 6 (Hydrogenation of methyl 2-acetamidoacrylate; to demonstrate olefin selectivity); (in all Examples: p = 4 bar and T = 45° C.)

| Example | catalyst metal complex | loading (mg) | loading (mol %) | methyl 2-acetamido-acrylate (mg) | solvent | solvent (g) | time (h) | methyl 2-acetamido-acrylate (%) | N-acetyl-alanine methyl ester (%) |
|---|---|---|---|---|---|---|---|---|---|
| 30a | RuHCl(PPh$_3$) | 5.0 | 5 | 16.0 | CD$_2$Cl$_2$ | 0.681 | 2 | 49 | 51 |
| 30b | ((CH$_3$OCH$_2$CH$_2$)$_2$Im) | | | | | | 6 | 6 | 94 |
| 30c | (SIMes$_2$) (4) | | | | | | 24 | 0 | 100 |

TABLE 7

Series 7 (Hydrogenation of dimethyl 2-methylenesuccinate; to demonstrate olefin selectivity); (in all Examples: p = 4 bar; T = 45° C.)

| Example | catalyst metal complex | loading (mg) | loading (mol %) | dimethyl 2-methylene-succinate (mg) | solvent | solvent (g) | time (h) | dimethyl-2-methylene-succinate (%) | dimethyl-2-methyl-succinate (%) |
|---|---|---|---|---|---|---|---|---|---|
| 31a | RuHCl(PPh$_3$) | 5.0 | 5 | 18.0 | CD$_2$Cl$_2$ | 0.681 | 4 | 58 | 42 |
| 31b | ((CH$_3$OCH$_2$CH$_2$)$_2$Im) | | | | | | 8 | 21 | 79 |
| 31c | (SIMes$_2$) (4) | | | | | | 24 | 0 | 100 |

TABLE 8

Series 8 (Hydrogenation of acrylonitrile; to demonstrate olefin selectivity);
(in all Examples: P = 4 bar and T = 45° C.)

| | catalyst | | | | | | | propio- |
|---|---|---|---|---|---|---|---|---|
| Example | metal complex | loading (mg) | loading (mol %) | acrylonitrile (mg) | solvent | solvent (g) | time (h) | acrylonitrile (%) | nitrile (%) |
| 32a | RuHCl(PPh$_3$) | 5.0 | 5 | 6.0 | CD$_2$Cl$_2$ | 0.681 | 4 | 45 | 55 |
| 32b | ((CH$_3$OCH$_2$CH$_2$)$_2$Im) | | | | | | 8 | 12 | 88 |
| 32c | (SIMes$_2$) (4) | | | | | | 24 | 0 | 100 |

TABLE 9

Series 9 (Hydrogenation of allylamine; to demonstrate olefin selectivity);
(in all Examples: p = 4 bar and T = 45° C.)

| | catalyst | | | | | | | propyl- |
|---|---|---|---|---|---|---|---|---|
| Example | metal domplex | loading (mg) | loading (mol %) | allylamine (mg) | solvent | solvent (g) | time (h) | allylamine (%) | amine (%) |
| 33a | RuHCl(PPh$_3$) | 5.0 | 5 | 6.4 | CD$_2$Cl$_2$ | 0.681 | 4 | 20 | 80 |
| 33b | ((CH$_3$OCH$_2$CH$_2$)$_2$Im) | | | | | | 8 | 7 | 93 |
| 33c | (SIMes$_2$) (4) | | | | | | 24 | 0 | 100 |

TABLE 10

Series 10 (Hydrogenation of allylalcohol; to demonstrate olefin selectivity;
(in all Examples: p = 4 bar and T = 45° C.)

| | catalyst | | | allyl- | | | | allyl- | |
|---|---|---|---|---|---|---|---|---|---|
| Example | metal complex | loading (mg) | loading (mol %) | alcohol (mg) | solvent | solvent (g) | time (h) | alcohol (%) | Propanol (%) |
| 34a | RuHCl(PPh$_3$) ((CH$_3$OCH$_2$CH$_2$)$_2$Im) (SIMes$_2$) (4) | 5.0 | 5 | 6.5 | CD$_2$Cl$_2$ | 0.681 | 4 | 0 | 100 |

TABLE 11

Series 11 (Hydrogenation of Phenylvinylsulfone; to demonstrate olefin selectivity);
(in all Examples: p = 4 bar and T = 45° C.)

| | catalyst | | | phenyl-vinyl- | | | | phenyl-vinyl- | ethylvinyl- |
|---|---|---|---|---|---|---|---|---|---|
| Example | metal complex | loading (mg) | loading (mol %) | sulfone (mg) | solvent | solvent (g) | time (h) | sulfone (%) | sulfone (%) |
| 35a | RuHCl(PPh$_3$) | 5.0 | 5 | 19.0 | CD$_2$Cl$_2$ | 0.681 | 4 | 37 | 63 |
| 35b | ((CH$_3$OCH$_2$CH$_2$)$_2$Im) | | | | | | 8 | 15 | 85 |
| 35c | (SIMes$_2$) (4) | | | | | | 24 | 0 | 100 |

TABLE 12

Series 12 (Hydrogenation of 2-vinylpyridine to demonstrate olefin selectivity); (in all Examples: p = 4 bar and T = 45° C.)

| Example | catalyst metal complex | loading (mg) | loading (mol %) | 2-vinyl-pyridine (mg) | solvent | solvent (g) | time (h) | 2-vinyl-pyridine (%) | 2-ethyl-pyridine (%) |
|---|---|---|---|---|---|---|---|---|---|
| 36a | RuHCl(PPh$_3$)((CH$_3$OCH$_2$CH$_2$)$_2$Im)(SIMes$_2$) (4) | 4.45 | 5 | 10.51 | CD$_2$Cl$_2$ | 0.681 | 4 | 0 | 100 |

TABLE 13

Series 13 (Hydrogenation of 1-vinylimidazole to demonstrate olefin selectivity); (in all Examples: p = 4 bar and T = 45° C.)

| Example | catalyst metal complex | loading (mg) | loading (mol %) | 1-vinyl-imidazole (mg) | solvent | solvent (g) | time (h) | 1-vinyl-imidazole (%) | 1-ethyl-imidazole (%) |
|---|---|---|---|---|---|---|---|---|---|
| 37a | RuHCl(PPh$_3$)((CH$_3$OCH$_2$CH$_2$)$_2$Im)(SIMes$_2$) (4) | 4.45 | 5 | 9.41 | CD$_2$Cl$_2$ | 0.681 | 4 | 37 | 63 |
| 37b | | | | | | | 8 | 5 | 95 |
| 37c | | | | | | | 24 | 0 | 100 |

TABLE 14

Series 14 (Hydrogenation of acrylaldehyde to demonstrate olefin selectivity); (in all Examples: p = 4 bar and T = 45° C.)

| Example | catalyst metal complex | loading (mg) | loading (mol %) | acryl-aldehyde (mg) | solvent | solvent (g) | time (h) | acryl-aldehyde (%) | propion-aldehyde (%) |
|---|---|---|---|---|---|---|---|---|---|
| 38a | RuHCl(PPh$_3$)((CH$_3$OCH$_2$CH$_2$)$_2$Im)(SIMes$_2$) (4) | 4.45 | 5 | 5.61 | CD$_2$Cl$_2$ | 0.681 | 4 | 37 | 63 |
| 38b | | | | | | | 8 | 0 | 100 |

TABLE 15

Series 15 (Hydrogenation of 3-buten-2-one to demonstrate olefin selectivity); (in all Examples: p = 4 bar and T = 45° C.)

| Example | catalyst metal complex | loading (mg) | loading (mol %) | 3-buten-2-one (mg) | solvent | solvent (g) | time (h) | 3-buten-2-one (%) | 2-butanone (%) |
|---|---|---|---|---|---|---|---|---|---|
| 39a | RuHCl(PPh$_3$)((CH$_3$OCH$_2$CH$_2$)$_2$Im)(SIMes$_2$) (4) | 5.0 | 5 | 7.9 | CD$_2$Cl$_2$ | 0.681 | 4 | 0 | 100 |

TABLE 16

Series 16 (Hydrogenation of Phenylvinylthioether to demonstrate olefin selectivity);
(in all Examples: p = 4 bar and T = 45° C.)

| Example | catalyst metal complex | loading (mg) | loading (mol %) | phenyl-vinyl-thioether (mg) | solvent | solvent (g) | time (h) | phenyl-vinyl-thioether (%) | phenyl-ethyl-thioether (%) |
|---|---|---|---|---|---|---|---|---|---|
| 40a | RuHCl(PPh$_3$) | 4.45 | 5 | 13.62 | CD$_2$Cl$_2$ | 0.681 | 4 | 39 | 61 |
| 40b | ((CH$_3$OCH$_2$CH$_2$)$_2$Im) | | | | | | 8 | 2 | 98 |
| 40c | (SIMes$_2$) | | | | | | 24 | 0 | 100 |
| | (4) | | | | | | | | |

TABLE 17

Series 17 (Hydrogenation of methyl 3-butenoate to demonstrate olefin selectivity);
(in all Examples: p = 4 bar and T = 45° C.)

| Example | catalyst metal complex | loading (mg) | loading (mol %) | methyl 3-butenoate (mg) | solvent | solvent (g) | time (h) | methyl-3-butenoate (%) | methyl-butyrate (%) |
|---|---|---|---|---|---|---|---|---|---|
| 41a | RuHCl(PPh$_3$) | 5.0 | 5 | 12.8 | CD$_2$Cl$_2$ | 0.681 | 4 | 8 | 92 |
| 41b | ((CH$_3$OCH$_2$CH$_2$)$_2$Im) (SIMes$_2$) (4) | | | | | | 8 | 0 | 100 |

TABLE 18

Series 18 (Hydrogenation of 2,3-dimethyl-2-butene to demonstrate olefin selectivity);
(in all Examples: p = 4 bar and T = 45° C.)

| Example | catalyst metal complex | loading (mg) | loading (mol %) | 2,3-dimethyl-2-butene (mg) | solvent | solvent (g) | time (h) | 2,3-dimethyl-2-butene (%) | 2,3-dimethyl-butane (%) |
|---|---|---|---|---|---|---|---|---|---|
| 42a | RuHCl(PPh$_3$) | 5.0 | 5 | 9.4 | CD$_2$Cl$_2$ | 0.681 | 4 | 99 | <1 |
| 42b | ((CH$_3$OCH$_2$CH$_2$)$_2$Im) | | | | | | 8 | 99 | <1 |
| 42c | (SIMes$_2$) | | | | | | 24 | 99 | <1 |
| | (4) | | | | | | | | |

TABLE 19

Series 19 (Hydrogenation of phenylacetylene to demonstrate olefin selectivity);
(in all Examples: p = 4 bar and T = 45° C.)

| Example | catalyst metal complex | loading (mg) | loading (mol %) | phenyl-acetylene (mg) | solvent | solvent (g) | time (h) | phenyl-acetylene (%) | styrene [ethylbenzene] (%) |
|---|---|---|---|---|---|---|---|---|---|
| 41a | RuHCl(PPh$_3$) | 5.0 | 5 | 11. | CD$_2$Cl$_2$ | 0.81 | 4 | 0 | 50[50] |
| 41b | ((CH$_3$OCH$_2$CH$_2$)$_2$Im) (SIMes$_2$) (4) | | | | | | 8 | 0 | 0[100] |

TABLE 20

Series 20 (hydrogenation of various substrates using 5 mol % RuHCl(PPh$_3$)$_2$ [(t-butyl-OCH$_2$CH$_2$)$_2$Im] (A.14) in DCM-d2, 4 atm H$_2$-atmosphere)

| substrate | temperature (° C.) | time (h) | product(s) | conversion (%) |
|---|---|---|---|---|
| 1-hexene | 45 | 4 | hexane (2-hexene) | 89 (11) |
|  |  | 8 |  | 91 (9) |
|  |  | 24 |  | 96 (4) |
| phenylacetylene | 45 | 4 | styrene(ethylbenzene) | 76 (10) |
|  |  | 8 |  | 78 (22) |
|  |  | 24 |  | 0 (100) |
| acrylonitrile | 45 | 4 | propionitrile | 56 |
|  |  | 8 |  | 71 |
|  |  | 24 |  | 100 |
| allyamine | 45 | 4 | propylamine | 77 |
|  |  | 8 |  | 94 |
|  |  | 24 |  | 100 |
| cyclohexene | 45 | 4 | cyclohexane | 59 |
|  |  | 8 |  | 82 |
|  |  | 24 |  | 100 |
| dimethyl-2-methylene succinate | 45 | 4 | dimethyl methylsuccinate | 69 |
|  |  | 8 |  | 83 |
|  |  | 24 |  | 100 |

TABLE 21

Series 21 (hydrogenation of various substrates with 5 mol % RuHCl(PPh$_3$)$_2${[(2,6-Diisopropylphenyl)-OCH$_2$CH$_2$]$_2$Im]} (18) in DCM-d2, 4 atm H$_2$ atmosphere)

| substrate | temperature (° C.) | time (h) | product(s) | conversion (%) |
|---|---|---|---|---|
| 1-hexene | 45 | 4 | hexane (2-hexene) | 58 (26) |
|  |  | 8 |  | 87 (13) |
|  |  | 24 |  | 94 (6) |
| phenylacetylene | 45 | 4 | styrene(ethylbenzene) | 82 (11) |
|  |  | 8 |  | 25 (75) |
|  |  | 24 |  | 0 (100) |
| acrylonitrile | 45 | 4 | propionitrile | 47 |
|  |  | 8 |  | 74 |
|  |  | 24 |  | 100 |
| allyamine | 45 | 4 | propylamine | 36 |
|  |  | 8 |  | 50 |
|  |  | 24 |  | 84 |
| cyclohexene | 45 | 4 | cyclohexane | 34 |
|  |  | 8 |  | 50 |
|  |  | 24 |  | 84 |
| dimethyl-2-methylene succinate | 45 | 4 | dimethyl methylsuccinate | 49 |
|  |  | 8 |  | 62 |
|  |  | 24 |  | 78 |

TABLE 22

Series 22 (Hydrogenation of Substrates with 5 mol % RuHCl(PPh$_3$)$_2$[(CH$_3$OCH$_2$CH$_2$)$_2$benzim] (A.22) in DCM-d2, 4 atm H$_2$ atmosphere)

| substrate | time (h) | product(s) | conversion (%) |
|---|---|---|---|
| 1-hexene | 4 | hexane (2-hexene) | 6.5 (3.8) |
|  | 8 |  | 59.9 (5.4) |
|  | 24 |  | 90.9 (9.1) |
| cyclohexene | 4 | cyclohexane | 10 |
|  | 8 |  | 26 |
|  | 24 |  | 64.3 |
| dimethyl itaconate | 4 | dimethyl methylsuccinate | 73 |
|  | 8 |  | 95 |
|  | 24 |  | 100 |

TABLE 23

Series 23 (Hydrogenation of 1-hexene with Ru[(t-hexyl-OCH$_2$CH$_2$)$_2$Im]HCl(PPh$_3$)$_2$ (A.26) and Ru[(PhOCH$_2$CH$_2$)$_2$Im]HCl(PPh$_3$)$_2$ (29), respectively) (*: these spectra were taken after 6 hours))

| | Ru[(t-hexyl-OCH$_2$CH$_2$)$_2$Im]HCl(PPh$_3$)$_2$ (26) | | Ru[(PhOCH$_2$CH$_2$)$_2$Im]HCl(PPh$_3$)$_2$ (29) | |
|---|---|---|---|---|
| time (h) | 2-hexene (%) | hexane (%) | 2-hexene (%) | hexane (%) |
| 4 | 42 | 39 | 27* | 73* |
| 8 | 42 | 49 | 22 | 78 |
| 24 | 14 | 86 | 9 | 91 |

TABLE 24

Series 24 (Hydrogenation of cyclohexene with Ru[(t-hexyl-OCH$_2$CH$_2$)$_2$Im]HCl(PPh$_3$)$_2$ (A.26) and Ru[(PhOCH$_2$CH$_2$)$_2$Im]HCl(PPh$_3$)$_2$ (29), respectively) (*: this spectrum was taken after 6 hours))

| time (h) | Ru[(t-hexyl-OCH$_2$CH$_2$)$_2$Im]HCl(PPh$_3$)$_2$ (26) | Ru[(PhOCH$_2$CH$_2$)$_2$Im]HCl(PPh$_3$)$_2$ (29) |
|---|---|---|
| 4 | 15 | 46* |
| 8 | 28 | 59 |
| 4 | 54 | 86 |

TABLE 25

Series 25 (Hydrogenation of dimethyl-2-methylene succinate (*: this spectrum was taken after 6 hours))

| time (h) | Ru[(t-hexyl-OCH$_2$CH$_2$)$_2$Im]HCl(PPh$_3$)$_2$ (26) | Ru[(PhOCH$_2$CH$_2$)$_2$Im]HCl(PPh$_3$)$_2$ (29) |
|---|---|---|
| 4 | 26 | 86* |
| 8 | 38 | 97 |
| 24 | 79 | 100 |

The invention claimed is:

1. A Ruthenium-based complex catalyst according to general formula (I)

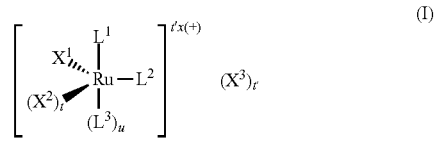

wherein $X^1$ and $X^2$ are identical or different and represent anionic ligands, $X^3$ represents a non-coordinating anion, t is 1, t' is either 0 or 1, u is 1, $L^1$, $L^2$ and $L^3$ represent identical or different ligands, wherein at least one of $L^1$, $L^2$ and $L^3$ represents either a ligand having the general structure (Ia*) or (Ib*)

2. The ruthenium-based complex catalyst according to claim 1, having the general formula (I)

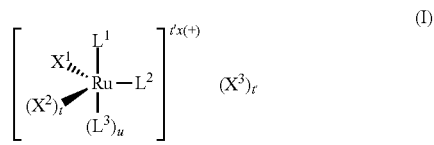

wherein
$X^1$, $X^2$ are identical or different and represent anionic ligands,
$X^3$ represents a non-coordinating anion,
t is 1,
t' is either 0 or 1,
u is 1, and
$L^1$, $L^2$, $L^3$ represent identical or different ligands, wherein at least one of $L^1$, $L^2$ and $L^3$ represents either a ligand having the general structure (Ia) or (Ib)

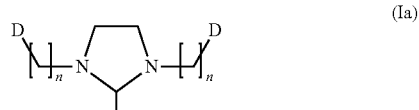

(Ia)

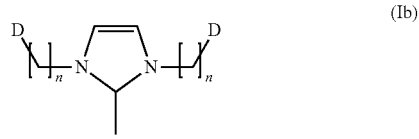

(Ib)

or a ligand having the general structure (Ic) or (Id)

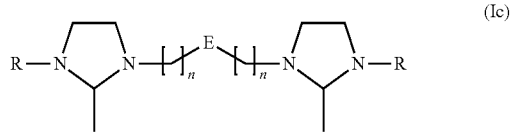

(Ic)

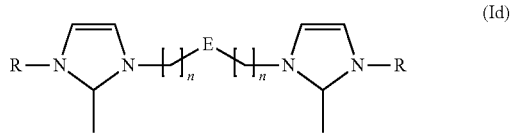

(Id)

in which formulae (Ia), (Ib), (Ic) and (Id)
n is identical or different and represents an integer of 1 to 20,
D is identical or different and represents hydroxy, alkoxy, aryloxy, thiol, thiolata, thioether, selenol, salenoether, amine, phosphine, phosphate, phosphite, arsine, sulfoxide, sulfone, phosphinimine, aminophosphine, carbene, seienoxide, imidazoline, imidazolidine, phosphine oxide, phosphine sulfide, phosphine selenide, ketone, ester, pyridyl, substituted pyridyl or any moiety able of acting as a two electron donor,
R is identical or different and represents H, alkyl or aryl, and
E is identical or different and represents a divalent moiety able of acting as a two electron donor selected from the group consisting of —O—,

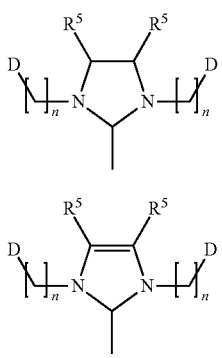

(Ia*)

(Ib*)

or a ligand having the general structure (Ic*) or (Id*)

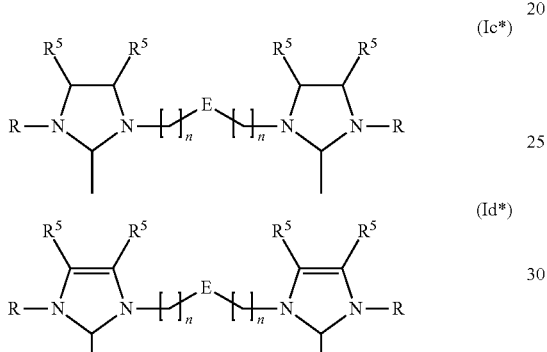

(Ic*)

(Id*)

in which formulae (Ia*), (Ib*), (Ic*) and (Id*)
n is identical or different and represents an integer of 1 to 20,
D is identical or different and represents hydroxy, alkoxy, aryloxy, thiol, thiolate, thioether, seienol, selenoether, amine, phosphine, phosphate, phosphite, arsine, suifoxide, sulfone, phosphinimine, aminophosphine, carbene, selenoxide, imidazoline, imidazolidine, phosphine oxide, phosphine sulfide, phosphine selenide, ketone, ester, pyridyl, substituted pyridyl or any moiety able of acting as a two electron donor,
R is identical or different and represents H, alkyl or aryl, and
E is identical or different and represents a divalent moiety able of acting as a two electron donor selected from the group consisting of —O—, —S—, —Se—, —N(R)—, —P(R)—, —As(R)—, —S(=O)—, —PR(=S)—, —PR(=O)—, —C(=O)—, —C(=S)—, 2,6-pyridylene, substituted 2,6-pyridylene and any other divalent moiety able of acting as a two electron donor, and
$R^5$ are identical or different in a respective moiety (Ia*), (Ib*), (Ic*) or (Id*) and represent H, alkyl, aryl, halide, or in the alternative two $R^5$ together with the two adjacent carbon atoms to which they are bound in a moiety (Ia*), (Ib*), (Ic*) or (Id*) form a fused-on five- or six-membered saturated or unsaturated ring.

—S—, —Se—, —N(R)—, —As(R)—, —S(=O)—, —PR(=S)—, —PR(=O)—, —C(=O)—, —C(=S)—, 2,6-pyridylene, substituted 2,6-pyridylene and any other divalent moiety able of acting as a two electron donor.

3. The catalyst according to claim 2, wherein:

$L^1$, $L^2$, $L^3$ represent identical or different ligands, wherein at least one of $L^1$, $L^2$ and $L^3$ represents either a ligand having the general structure (Ia) or (Ib) or a ligand having the general structure (Ic) or (Id) and wherein n, R and E have the same meanings as given in claim 2, and D is identical or different and represents hydroxy, alkoxy, aryloxy, thiol, thiolate, thioether, sulfoxide, sulfone, phosphine oxide, phosphine sulfide, ketone, ester, or any moiety able of acting as a two electron donor.

4. A ruthenium-based complex catalyst according to general formula (I)

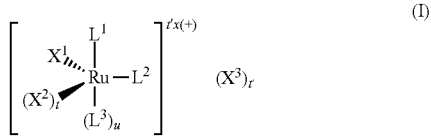

(I)

in which:

$X^1$, $X^2$ are identical or different and represent hydride, halide, pseudohalide, alkoxide, amide, tosylate, triflate, phosphate, borate, carboxylate, acetate, halogenated acetate, halogenated alkylsulfonate, or a weakly coordinating anion, $X^3$ represents a non-coordinating anion, t is 1, t' is either 0 or 1, u is 1, one ligand of $L^1$, $L^2$, and $L^3$ has the general structure according to formulae (Ia) or (Ib),

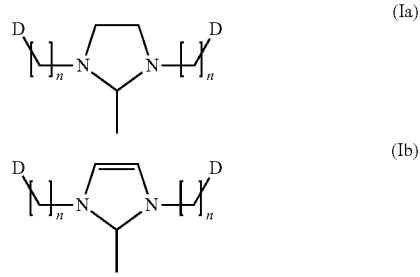

wherein n is identical or different and represents an integer of 1 to 20,

D is identical or different and represents hydroxy, alkoxy, aryloxy, thiol, thiolate, thioether, selenol, selenoether, amine, phosphine, phosphate, arsine, sulfoxide, sulfone, alkyl, phosphinimine, aminophosphine, carbene, selenoxide, imidazoline, imidazoltdine, phosphine oxide, phosphine sulfide, phosphine selenide, ketone, ester, pyridyl, substituted pyridyl, or any other moiety able of acting as a two electron donor, R is identical or different and represents H, alkyl or aryl, E is identical or different and represents a divalent moiety able of acting as a two electroted from the group consisting of —O—, —S—, —Se—, —N(R)—, —P(R)—, —As(R)—, —S(=O)—, —PR(=S)—, —PR(=O)—, —C(=O)—, —C(=S)—, 2,6-pyridylene, substituted 2,6-pyridylene and any other divalent moiety able of acting as a two electron donor, and the remainder ligand(s) of $L^1$, $L^2$, and $L^3$ being a ligand/ligands different from the one of formulae (Ia) and (Ib).

5. The catalyst according to claim 2, in which:

$X^1$, $X^2$ are identical or different and represent hydride, halide, pseudohalide, alkoxide, amide, tosylate, triflate, phosphate, borate, carboxylate, acetate, halogenated acetate, halogenated alkylsulfonate, or a weakly coordinating anion, one ligand of $L^1$, $L^2$, and $L^3$ has the general structure according to formulae (Ia) or (Ib), wherein n is identical or different and represents an integer of 1 to 5, D is identical or different and represents $C_1$-$C_{10}$ alkoxy or $C_6$-$C_{14}$ aryloxy, with the remainder ligand(s) of $L^1$, $L^2$, and $L^3$ being a ligand/ligands different from the one of formulae (Ia) and (Ib), and selected from the group consisting of $PPh_3$, $P(p-Tol)_3$, $P(o-Tol)_3$, $PPh(CH_3)_2$, $P(CF_3)_3$, $P(p-FC_6H_4)_3$, $P(p-CF_3C_6H_4)_3$, $P(C_6H_4-SO_3Na)_3$, $P(CH_2C_6H^4-SO_3Na)_3$, $P(isopropyl)_3$, $P(CHCH_3(CH_2CH_3))_3$, $P(cyclopentyl)_3$, $P(cyclohexyl)_3$, $P(neopentyl)_3$, $P(benzyl)_3$, and an imidazoline or imidazolidine ligand having the general formulae (IIa), or (IIb),

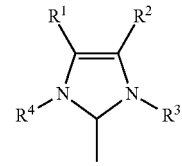

(IIa)

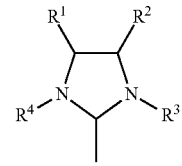

(IIb)

wherein, under the proviso that the ligand(s) according to formulae (IIa) and (IIb) are different from those of the general formulae (Ia), (Ib), (Ic) and (Id), $R^1$, $R^2$, $R^3$, $R^4$ are identical or different and are each hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-alkoxycarbonyl, $C_1$-$C_{20}$-alkylthio, $C_6$-$C_{20}$-arylthio, $C_1$-$C_{20}$-alkylsulphonyl, $C_1$-$C_{20}$-alkylsulphonate, $C_6$-$C_{20}$-arylsulphonate, or $C_1$-$C_{20}$-alkylsulphinyl, or in the alternative, $R^3$ and $R^4$ have the above mentioned meanings and $R^1$ and $R^2$ jointly form a $C_6$-$C_{10}$ cyclic structure together with the two adjacent carbon atoms in the imidazoline or imidazolidine ring.

6. The catalyst according to claim 2, in which:
$X^1$, $X^2$ are different and represent hydride or halide,
one ligand of $L^1$, $L^2$, and $L^3$ has the general structure according to formulae (Ia) or (Ib),
wherein
n is identical or different and represents an integer of 1 to 5,
D is identical or different and represents $C_1$-$C_{10}$ alkoxy or $C_6$-$C_{14}$ aryloxy,
with the remainder ligand(s) of $L^1$, $L^2$, and $L^3$ being a ligand/ligands different from the one of formulae (Ia) and (Ib), and selected from the group consisting of $PPh_3$, $P(p\text{-Tol})_3$, $P(o\text{-Tol})_3$, $PPh(CH_3)_2$, $P(CF_3)_3$, $P(p\text{-}FC_6H_4)_3$, $P(p\text{-}CF_3C_6H_4)_3$, $P(C_6H_4\text{—}SO_3Na)_3$, $P(CH_2C_6H_4\text{—}SO_3Na)_3$, $P(\text{isopropyl})_3$, $P(CHCH_3(CH_2CH_3))_3$, $P(\text{cyclopentyl})_3$, $P(\text{cyclohexyl})_3$, $P(\text{neopentyl})_3$, and $P(\text{benzyl})_3$.

7. The catalyst according to claim 2, in which:
$X^1$, $X^2$ are identical or different and represent hydride, halide, pseudohalide, alkoxide, amide, tosylate, triflate, phosphate, borate, carboxylate, acetate, halogenated acetate, halogenated alkylsulfonate, or a weakly coordinating anion,
one ligand of $L^1$, $L^2$, and $L^3$ has the general structure according to formulae (Ia-1) or (Ib-1)

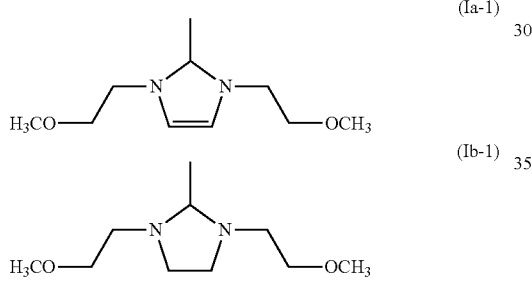

with the remainder ligand(s) of $L^1$, $L^2$, and $L^3$ being a ligand/ligands different from the one of formulae (Ia) and (Ib), and selected from the group consisting of $PPh_3$, $P(p\text{-Tol})_3$, $P(o\text{-Tol})_3$, $PPh(CH_3)_2$, $P(CF_3)_3$, $P(p\text{-}FC_6H_4)_3$, $P(p\text{-}CF_3C_6H_4)_3$, $P(C_6H_4\text{—}SO_3Na)_3$, $P(CH_2C_6H_4\text{—}SO_3Na)_3$, $P(\text{isopropyl})_3$, $P(CHCH_3(CH_2CH_3))_3$, $P(\text{cyclopentyl})_3$, $P(\text{cyclohexyl})_3$, $P(\text{neopentyl})_3$, and $P(\text{benzyl})_3$.

8. The catalyst according to claim 2, in which:
$X^1$, $X^2$ are identical or different and represent hydride, halide, pseudohalide, alkoxide, amide, tosylate, triflate, phosphate, borate, carboxylate, acetate, halogenated acetate, halogenated alkylsulfonate, or a weakly coordinating anion,
one ligand of $L^1$, $L^2$, and $L^3$ has the general structure according to formulae (Ic) or (Id) in which
n is identical or different and represents an integer of 1 to 20,
R is identical or different and represents H, alkyl or aryl,
E is identical or different and represents a divalent moiety able of acting as a two electron donor selected from the group consisting of —O—, —S—, —Se—, —N(R)—, —P(R)—, —As(R)—, —S(=O)—, —PR$_3$(=S)—, —PR$_3$(=O)—, —C(=O)—, —C(=S)—, 2,6-pyridylene, substituted 2,6-pyridylene, and any other divalent moiety able of acting as a two electron donor,
with the remainder ligand(s) of $L^1$, $L^2$, and $L^3$ being a ligand/ligands different therefrom.

9. The catalyst according to claim 2, in which:
$X^1$, $X^2$ are identical or different and represent hydride, halide, in particular fluoride, chloride, bromide or iodide, pseudohalide, alkoxide, amide, tosylate, triflate, phosphate, borate, carboxylate, acetate, halogenated acetate, halogenated alkylsulfonate or a weakly coordinating anion,
one ligand of $L^1$, $L^2$, and $L^3$ has the general structure according to formulae (Ic) or (Id) in which
n is identical or different and represents an integer of 1 to 5,
R is identical or different and represents $C_1$-$C_{10}$ alkyl or $C_6$-$C_{24}$ aryl, and
E is identical or different and represents oxygen, or sulfur,
with the remainder ligand(s) of $L^1$, $L^2$, and $L^3$ being a ligand/ligands different therefrom, and selected from the group consisting of $PPh_3$, $P(p\text{-Tol})_3$, $P(o\text{-Tol})_3$, $PPh(CH_3)_2$, $P(CF_3)_3$, $P(p\text{-}FC_6H_4)_3$, $P(p\text{-}CF_3C_6H_4)_3$, $P(C_6H_4\text{—}SO_3Na)_3$, $P(CH_2C_6H_4\text{—}SO_3Na)_3$, $P(\text{isopropyl})_3$, $P(CHCH_3(CH_2CH_3))_3$, $P(\text{cyclopentyl})_3$, $P(\text{cyclohexyl})_3$, $P(\text{neopentyl})_3$, and $P(\text{benzyl})_3$.

10. The catalyst according to claim 9, in which:
$X^1$, $X^2$ are different and represent hydride or halide,
one ligand of $L^1$, $L^2$, and $L^3$ has the general structure according to formulae (Ic) or (Id) in which
n is identical or different and represents an integer of 1 to 5,
R is identical or different and represents $C_1$-$C_{10}$ alkyl or $C_6$-$C_{24}$ aryl,
E is identical or different and represents oxygen, sulfur,
with the remainder ligand(s) of $L^1$, $L^2$, and $L^3$ being a ligand/ligands different therefrom, and selected from the group consisting of $PPh_3$, $P(p\text{-Tol})_3$, $P(o\text{-Tol})_3$, $PPh(CH_3)_2$, $P(CF_3)_3$, $P(p\text{-}FC_6H_4)_3$, $P(p\text{-}CF_3C_6H^4)_3$, $P(C_6H_4\text{—}SO_3Na)_3$, $P(CH_2C_6H_4\text{—}SO_3Na)_3$, $P(\text{isopropyl})_3$, $P(CHCH_3(CH_2CH_3))_3$, $P(\text{cyclopentyl})_3$, $P(\text{cyclohexyl})_3$, $P(\text{neopentyl})_3$, and $P(\text{benzyl})_3$.

11. The catalyst according to claim 9, in which:
$X^1$, $X^2$ are identical or different and represent hydride, halide, pseudohalide, alkoxide, amide, tosylate, triflate, phosphate, borate, carboxylate, acetate, halogenated acetate, halogenated alkylsulfonate, or a weakly coordinating anion,
one ligand of $L^1$, $L^2$, and $L^3$ has the general structure according to formulae (Ic-1)

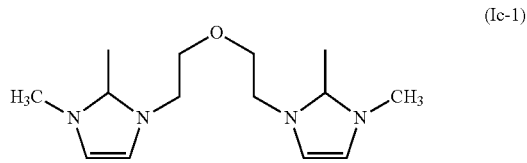

with the remainder ligand(s) of $L^1$, $L^2$, and $L^3$ being a ligand/ligands different therefrom, and selected from the group consisting of $PPh_3$, $P(p\text{-Tol})_3$, $P(o\text{-Tol})_3$, $PPh(CH_3)_2$, $P(CF_3)_3$, $P(p\text{-}FC_6H_4)_3$, $P(p\text{-}CF_3C_6H_4)_3$, $P(CH_2H_4\text{—}SO_3Na)_3$, $P(CH_2C_6H_4\text{—}SO_3Na)_3$, $P(\text{isopropyl})_3$, $P(CHCH_3(CH_2CH_3))_3$, $P(\text{cyclopentyl})_3$, $P(\text{cyclchexyl})_3$, $P(\text{neopentyl})_3$, and $P(\text{benzyl})_3$.

12. A process for hydrogenating substrates possessing at least one carbon-carbon double bond, the process comprising subjecting the substrate possessing at least one carbon-carbon double bond to a hydrogenation reaction in the presence of the catalyst according to claim 1 or 2.

13. The process according to claim 12, wherein the substrate to be hydrogenated is selected from the group consisting of terminal olefins, internal olefins, cyclic olefins, conjugated olefins, any further olefins having at least one carbon-carbon double bond and additionally at least one further polar unsaturated double or triple bond, and polymers having carbon-carbon double bonds.

14. The process according to claim 12, wherein the substrate is selected from the group consisting of hydrocarbon compounds with a terminal unsaturated carbon-carbon double bond having the general formula $C_nH_{2n}$; hydrocarbon compounds with an internal unsaturated carbon-carbon double bond having the general formula $C_nH_{2n}$; cyclic hydrocarbon compounds with an unsaturated carbon-carbon double bond having a general formula $C_nH_{2n-2}$; hydrocarbon compounds with at least two conjugated unsaturated carbon-carbon double bonds; and olefins having a unsaturated carbon-carbon double bond in the presence of at least one other unsaturated polar bond.

15. The process according to claim 12, wherein the substrate is a polymer having carbon-carbon double bonds, and the polymer comprises repeating units based on at least one conjugated diene monomer.

16. The process according to claim 15, wherein the substrate is a nitrile rubber comprising repeating units of at least one conjugated diene, at least one α,β-unsaturated nitrile and, if appropriate, one or more further copolymerizable monomers.

17. The process according to claim 14, wherein:
the hydrocarbon compound with a terminal unsaturated carbon-carbon double bond having the general formula $C_nH_{2n}$ comprises a straight-chain or a branched hydrocarbon compound of any length;
the hydrocarbon compounds with an internal unsaturated carbon-carbon double bond having the general formula $C_nH_{2n}$ comprises a straight-chain or branched hydrocarbon compound of any length;
the cyclic hydrocarbon compounds with an unsaturated carbon-carbon double bond having a general formula $C_nH_{2n-2}$ comprises cyclohexene;
the hydrocarbon compounds with at least two conjugated unsaturated carbon-carbon double bonds comprises a straight-chain or a branched hydrocarbon compound with at least two conjugated unsaturated double bonds; and
the olefins having a unsaturated carbon-carbon double bond in the presence of at least one other unsaturated polar bond comprise olefins with at least one terminal, internal, cyclic or conjugated carbon-carbon double bond and at least one further unsaturated polar bond selected from carbon-nitrogen, carbon-phosphorus, carbon-oxygen, and carbon-sulfur unsaturated polar bonds.

18. The process according to claim 16, wherein the substrate is a nitrite rubber comprising repeating units of at least one conjugated diene selected from the group consisting of 1,3-butadiene, isoprene, 2,3-dimethylbutadiene, piperylene and mixtures thereof, of at least one α,β-unsaturated nitrite selected from the group consisting of acrylonitrile, methacrylonitrile, ethactylonitnle and mixtures thereof, and optionally of one or more further copolymerizable monomers selected from the group consisting of α,β-unsaturated monocarboxylic, dicarboxylic adds, their esters or amides.

19. A ruthenium-based complex catalyst according to formula (I)

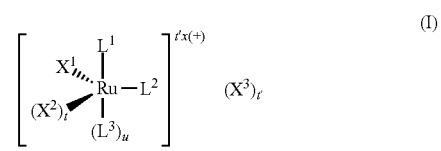

wherein:
$X^1$, $X^2$ are identical or different and represent hydride, halide, pseudohalide, alkoxide, amide, tosylate, triflate, phosphate, borate, carboxylate, acetate, halogenated acetate, halogenated aikylsulfonate, or a weakly coordinating anion,
$X^3$ represents a non-coordinating anion,
t is either 0 or 1,
t' is either 0 or 1,
u is either 0 or 1, wherein u and t may not both represent 0 at the same time, and
$L^1$, $L^2$, $L_3$ represent identical or different ligands, wherein one ligand of $L^1$, $L^2$, and $L^3$ has the general structure according to formulae (Ic) or (Id)

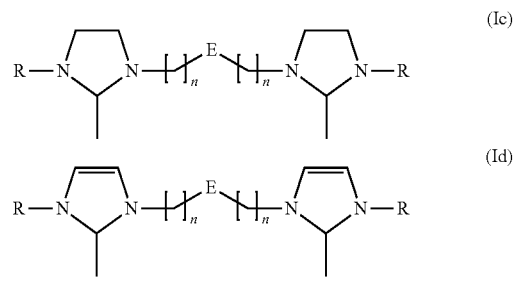

in which
n is identical or different and represents an integer of 1 to 5,
R is identical or different and represents $C_1$-$C_{10}$ alkyl or $C_6$-$C_{24}$ aryl, and
E is identical or different and represents oxygen, or sulfur,
with the remainder ligand(s) of $L^1$, $L^2$, and (if u=1) $L^3$ being a ligand/ligands different therefrom, and selected from the group consisting of $PPh_3$, $P(p\text{-Tol})_3$, $P(o\text{-Tol})_3$, $PPh(CH_3)_2$, $P(CF_3)_3$, $P(p\text{-FC}_6H_4)_3$, $P(p\text{-CF}_3C_6H_4)_3$, $P(C_6H^4\text{—SO}_3Na)_3$, $P(CH_2C_6H_4\text{—SO}_3Na)_3$, $P(\text{isopropyl})_3$, $P(CHCH_3(CH_2CH_3))_3$, $P(\text{cyclopentyl})_3$, $P(\text{cyclohexyl})_3$, $P(\text{neopentyl})_3$, and $P(\text{benzyl})_3$.

* * * * *